United States Patent
Callas et al.

(10) Patent No.: US 11,931,096 B2
(45) Date of Patent: Mar. 19, 2024

(54) SYSTEM AND METHOD FOR ELECTRICALLY ABLATING TISSUE OF A PATIENT

(71) Applicant: ANGIODYNAMICS, INC., Latham, NY (US)

(72) Inventors: Peter Callas, Castro Valley, CA (US); David Warden, Belmont, CA (US); Robert M. Pearson, San Jose, CA (US)

(73) Assignee: ANGIODYNAMICS, INC., Latham, NY (US)

( * ) Notice: Subject to any disclaimer, the term of this patent is extended or adjusted under 35 U.S.C. 154(b) by 476 days.

(21) Appl. No.: 17/346,733

(22) Filed: Jun. 14, 2021

(65) Prior Publication Data

US 2021/0369325 A1    Dec. 2, 2021

Related U.S. Application Data

(63) Continuation of application No. 16/222,319, filed on Dec. 17, 2018, now Pat. No. 11,033,324, which is a
(Continued)

(51) Int. Cl.
*A61B 18/14* (2006.01)
*A61B 34/00* (2016.01)
*A61B 18/00* (2006.01)

(52) U.S. Cl.
CPC ...... *A61B 18/14* (2013.01); *A61B 2018/0016* (2013.01); *A61B 2018/00577* (2013.01);
(Continued)

(58) Field of Classification Search
CPC . A61B 18/14; A61B 34/25; A61B 2018/0016; A61B 2018/00577;
(Continued)

(56) References Cited

U.S. PATENT DOCUMENTS 1,329,496 A    2/1920  Binkley
1,351,661 A    8/1920  Kaufman
(Continued)

FOREIGN PATENT DOCUMENTS

AU    7656800 A    4/2001
AU    2002315095 A1    12/2002
(Continued)

OTHER PUBLICATIONS

Sel, D. et al. Sequential finite element model of tissue electropermeabilization. IEEE Transactions on Biomedical Engineering 52, 816-827, doi:10.1109/tbme.2005.845212 (2005).
(Continued)

*Primary Examiner* — Lindsey G Wehrheim
(74) *Attorney, Agent, or Firm* — Heslin Rothenberg Farley & Mesiti P.C.

(57) ABSTRACT

System for electrically ablating tissue of a patient through a plurality of electrodes includes a memory, a processor and a treatment control module stored in the memory and executable by the processor. The treatment control module generates an estimated treatment region based on the number of electrical pulses to be applied.

17 Claims, 9 Drawing Sheets

Related U.S. Application Data continuation of application No. 15/612,006, filed on Jun. 2, 2017, now Pat. No. 10,154,876, which is a continuation of application No. 13/273,001, filed on Oct. 13, 2011, now Pat. No. 9,700,368.

(60) Provisional application No. 61/392,905, filed on Oct. 13, 2010.

(52) U.S. Cl.
CPC ........... *A61B 2018/00613* (2013.01); *A61B 2018/00642* (2013.01); *A61B 2018/143* (2013.01); *A61B 34/25* (2016.02)

(58) Field of Classification Search
CPC ........... A61B 2018/00613; A61B 2018/00642; A61B 2018/143
See application file for complete search history.

(56) References Cited

U.S. PATENT DOCUMENTS

| | | |
|---|---|---|
| 1,376,652 A | 5/1921 | Steedman |
| 1,380,272 A | 5/1921 | Tomasulo |
| 1,430,015 A | 9/1922 | Icher |
| 1,437,941 A | 12/1922 | Hoover |
| 1,442,697 A | 1/1923 | Orthmann |
| 1,443,360 A | 1/1923 | Grace |
| 1,445,198 A | 2/1923 | Bornmann |
| 1,450,391 A | 4/1923 | Shaw |
| 3,437,941 A | 4/1969 | Leary |
| 3,634,460 A | 1/1972 | Nelson |
| 3,639,545 A | 2/1972 | Wilcox |
| 3,730,238 A | 5/1973 | Butler |
| 3,746,004 A | 7/1973 | Jankelson |
| 3,871,359 A | 3/1975 | Pacela |
| 4,016,866 A | 4/1977 | Lawton |
| 4,037,341 A | 7/1977 | Odle |
| 4,216,860 A | 8/1980 | Heimann |
| 4,224,949 A | 9/1980 | Scott |
| 4,267,047 A | 5/1981 | Henne |
| 4,278,092 A | 7/1981 | Borsanyi et al. |
| 4,299,217 A | 11/1981 | Sagae et al. |
| 4,304,239 A | 12/1981 | Perlin |
| 4,311,148 A | 1/1982 | Courtney |
| 4,336,881 A | 6/1982 | Babb et al. |
| 4,344,436 A | 8/1982 | Kubota |
| 4,392,855 A | 7/1983 | Oreopoulos |
| 4,406,827 A | 9/1983 | Carim |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek |
| 4,636,199 A | 1/1987 | Victor |
| 4,672,969 A | 6/1987 | Dew |
| 4,676,258 A | 6/1987 | Inokuchi |
| 4,676,782 A | 6/1987 | Yamamoto |
| 4,687,471 A | 8/1987 | Twardowski |
| 4,716,896 A | 1/1988 | Ackerman |
| 4,723,549 A | 2/1988 | Wholey |
| D294,519 S | 3/1988 | Hardy, Jr. |
| 4,756,838 A | 7/1988 | Veltman |
| 4,772,269 A | 9/1988 | Twardowski |
| 4,798,585 A | 1/1989 | Inoue |
| 4,813,929 A | 3/1989 | Semrad |
| 4,819,637 A | 4/1989 | Dormandy, Jr. |
| 4,822,470 A | 4/1989 | Chang |
| 4,836,204 A | 6/1989 | Landymore |
| 4,840,172 A | 6/1989 | Augustine |
| 4,863,426 A | 9/1989 | Ferragamo |
| 4,885,003 A | 12/1989 | Hillstead |
| 4,886,496 A | 12/1989 | Conoscenti |
| 4,886,502 A | 12/1989 | Poirier et al. |
| 4,889,634 A | 12/1989 | El-Rashidy |
| 4,903,707 A | 2/1990 | Knute |
| 4,919,148 A | 4/1990 | Muccio |
| 4,921,484 A | 4/1990 | Muccio |
| 4,920,978 A | 5/1990 | Colvin |
| 4,976,709 A | 12/1990 | Sand |
| 4,981,477 A | 1/1991 | Schon |
| 4,986,810 A | 1/1991 | Semrad |
| 4,987,895 A | 1/1991 | Heimlich |
| 5,031,775 A | 7/1991 | Kane |
| 5,053,013 A | 10/1991 | Ensminger |
| 5,071,558 A | 12/1991 | Itob |
| 5,122,137 A | 6/1992 | Lennox |
| 5,137,517 A | 8/1992 | Loney |
| 5,141,499 A | 8/1992 | Zappacosta |
| D329,496 S | 9/1992 | Wotton |
| 5,156,597 A | 10/1992 | Verreet |
| 5,186,715 A | 2/1993 | Phillips |
| 5,186,800 A | 2/1993 | Dower |
| 5,188,592 A | 2/1993 | Hakki |
| 5,190,541 A | 3/1993 | Abele |
| 5,192,312 A | 3/1993 | Orton |
| 5,209,723 A | 5/1993 | Twardowski et al. |
| 5,215,530 A | 6/1993 | Hogan |
| 5,222,997 A | 6/1993 | Montgomery |
| 5,224,933 A | 7/1993 | Bromander |
| 5,227,730 A | 7/1993 | King |
| 5,242,415 A | 9/1993 | Kantrowitz et al. |
| D343,687 S | 1/1994 | Houghton, II |
| 5,277,201 A | 1/1994 | Stern |
| 5,279,564 A | 1/1994 | Taylor |
| 5,281,213 A | 1/1994 | Milder |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross |
| 5,334,167 A | 8/1994 | Cocanower |
| 5,348,554 A | 9/1994 | Imran |
| D351,661 S | 10/1994 | Fischer |
| 5,383,917 A | 1/1995 | Desai |
| 5,391,158 A | 2/1995 | Peters |
| 5,405,320 A | 4/1995 | Twardowski et al. |
| 5,417,687 A | 5/1995 | Nardella |
| 5,424,752 A | 6/1995 | Yamazaki |
| 5,439,444 A | 8/1995 | Andersen |
| 5,458,597 A | 10/1995 | Edwards |
| 5,462,521 A | 10/1995 | Brucker |
| 5,462,644 A | 10/1995 | Woodson |
| 5,484,400 A | 1/1996 | Edwards |
| 5,484,401 A | 1/1996 | Rodriguez |
| 5,536,267 A | 7/1996 | Edwards |
| 5,540,737 A | 7/1996 | Fenn |
| 5,542,916 A | 8/1996 | Hirsch |
| 5,546,940 A | 8/1996 | Panescu et al. |
| 5,562,720 A | 10/1996 | Stern et al. |
| D376,652 S | 12/1996 | Hunt |
| 5,582,588 A | 12/1996 | Sakurai et al. |
| 5,586,982 A | 12/1996 | Abela |
| 5,588,424 A | 12/1996 | Insler |
| 5,588,960 A | 12/1996 | Edwards et al. |
| 5,599,294 A | 2/1997 | Edwards |
| 5,599,311 A | 2/1997 | Raulerson |
| 5,616,126 A | 4/1997 | Malekmehr |
| 5,620,479 A | 4/1997 | Diederich |
| 5,630,426 A | 5/1997 | Eggers et al. |
| D380,272 S | 6/1997 | Partika |
| 5,643,197 A | 7/1997 | Brucker |
| 5,645,855 A | 7/1997 | Lorenz |
| 5,653,684 A | 8/1997 | Laptewicz |
| 5,672,173 A | 9/1997 | Gough |
| 5,672,174 A | 9/1997 | Gough |
| 5,681,282 A | 10/1997 | Eggers |
| 5,683,384 A | 11/1997 | Gough et al. |
| 5,687,723 A | 11/1997 | Avitall |
| 5,690,620 A | 11/1997 | Knott |
| 5,697,905 A | 12/1997 | D Ambrosio |
| 5,700,252 A | 12/1997 | Klingenstein |
| 5,707,332 A | 1/1998 | Weinberger |
| 5,718,246 A | 2/1998 | Vona |

(56) References Cited

U.S. PATENT DOCUMENTS

| | | |
|---|---|---|
| 5,728,143 A | 3/1998 | Gough |
| 5,735,847 A | 4/1998 | Gough et al. |
| 5,749,914 A | 5/1998 | Janssen |
| 5,752,939 A | 5/1998 | Makoto |
| 5,782,827 A | 7/1998 | Gough et al. |
| 5,800,484 A | 9/1998 | Gough et al. |
| 5,807,272 A | 9/1998 | Kun et al. |
| 5,807,306 A | 9/1998 | Shapland |
| 5,807,395 A | 9/1998 | Mulier |
| 5,810,742 A | 9/1998 | Pearlman |
| 5,810,804 A | 9/1998 | Gough |
| 5,830,184 A | 11/1998 | Basta |
| 5,836,897 A | 11/1998 | Sakurai et al. |
| 5,843,182 A | 12/1998 | Goldstein |
| 5,856,081 A | 1/1999 | Fahy |
| 5,863,290 A | 1/1999 | Gough et al. |
| 5,865,787 A | 2/1999 | Shapland et al. |
| 5,866,756 A | 2/1999 | Giros et al. |
| 5,868,708 A | 2/1999 | Hart |
| 5,873,877 A | 2/1999 | McGaffigan |
| 5,904,648 A | 5/1999 | Arndt et al. |
| 5,913,855 A | 6/1999 | Gough et al. |
| 5,919,191 A | 7/1999 | Lennox et al. |
| 5,921,982 A | 7/1999 | Lesh |
| 5,944,710 A | 8/1999 | Dev et al. |
| 5,947,284 A | 9/1999 | Foster |
| 5,951,546 A | 9/1999 | Lorentzen |
| 5,954,745 A | 9/1999 | Gertler |
| 5,957,919 A | 9/1999 | Laufer |
| 5,957,963 A | 9/1999 | Dobak, III |
| 5,968,006 A | 10/1999 | Hofmann |
| 5,983,140 A | 11/1999 | Smith |
| 5,984,896 A | 11/1999 | Boyd |
| 5,993,466 A | 11/1999 | Yoon |
| 6,004,339 A | 12/1999 | Wijay |
| 6,009,647 A | 1/2000 | Feingold |
| 6,009,877 A | 1/2000 | Edwards |
| 6,010,452 A | 1/2000 | Harcourt |
| 6,010,616 A | 1/2000 | Lewis |
| 6,012,885 A | 1/2000 | Taylor |
| 6,023,638 A | 2/2000 | Swanson |
| 6,029,090 A | 2/2000 | Herbst |
| 6,033,402 A | 3/2000 | Tu |
| 6,043,066 A | 3/2000 | Mangano |
| 6,050,994 A | 4/2000 | Sherman |
| 6,055,456 A | 4/2000 | Gerber |
| 6,059,780 A | 5/2000 | Gough |
| 6,066,134 A | 5/2000 | Eggers et al. |
| 6,068,121 A | 5/2000 | McGlinch |
| 6,071,281 A | 6/2000 | Burnside |
| 6,074,374 A | 6/2000 | Fulton |
| 6,074,389 A | 6/2000 | Levine et al. |
| 6,090,016 A | 7/2000 | Kuo |
| 6,090,105 A | 7/2000 | Zepeda et al. |
| D430,015 S | 8/2000 | Himbert |
| 6,096,035 A | 8/2000 | Sodhi |
| 6,106,524 A | 8/2000 | Eggers et al. |
| 6,110,192 A | 8/2000 | Ravenscroft et al. |
| 6,113,593 A | 9/2000 | Tu |
| 6,116,330 A | 9/2000 | Salyer |
| 6,120,493 A | 9/2000 | Hofmann |
| 6,123,701 A | 9/2000 | Nezhat |
| 6,132,397 A | 10/2000 | Davis et al. |
| 6,134,460 A | 10/2000 | Chance |
| 6,135,999 A | 10/2000 | Fanton |
| 6,139,544 A | 10/2000 | Mikus |
| 6,139,545 A | 10/2000 | Utley et al. |
| 6,142,992 A | 11/2000 | Cheng |
| 6,150,148 A | 11/2000 | Nanda |
| 6,152,923 A | 11/2000 | Ryan |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed |
| 6,200,314 B1 | 3/2001 | Sherman |
| D442,697 S | 5/2001 | Hajianpour |
| 6,233,490 B1 | 5/2001 | Kasevich |
| 6,235,023 B1 | 5/2001 | Lee |
| D443,360 S | 6/2001 | Haberland |
| 6,241,725 B1 | 6/2001 | Cosman |
| D445,198 S | 7/2001 | Frattini |
| 6,258,100 B1 | 7/2001 | Alferness |
| 6,258,249 B1 | 7/2001 | Simpson |
| 6,277,114 B1 | 8/2001 | Bullivant et al. |
| 6,280,441 B1 | 8/2001 | Ryan |
| 6,283,988 B1 | 9/2001 | Laufer |
| 6,283,989 B1 | 9/2001 | Laufer |
| 6,284,140 B1 | 9/2001 | Sommermeyer |
| 6,287,293 B1 | 9/2001 | Jones et al. |
| 6,287,304 B1 | 9/2001 | Eggers et al. |
| 6,296,636 B1 | 10/2001 | Cheng |
| 6,298,726 B1 | 10/2001 | Adachi |
| 6,299,633 B1 | 10/2001 | Laufer |
| D450,391 S | 11/2001 | Hunt |
| 6,312,428 B1 | 11/2001 | Eggers |
| 6,327,505 B1 | 12/2001 | Medhkour |
| 6,328,689 B1 | 12/2001 | Gonzalez et al. |
| 6,328,735 B1 | 12/2001 | Curley |
| 6,330,478 B1 | 12/2001 | Lee |
| 6,375,634 B1 | 4/2002 | Carroll |
| 6,398,779 B1 | 6/2002 | Buysse |
| 6,403,347 B1 | 6/2002 | Bills |
| 6,405,732 B1 | 6/2002 | Edwards |
| 6,411,852 B1 | 6/2002 | Danek |
| 6,419,674 B1 | 7/2002 | Bowser |
| 6,428,802 B1 | 8/2002 | Atala |
| 6,437,551 B1 | 8/2002 | Krulevitch |
| 6,443,952 B1 | 9/2002 | Mulier et al. |
| 6,463,331 B1 | 10/2002 | Edwards |
| 6,478,793 B1 | 11/2002 | Cosman |
| 6,482,221 B1 | 11/2002 | Hebert et al. |
| 6,485,487 B1 | 11/2002 | Sherman |
| 6,488,673 B1 | 12/2002 | Laufer |
| 6,488,678 B2 | 12/2002 | Sherman |
| 6,488,680 B1 | 12/2002 | Francischelli et al. |
| 6,491,706 B1 | 12/2002 | Alferness |
| 6,493,569 B2 | 12/2002 | Foo |
| 6,493,589 B1 | 12/2002 | Medhkour |
| 6,497,704 B2 | 12/2002 | Ein-Gal |
| 6,503,248 B1 | 1/2003 | Levine |
| 6,506,189 B1 | 1/2003 | Rittman, III et al. |
| 6,514,248 B1 | 2/2003 | Eggers et al. |
| 6,520,183 B2 | 2/2003 | Amar |
| D471,640 S | 3/2003 | McMichael |
| D471,641 S | 3/2003 | McMichael |
| 6,533,784 B2 | 3/2003 | Truckai |
| 6,537,976 B1 | 3/2003 | Gupta |
| 6,540,695 B1 | 4/2003 | Burbank |
| 6,558,378 B2 | 5/2003 | Sherman |
| 6,569,162 B2 | 5/2003 | He |
| 6,575,967 B1 | 6/2003 | Leveen |
| 6,575,969 B1 | 6/2003 | Rittman, III |
| 6,589,161 B2 | 7/2003 | Corcoran |
| 6,589,174 B1 | 7/2003 | Chopra et al. |
| 6,592,594 B2 | 7/2003 | Rimbaugh |
| 6,610,054 B1 | 8/2003 | Edwards |
| 6,616,657 B2 | 9/2003 | Simpson |
| D480,816 S | 10/2003 | McMichael |
| 6,634,363 B1 | 10/2003 | Danek et al. |
| 6,638,253 B2 | 10/2003 | Breznock |
| 6,638,275 B1 | 10/2003 | McGaffigan |
| 6,666,858 B2 | 12/2003 | Lafontaine |
| 6,673,070 B2 | 1/2004 | Edwards et al. |
| 6,678,558 B1 | 1/2004 | Dimmer et al. |
| 6,682,501 B1 | 1/2004 | Nelson |
| 6,689,096 B1 | 2/2004 | Loubens et al. |
| 6,689,127 B1 | 2/2004 | Gough et al. |
| 6,694,170 B1 | 2/2004 | Mikus |
| 6,694,964 B2 | 2/2004 | Wu |
| 6,694,979 B2 | 2/2004 | Deem |
| 6,694,984 B2 | 2/2004 | Habib |
| 6,695,861 B1 | 2/2004 | Rosenberg |
| 6,712,811 B2 | 3/2004 | Underwood |
| D489,973 S | 5/2004 | Root |

(56) References Cited

U.S. PATENT DOCUMENTS

| | | |
|---|---|---|
| 6,733,516 B2 | 5/2004 | Simons |
| 6,753,171 B2 | 6/2004 | Karube |
| 6,761,716 B2 | 7/2004 | Kadhiresan |
| 6,770,070 B1 | 8/2004 | Balbierz |
| D495,807 S | 9/2004 | Agbodoe |
| 6,812,204 B1 | 11/2004 | McHale |
| 6,837,886 B2 | 1/2005 | Collins |
| 6,847,848 B2 | 1/2005 | Sterzer |
| 6,860,847 B2 | 3/2005 | Alferness |
| 6,869,430 B2 | 3/2005 | Balbierz |
| 6,881,213 B2 | 4/2005 | Ryan |
| 6,895,267 B2 | 5/2005 | Panescu |
| 6,905,480 B2 | 6/2005 | McGuckin, Jr. |
| 6,926,713 B2 | 8/2005 | Rioux |
| 6,941,950 B2 | 9/2005 | Wilson |
| 6,942,681 B2 | 9/2005 | Johnson |
| 6,958,062 B1 | 10/2005 | Gough |
| 6,960,189 B2 | 11/2005 | Bates |
| 6,972,013 B1 | 12/2005 | Zhang |
| 6,989,010 B2 | 1/2006 | Francischelli |
| 6,994,689 B1 | 2/2006 | Zadno-Azizi |
| 7,008,421 B2 | 3/2006 | Daniel |
| 7,011,094 B2 | 3/2006 | Rapacki |
| 7,012,061 B1 | 3/2006 | Reiss |
| 7,027,869 B2 | 4/2006 | Danek |
| 7,036,510 B2 | 5/2006 | Zgoda |
| 7,054,665 B2 | 5/2006 | Turner |
| 7,054,685 B2 | 5/2006 | Dimmer |
| 7,087,040 B2 | 8/2006 | McGuckin, Jr. |
| 7,097,612 B2 | 8/2006 | Bertolero |
| 7,100,616 B2 | 9/2006 | Springmeyer |
| 7,113,821 B1 | 9/2006 | Sun |
| 7,162,303 B2 | 1/2007 | Levin |
| 7,169,107 B2 | 1/2007 | Jersey-Willuhn |
| 7,232,437 B2 | 6/2007 | Berman |
| 7,250,048 B2 | 7/2007 | Francischelli |
| D549,332 S | 8/2007 | Matsumoto |
| 7,257,450 B2 | 8/2007 | Auth |
| 7,264,002 B2 | 9/2007 | Danek |
| 7,273,055 B2 | 9/2007 | Danek |
| 7,291,146 B2 | 11/2007 | Steinke |
| 7,331,940 B2 | 2/2008 | Sommerich |
| 7,331,949 B2 | 2/2008 | Marisi |
| 7,341,558 B2 | 3/2008 | De La Torre |
| 7,344,533 B2 | 3/2008 | Pearson |
| D565,743 S | 4/2008 | Phillips |
| D571,478 S | 6/2008 | Horacek |
| 7,387,626 B2 | 6/2008 | Edwards |
| 7,399,747 B1 | 7/2008 | Clair |
| D575,399 S | 8/2008 | Matsumoto |
| D575,402 S | 8/2008 | Sandor |
| 7,412,977 B2 | 8/2008 | Fields |
| 7,419,487 B2 | 9/2008 | Johnson |
| 7,434,578 B2 | 10/2008 | Dillard |
| 7,437,194 B2 | 10/2008 | Skwarek |
| 7,449,019 B2 | 11/2008 | Uchida |
| 7,451,765 B2 | 11/2008 | Adler |
| 7,455,675 B2 | 11/2008 | Schur |
| 7,476,203 B2 | 1/2009 | Devore |
| 7,488,292 B2 | 2/2009 | Adachi |
| 7,520,877 B2 | 4/2009 | Lee, Jr. |
| 7,533,671 B2 | 5/2009 | Gonzalez |
| D595,422 S | 6/2009 | Mustapha |
| 7,544,301 B2 | 6/2009 | Shah |
| 7,549,984 B2 | 6/2009 | Mathis |
| 7,553,309 B2 | 6/2009 | Buysse |
| 7,565,208 B2 | 7/2009 | Harris |
| 7,571,729 B2 | 8/2009 | Saadat |
| 7,617,005 B2 | 11/2009 | Demarais |
| 7,620,451 B2 | 11/2009 | Demarais |
| 7,620,507 B2 | 11/2009 | Richardson |
| 7,632,291 B2 | 12/2009 | Stephens |
| 7,647,115 B2 | 1/2010 | Levin |
| 7,653,438 B2 | 1/2010 | Deem |
| 7,655,004 B2 | 2/2010 | Long |
| 7,670,333 B2 | 3/2010 | Schatzberger |
| 7,674,249 B2 | 3/2010 | Ivorra |
| 7,680,543 B2 | 3/2010 | Azure |
| D613,418 S | 4/2010 | Ryan |
| 7,699,842 B2 | 4/2010 | Buysse |
| 7,706,865 B1 | 4/2010 | Snell |
| 7,717,948 B2 | 5/2010 | Demarais |
| 7,718,409 B2 | 5/2010 | Rubinsky |
| 7,722,606 B2 | 5/2010 | Azure |
| 7,742,795 B2 | 6/2010 | Stone |
| 7,763,018 B2 | 7/2010 | Decarlo |
| 7,765,010 B2 | 7/2010 | Chornenky |
| 7,771,401 B2 | 8/2010 | Hekmat |
| 7,776,035 B2 | 8/2010 | Rick |
| 7,815,571 B2 | 10/2010 | Deckman |
| 7,815,662 B2 | 10/2010 | Spivey |
| 7,824,870 B2 | 11/2010 | Kovalcheck |
| RE42,016 E | 12/2010 | Chornenky et al. |
| 7,846,108 B2 | 12/2010 | Turovskiy |
| 7,853,333 B2 | 12/2010 | Demarais |
| D630,321 S | 1/2011 | Hamilton, Jr. |
| D631,154 S | 1/2011 | Hamilton, Jr. |
| 7,874,986 B2 | 1/2011 | Deckman |
| 7,875,025 B2 | 1/2011 | Cockburn |
| 7,879,031 B2 | 2/2011 | Peterson |
| RE42,277 E | 4/2011 | Jaafar et al. |
| 7,918,852 B2 | 4/2011 | Tullis |
| 7,937,143 B2 | 5/2011 | Demarais |
| 7,938,824 B2 | 5/2011 | Chornenky |
| 7,951,582 B2 | 5/2011 | Gazit |
| 7,955,827 B2 | 6/2011 | Rubinsky |
| RE42,835 E | 10/2011 | Chornenky |
| D647,628 S | 10/2011 | Helfteren |
| 8,029,504 B2 | 10/2011 | Long |
| 8,037,591 B2 | 10/2011 | Spivey |
| 8,048,067 B2 | 11/2011 | Davalos |
| 8,052,604 B2 | 11/2011 | Lau |
| 8,057,391 B2 | 11/2011 | Lau |
| 8,062,290 B2 | 11/2011 | Buysse |
| RE43,009 E | 12/2011 | Chornenky |
| 8,070,759 B2 | 12/2011 | Stefanchik |
| 8,075,572 B2 | 12/2011 | Stefanchik |
| 8,088,072 B2 | 1/2012 | Munrow |
| 8,100,922 B2 | 1/2012 | Griffith |
| 8,109,926 B2 | 2/2012 | Azure |
| 8,114,070 B2 | 2/2012 | Rubinsky |
| 8,114,072 B2 | 2/2012 | Long |
| 8,114,119 B2 | 2/2012 | Spivey |
| 8,131,371 B2 | 3/2012 | Demarals |
| 8,131,372 B2 | 3/2012 | Levin |
| 8,145,316 B2 | 3/2012 | Deem |
| 8,145,317 B2 | 3/2012 | Demarais |
| 8,150,518 B2 | 4/2012 | Levin |
| 8,150,519 B2 | 4/2012 | Demarais |
| 8,150,520 B2 | 4/2012 | Demarais |
| 8,154,288 B2 | 4/2012 | Deimling |
| 8,157,834 B2 | 4/2012 | Conlon |
| 8,162,918 B2 | 4/2012 | Ivorra |
| 8,172,772 B2 | 5/2012 | Zwolinski |
| 8,174,267 B2 | 5/2012 | Brannan |
| 8,175,711 B2 | 5/2012 | Demarais |
| 8,180,433 B2 | 5/2012 | Brannan |
| 8,181,995 B2 | 5/2012 | Decarlo |
| 8,182,477 B2 | 5/2012 | Orszulak |
| 8,187,269 B2 | 5/2012 | Shadduck |
| 8,187,270 B2 | 5/2012 | Auth |
| 8,206,300 B2 | 6/2012 | Deckman |
| 8,211,097 B2 | 7/2012 | Leyh |
| 8,211,099 B2 | 7/2012 | Buysse |
| 8,211,125 B2 | 7/2012 | Spivey |
| 8,216,161 B2 | 7/2012 | Darlington |
| 8,221,411 B2 | 7/2012 | Francischelli |
| 8,231,603 B2 | 7/2012 | Hobbs |
| 8,240,468 B2 | 8/2012 | Wilkinson |
| 8,241,204 B2 | 8/2012 | Spivey |
| 8,242,782 B2 | 8/2012 | Brannan |
| 8,246,615 B2 | 8/2012 | Behnke |
| 8,248,075 B2 | 8/2012 | Brannan |
| 8,251,986 B2 | 8/2012 | Chornenky |

(56) References Cited

U.S. PATENT DOCUMENTS

| | | |
|---|---|---|
| 8,252,057 B2 | 8/2012 | Fox |
| 8,262,563 B2 | 9/2012 | Bakos |
| 8,262,577 B2 | 9/2012 | Munrow |
| 8,262,655 B2 | 9/2012 | Ghabrial |
| 8,262,680 B2 | 9/2012 | Swain |
| 8,267,884 B1 | 9/2012 | Hicks |
| 8,267,927 B2 | 9/2012 | Dalal |
| 8,267,936 B2 | 9/2012 | Hushka |
| 8,277,379 B2 | 10/2012 | Lau |
| 8,282,631 B2 | 10/2012 | Davalos |
| 8,287,527 B2 | 10/2012 | Brannan |
| 8,292,880 B2 | 10/2012 | Prakash |
| 8,298,222 B2 | 10/2012 | Rubinsky |
| 8,303,516 B2 | 11/2012 | Schmitz |
| 8,317,806 B2 | 11/2012 | Coe |
| 8,337,394 B2 | 12/2012 | Vakharia |
| 8,343,144 B2 | 1/2013 | Kleyman |
| 8,346,370 B2 | 1/2013 | Haley |
| 8,347,891 B2 | 1/2013 | Demarais |
| 8,348,921 B2 | 1/2013 | Ivorra |
| 8,348,938 B2 | 1/2013 | Blomgren |
| 8,353,487 B2 | 1/2013 | Trusty |
| 8,353,902 B2 | 1/2013 | Prakash |
| 8,361,006 B2 | 1/2013 | Kraemer |
| 8,361,066 B2 | 1/2013 | Long |
| 8,361,112 B2 | 1/2013 | Carroll, II |
| 8,366,712 B2 | 2/2013 | Bleich |
| 8,377,057 B2 | 2/2013 | Rick |
| 8,380,283 B2 | 2/2013 | Krieg |
| D677,798 S | 3/2013 | Hart |
| 8,394,092 B2 | 3/2013 | Brannan |
| 8,394,102 B2 | 3/2013 | Garabedian |
| 8,398,626 B2 | 3/2013 | Buysse |
| 8,398,641 B2 | 3/2013 | Wallace |
| 8,403,924 B2 | 3/2013 | Behnke |
| 8,403,926 B2 | 3/2013 | Nobis |
| 8,409,200 B2 | 4/2013 | Holcomb |
| 8,409,206 B2 | 4/2013 | Wallace |
| 8,417,328 B2 | 4/2013 | Sarfaty |
| 8,425,455 B2 | 4/2013 | Nentwick |
| 8,425,505 B2 | 4/2013 | Long |
| 8,433,423 B2 | 4/2013 | Demarais |
| 8,437,845 B2 | 5/2013 | Sarfaty |
| 8,439,907 B2 | 5/2013 | Auth |
| 8,444,640 B2 | 5/2013 | Demarais |
| 8,449,538 B2 | 5/2013 | Long |
| 8,454,594 B2 | 6/2013 | Demarais |
| 8,465,464 B2 | 6/2013 | Travis |
| 8,465,484 B2 | 6/2013 | Davalos |
| 8,469,716 B2 | 6/2013 | Fedotov |
| 8,473,067 B2 | 6/2013 | Hastings |
| 8,480,657 B2 | 7/2013 | Bakos |
| 8,480,665 B2 | 7/2013 | Decarlo |
| 8,480,666 B2 | 7/2013 | Buysse |
| 8,480,689 B2 | 7/2013 | Spivey |
| 8,489,192 B1 | 7/2013 | Hlavka |
| 8,496,574 B2 | 7/2013 | Trusty |
| 8,506,485 B2 | 8/2013 | Deckman |
| 8,506,564 B2 | 8/2013 | Long |
| 8,511,317 B2 | 8/2013 | Thapliyal |
| 8,512,329 B2 | 8/2013 | Paulus |
| 8,512,330 B2 | 8/2013 | Epstein |
| 8,518,031 B2 | 8/2013 | Boyden |
| 8,529,563 B2 | 9/2013 | Long |
| 8,542,019 B2 | 9/2013 | Brannan |
| 8,546,979 B2 | 10/2013 | Heeren |
| 8,548,600 B2 | 10/2013 | Deem |
| 8,551,069 B2 | 10/2013 | Demarais |
| 8,551,088 B2 | 10/2013 | Falkenstein |
| 8,551,097 B2 | 10/2013 | Schmitz |
| 8,562,588 B2 | 10/2013 | Hobbs |
| 8,562,598 B2 | 10/2013 | Falkenstein |
| 8,562,599 B2 | 10/2013 | Leyh |
| 8,562,602 B2 | 10/2013 | Azure |
| 8,568,401 B2 | 10/2013 | Brannan |
| 8,568,402 B2 | 10/2013 | Buysse |
| 8,568,404 B2 | 10/2013 | Brannan |
| 8,568,410 B2 | 10/2013 | Vakharia |
| 8,568,411 B2 | 10/2013 | Falkenstein |
| 8,579,894 B2 | 11/2013 | Falkenstein |
| 8,579,897 B2 | 11/2013 | Vakharia |
| 8,579,902 B2 | 11/2013 | Bleich |
| 8,585,704 B2 | 11/2013 | Schmitz |
| 8,603,087 B2 | 12/2013 | Rubinsky |
| 8,608,652 B2 | 12/2013 | Voegele |
| 8,608,739 B2 | 12/2013 | Sartor |
| 8,613,745 B2 | 12/2013 | Bleich |
| 8,617,163 B2 | 12/2013 | Bleich |
| 8,620,423 B2 | 12/2013 | Demarais |
| 8,626,300 B2 | 1/2014 | Demarais |
| 8,632,534 B2 | 1/2014 | Pearson |
| 8,634,929 B2 | 1/2014 | Chornenky |
| 8,647,338 B2 | 2/2014 | Chornenky |
| 8,647,346 B2 | 2/2014 | Bleich |
| 8,652,130 B2 | 2/2014 | Kreindel |
| 8,652,138 B2 | 2/2014 | Bleich |
| 8,652,150 B2 | 2/2014 | Swain |
| 8,663,210 B2 | 3/2014 | Tomasello |
| 8,663,228 B2 | 3/2014 | Schmitz |
| 8,668,688 B2 | 3/2014 | Rusin |
| 8,672,937 B2 | 3/2014 | Decarlo |
| 8,679,003 B2 | 3/2014 | Spivey |
| 8,684,998 B2 | 4/2014 | Demarais |
| 8,702,697 B2 | 4/2014 | Curley |
| 8,706,258 B2 | 4/2014 | Nabors, Sr. |
| 8,712,500 B2 | 4/2014 | Schmidt |
| 8,715,276 B2 | 5/2014 | Thompson |
| 8,721,637 B2 | 5/2014 | Zarins |
| 8,725,249 B2 | 5/2014 | Bar-Yoseph |
| 8,728,137 B2 | 5/2014 | Zarins |
| 8,728,138 B2 | 5/2014 | Zarins |
| 8,728,139 B2 | 5/2014 | Azure |
| 8,731,672 B2 | 5/2014 | Hlavka |
| 8,740,895 B2 | 6/2014 | Mayse |
| 8,740,896 B2 | 6/2014 | Zarins |
| 8,753,335 B2 | 6/2014 | Moshe |
| 8,768,470 B2 | 7/2014 | Deem |
| 8,771,252 B2 | 7/2014 | Gelfand |
| 8,771,260 B2 | 7/2014 | Conlon |
| 8,774,913 B2 | 7/2014 | Demarais |
| 8,774,922 B2 | 7/2014 | Zarins |
| 8,777,943 B2 | 7/2014 | Mayse |
| 8,784,463 B2 | 7/2014 | Zarins |
| 8,797,039 B2 | 8/2014 | Brannan |
| 8,801,626 B2 | 8/2014 | Sun |
| 8,805,545 B2 | 8/2014 | Zarins |
| 8,808,280 B2 | 8/2014 | Mayse |
| 8,814,860 B2 | 8/2014 | Davalos |
| 8,818,514 B2 | 8/2014 | Zarins |
| 8,821,489 B2 | 9/2014 | Mayse |
| 8,828,031 B2 | 9/2014 | Fox |
| 8,835,166 B2 | 9/2014 | Phillips |
| 8,845,559 B2 | 9/2014 | Darlington |
| 8,845,629 B2 | 9/2014 | Demarais |
| 8,845,635 B2 | 9/2014 | Daniel |
| 8,845,639 B2 | 9/2014 | Wallace |
| 8,852,163 B2 | 10/2014 | Deem |
| 8,858,550 B2 | 10/2014 | Busch-Madsen |
| 8,865,076 B2 | 10/2014 | Sarfaty |
| 8,880,185 B2 | 11/2014 | Hastings |
| 8,880,186 B2 | 11/2014 | Levin |
| 8,880,195 B2 | 11/2014 | Azure |
| 8,882,759 B2 | 11/2014 | Manley |
| 8,888,792 B2 | 11/2014 | Harris |
| 8,894,641 B2 | 11/2014 | Brannan |
| 8,903,488 B2 | 12/2014 | Callas |
| 8,906,006 B2 | 12/2014 | Chornenky |
| 8,906,011 B2 | 12/2014 | Gelbart |
| 8,906,035 B2 | 12/2014 | Zwolinski |
| 8,911,439 B2 | 12/2014 | Mayse |
| 8,915,910 B2 | 12/2014 | Falkenstein |
| 8,915,911 B2 | 12/2014 | Azure |
| 8,920,411 B2 | 12/2014 | Gelbart |
| 8,923,970 B2 | 12/2014 | Bar-Yoseph |

(56) References Cited

U.S. PATENT DOCUMENTS

| | | |
|---|---|---|
| 8,926,606 B2 | 1/2015 | Davalos |
| 8,932,287 B2 | 1/2015 | Gelbart |
| 8,932,289 B2 | 1/2015 | Mayse |
| 8,934,978 B2 | 1/2015 | Deem |
| 8,939,897 B2 | 1/2015 | Nobis |
| 8,939,970 B2 | 1/2015 | Stone |
| 8,945,121 B2 | 2/2015 | Curley |
| 8,948,865 B2 | 2/2015 | Zarins |
| 8,956,350 B2 | 2/2015 | Buysse |
| 8,958,871 B2 | 2/2015 | Demarais |
| 8,958,888 B2 | 2/2015 | Chornenky |
| 8,961,507 B2 | 2/2015 | Mayse |
| 8,961,508 B2 | 2/2015 | Mayse |
| 8,968,542 B2 | 3/2015 | Davalos |
| 8,974,451 B2 | 3/2015 | Smith |
| 8,983,595 B2 | 3/2015 | Levin |
| 8,986,294 B2 | 3/2015 | Demarais |
| 8,992,517 B2 | 3/2015 | Davalos |
| 9,005,189 B2 | 4/2015 | Davalos |
| 9,005,195 B2 | 4/2015 | Mayse |
| 9,005,198 B2 | 4/2015 | Long |
| 9,011,431 B2 | 4/2015 | Long |
| 9,017,323 B2 | 4/2015 | Miller |
| 9,017,324 B2 | 4/2015 | Mayse |
| 9,023,034 B2 | 5/2015 | Jenson |
| 9,023,037 B2 | 5/2015 | Zarins |
| 9,028,483 B2 | 5/2015 | Long |
| 9,028,485 B2 | 5/2015 | Edmunds |
| 9,039,702 B2 | 5/2015 | Miller |
| 9,049,987 B2 | 6/2015 | Conlon |
| 9,050,449 B2 | 6/2015 | Darlington |
| 9,060,761 B2 | 6/2015 | Hastings |
| 9,072,518 B2 | 7/2015 | Swanson |
| 9,072,527 B2 | 7/2015 | Deem |
| 9,078,665 B2 | 7/2015 | Moss |
| 9,084,609 B2 | 7/2015 | Smith |
| 9,089,350 B2 | 7/2015 | Willard |
| 9,101,386 B2 | 8/2015 | Wallace |
| 9,108,040 B2 | 8/2015 | Zarins |
| 9,113,888 B2 | 8/2015 | Orszulak |
| 9,119,633 B2 | 9/2015 | Gelbart |
| 9,119,634 B2 | 9/2015 | Gelbart |
| 9,125,643 B2 | 9/2015 | Hlavka |
| 9,125,661 B2 | 9/2015 | Deem |
| 9,125,666 B2 | 9/2015 | Steinke |
| 9,125,667 B2 | 9/2015 | Stone |
| 9,131,978 B2 | 9/2015 | Zarins |
| 9,138,281 B2 | 9/2015 | Zarins |
| 9,138,287 B2 | 9/2015 | Curley |
| 9,138,288 B2 | 9/2015 | Curley |
| 9,149,328 B2 | 10/2015 | Dimmer |
| 9,149,331 B2 | 10/2015 | Deem |
| 9,155,589 B2 | 10/2015 | Jenson |
| 9,173,704 B2 | 11/2015 | Hobbs |
| 9,186,198 B2 | 11/2015 | Demarais |
| 9,186,209 B2 | 11/2015 | Weber |
| 9,186,213 B2 | 11/2015 | Deem |
| 9,192,435 B2 | 11/2015 | Jenson |
| 9,192,715 B2 | 11/2015 | Gelfand |
| 9,192,790 B2 | 11/2015 | Hastings |
| 9,198,733 B2 | 12/2015 | Neal, II |
| 9,220,526 B2 | 12/2015 | Conlon |
| 9,220,558 B2 | 12/2015 | Willard |
| 9,220,561 B2 | 12/2015 | Crow |
| 9,226,772 B2 | 1/2016 | Fox |
| 9,226,790 B2 | 1/2016 | Zemel |
| 9,233,241 B2 | 1/2016 | Long |
| 9,247,952 B2 | 2/2016 | Bleich |
| 9,248,318 B2 | 2/2016 | Darlington |
| 9,254,169 B2 | 2/2016 | Long |
| 9,254,172 B2 | 2/2016 | Behnke, II |
| 9,265,557 B2 | 2/2016 | Sherman |
| 9,265,558 B2 | 2/2016 | Zarins |
| 9,276,367 B2 | 3/2016 | Brannan |
| 9,277,955 B2 | 3/2016 | Herscher |
| 9,277,969 B2 | 3/2016 | Brannan |
| 9,283,051 B2 | 3/2016 | Garcia |
| 9,289,255 B2 | 3/2016 | Deem |
| 9,295,516 B2 | 3/2016 | Pearson |
| 9,307,935 B2 | 4/2016 | Pluta |
| 9,308,039 B2 | 4/2016 | Azure |
| 9,308,043 B2 | 4/2016 | Zarins |
| 9,308,044 B2 | 4/2016 | Zarins |
| 9,314,620 B2 | 4/2016 | Long |
| 9,314,630 B2 | 4/2016 | Levin |
| 9,320,561 B2 | 4/2016 | Zarins |
| 9,320,563 B2 | 4/2016 | Brustad |
| 9,326,751 B2 | 5/2016 | Hastings |
| 9,326,817 B2 | 5/2016 | Zarins |
| 9,327,100 B2 | 5/2016 | Perry |
| 9,327,122 B2 | 5/2016 | Zarins |
| 9,339,618 B2 | 5/2016 | Deem |
| 9,351,790 B2 | 5/2016 | Zemel |
| 9,414,881 B2 | 8/2016 | Callas |
| 9,598,691 B2 | 3/2017 | Davalos |
| 9,700,368 B2 | 7/2017 | Callas |
| 9,764,145 B2 | 9/2017 | Callas |
| 9,867,652 B2 | 1/2018 | Sano |
| 9,943,599 B2 | 4/2018 | Gehl |
| 10,010,666 B2 | 7/2018 | Rubinsky |
| 10,117,701 B2 | 11/2018 | Davalos |
| 10,117,707 B2 | 11/2018 | Garcia |
| 10,143,512 B2 | 12/2018 | Rubinsky |
| 10,154,874 B2 | 12/2018 | Davalos |
| 10,238,447 B2 | 3/2019 | Neal, II |
| 10,245,098 B2 | 4/2019 | Davalos |
| 10,245,105 B2 | 4/2019 | Davalos |
| 10,272,178 B2 | 4/2019 | Davalos |
| 10,286,108 B2 | 5/2019 | Davalos |
| 10,292,755 B2 | 5/2019 | Arena |
| 10,342,600 B2 | 7/2019 | Callas |
| 10,448,989 B2 | 10/2019 | Arena |
| 10,470,822 B2 | 11/2019 | Garcia |
| 10,471,254 B2 | 11/2019 | Sano |
| 10,537,379 B2 | 1/2020 | Sano |
| 10,668,208 B2 | 6/2020 | Rubinsky |
| 10,694,972 B2 | 6/2020 | Davalos |
| 10,702,326 B2 | 7/2020 | Neal, II |
| 10,828,085 B2 | 11/2020 | Davalos |
| 10,828,086 B2 | 11/2020 | Davalos |
| 10,905,492 B2 | 2/2021 | Neal, II |
| 10,959,772 B2 | 3/2021 | Davalos |
| 11,254,926 B2 | 2/2022 | Neal, II |
| 11,272,979 B2 | 3/2022 | Garcia |
| 11,311,329 B2 | 4/2022 | Davalos |
| 11,382,681 B2 | 7/2022 | Arena |
| 11,406,820 B2 | 8/2022 | Sano |
| 11,453,873 B2 | 9/2022 | Davalos |
| 11,607,271 B2 | 3/2023 | Garcia |
| 11,607,537 B2 | 3/2023 | Latouche |
| 11,638,603 B2 | 5/2023 | Sano |
| 11,655,466 B2 | 5/2023 | Neal, II |
| 11,737,810 B2 | 8/2023 | Davalos |
| 2001/0014819 A1 | 8/2001 | Ingle |
| 2001/0039393 A1 | 11/2001 | Mori |
| 2001/0043706 A1 | 11/2001 | Masuda |
| 2001/0046706 A1 | 11/2001 | Rubinsky |
| 2001/0047167 A1 | 11/2001 | Heggeness |
| 2001/0051366 A1 | 12/2001 | Rubinsky |
| 2002/0002393 A1 | 1/2002 | Mitchell |
| 2002/0022864 A1 | 2/2002 | Mahvi |
| 2002/0040204 A1 | 4/2002 | Dev |
| 2002/0049370 A1 | 4/2002 | Laufer |
| 2002/0052601 A1 | 5/2002 | Goldberg |
| 2002/0065541 A1 | 5/2002 | Fredricks |
| 2002/0072742 A1 | 6/2002 | Schaefer |
| 2002/0077314 A1 | 6/2002 | Falk |
| 2002/0077627 A1 | 6/2002 | Johnson |
| 2002/0082543 A1 | 6/2002 | Park |
| 2002/0091362 A1 | 7/2002 | Maginot |
| 2002/0095197 A1 | 7/2002 | Lardo |
| 2002/0104318 A1 | 8/2002 | Jaafar |
| 2002/0111615 A1 | 8/2002 | Cosman |
| 2002/0112729 A1 | 8/2002 | Devore |

(56) References Cited

U.S. PATENT DOCUMENTS

| | | |
|---|---|---|
| 2002/0115208 A1 | 8/2002 | Mitchell |
| 2002/0119437 A1 | 8/2002 | Grooms |
| 2002/0120261 A1 | 8/2002 | Morris |
| 2002/0133324 A1 | 9/2002 | Weaver |
| 2002/0137121 A1 | 9/2002 | Rubinsky |
| 2002/0138075 A1 | 9/2002 | Edwards |
| 2002/0143365 A1 | 10/2002 | Herbst |
| 2002/0147462 A1 | 10/2002 | Mair |
| 2002/0156472 A1 | 10/2002 | Lee |
| 2002/0161361 A1 | 10/2002 | Sherman |
| 2002/0183684 A1 | 12/2002 | Dev |
| 2002/0183735 A1 | 12/2002 | Edwards |
| 2002/0183740 A1 | 12/2002 | Edwards |
| 2002/0188242 A1 | 12/2002 | Wu |
| 2002/0193784 A1 | 12/2002 | McHale |
| 2003/0009165 A1 | 1/2003 | Edwards |
| 2003/0014047 A1 | 1/2003 | Woloszko |
| 2003/0016168 A1 | 1/2003 | Jandrell |
| 2003/0055220 A1 | 3/2003 | Legrain |
| 2003/0059945 A1 | 3/2003 | Dzekunov |
| 2003/0074039 A1 | 4/2003 | Puskas |
| 2003/0078490 A1 | 4/2003 | Damasco |
| 2003/0088199 A1 | 5/2003 | Kawaji |
| 2003/0096407 A1 | 5/2003 | Atala |
| 2003/0105454 A1 | 6/2003 | Cucin |
| 2003/0109871 A1 | 6/2003 | Johnson |
| 2003/0127090 A1 | 7/2003 | Gifford |
| 2003/0135242 A1 | 7/2003 | Mongeon |
| 2003/0149451 A1 | 8/2003 | Chomenky |
| 2003/0153960 A1* | 8/2003 | Chornenky ............ A61N 1/327 607/72 |
| 2003/0154988 A1 | 8/2003 | Devore |
| 2003/0159700 A1 | 8/2003 | Laufer |
| 2003/0164168 A1 | 9/2003 | Shaw |
| 2003/0166181 A1 | 9/2003 | Rubinsky |
| 2003/0194808 A1 | 10/2003 | Rubinsky |
| 2003/0195385 A1 | 10/2003 | Devore |
| 2003/0195406 A1 | 10/2003 | Jenkins |
| 2003/0199050 A1 | 10/2003 | Mangano |
| 2003/0208236 A1 | 11/2003 | Heil |
| 2003/0212394 A1 | 11/2003 | Pearson |
| 2003/0212412 A1 | 11/2003 | Dillard |
| 2003/0228344 A1 | 12/2003 | Fields |
| 2003/0233091 A1 | 12/2003 | Whayne |
| 2004/0009459 A1 | 1/2004 | Anderson |
| 2004/0055606 A1 | 3/2004 | Hendricksen |
| 2004/0059328 A1 | 3/2004 | Daniel |
| 2004/0068228 A1 | 4/2004 | Cunningham |
| 2004/0116935 A1 | 6/2004 | Lechot |
| 2004/0116965 A1 | 6/2004 | Falkenberg |
| 2004/0133194 A1 | 7/2004 | Eum |
| 2004/0138715 A1 | 7/2004 | Van Groeningen |
| 2004/0167458 A1 | 8/2004 | Draghia-Akli |
| 2004/0172136 A1 | 9/2004 | Ralph |
| 2004/0176855 A1 | 9/2004 | Badylak |
| 2004/0187875 A1 | 9/2004 | He |
| 2004/0193042 A1 | 9/2004 | Scampini |
| 2004/0193097 A1 | 9/2004 | Hofmann |
| 2004/0199159 A1 | 10/2004 | Lee |
| 2004/0200484 A1 | 10/2004 | Springmeyer |
| 2004/0206349 A1 | 10/2004 | Alferness |
| 2004/0210248 A1 | 10/2004 | Gordon |
| 2004/0236376 A1 | 11/2004 | Miklavcic |
| 2004/0237340 A1 | 12/2004 | Rembrandt |
| 2004/0267256 A1 | 12/2004 | Garabedian |
| 2004/0267340 A1 | 12/2004 | Cioanta |
| 2005/0004507 A1 | 1/2005 | Schroeppel |
| 2005/0010209 A1 | 1/2005 | Lee |
| 2005/0010259 A1 | 1/2005 | Gerber |
| 2005/0013726 A1 | 1/2005 | Hill |
| 2005/0013870 A1 | 1/2005 | Freyman |
| 2005/0019830 A1 | 1/2005 | Penner |
| 2005/0020965 A1 | 1/2005 | Rioux |
| 2005/0033276 A1 | 2/2005 | Adachi |
| 2005/0048651 A1 | 3/2005 | Ryttsen |
| 2005/0054978 A1 | 3/2005 | Segal |
| 2005/0061322 A1 | 3/2005 | Freitag |
| 2005/0063974 A1 | 3/2005 | Reinhard |
| 2005/0066974 A1 | 3/2005 | Fields |
| 2005/0096537 A1 | 5/2005 | Parel |
| 2005/0096709 A1 | 5/2005 | Skwarek |
| 2005/0107781 A1 | 5/2005 | Ostrovsky |
| 2005/0112141 A1 | 5/2005 | Terman |
| 2005/0135393 A1 | 6/2005 | Benco |
| 2005/0143817 A1 | 6/2005 | Hunter |
| 2005/0171522 A1 | 8/2005 | Christopherson |
| 2005/0171571 A1 | 8/2005 | Goodin |
| 2005/0197619 A1 | 9/2005 | Rule |
| 2005/0203489 A1 | 9/2005 | Saadat |
| 2005/0216047 A1 | 9/2005 | Kumoyama |
| 2005/0228373 A1 | 10/2005 | Kelly |
| 2005/0228459 A1 | 10/2005 | Levin |
| 2005/0228460 A1 | 10/2005 | Levin |
| 2005/0234445 A1 | 10/2005 | Conquergood |
| 2005/0234523 A1 | 10/2005 | Levin |
| 2005/0261707 A1 | 11/2005 | Schatzberger |
| 2005/0267407 A1 | 12/2005 | Goldman |
| 2005/0282284 A1 | 12/2005 | Rubinsky |
| 2005/0283149 A1 | 12/2005 | Thorne |
| 2005/0288684 A1 | 12/2005 | Aronson |
| 2005/0288702 A1 | 12/2005 | McGurk |
| 2006/0004356 A1 | 1/2006 | Bilski |
| 2006/0004400 A1 | 1/2006 | McGurk |
| 2006/0009748 A1 | 1/2006 | Mathis |
| 2006/0020347 A1 | 1/2006 | Barrett |
| 2006/0024359 A1 | 2/2006 | Walker |
| 2006/0025821 A1 | 2/2006 | Gelfand |
| 2006/0030810 A1 | 2/2006 | Mandrusov |
| 2006/0074413 A1 | 4/2006 | Behzadian |
| 2006/0079838 A1 | 4/2006 | Walker |
| 2006/0079845 A1 | 4/2006 | Howard |
| 2006/0085054 A1 | 4/2006 | Zikorus |
| 2006/0089635 A1 | 4/2006 | Young |
| 2006/0106379 A1 | 5/2006 | O'Brien |
| 2006/0127703 A1 | 6/2006 | Takekuma |
| 2006/0142801 A1 | 6/2006 | Demarais |
| 2006/0149123 A1 | 7/2006 | Vidlund |
| 2006/0173490 A1 | 8/2006 | Lafontaine |
| 2006/0182684 A1 | 8/2006 | Beliveau |
| 2006/0184163 A1 | 8/2006 | Breen |
| 2006/0195146 A1 | 8/2006 | Tracey |
| 2006/0206150 A1 | 9/2006 | Demarais |
| 2006/0212032 A1 | 9/2006 | Daniel |
| 2006/0212076 A1 | 9/2006 | Demarais |
| 2006/0217702 A1 | 9/2006 | Young |
| 2006/0217704 A1 | 9/2006 | Cockburn |
| 2006/0224188 A1 | 10/2006 | Libbus |
| 2006/0224192 A1 | 10/2006 | Dimmer |
| 2006/0234752 A1 | 10/2006 | Mese |
| 2006/0235474 A1 | 10/2006 | Demarais |
| 2006/0241366 A1 | 10/2006 | Falwell |
| 2006/0247619 A1 | 11/2006 | Kaplan |
| 2006/0264807 A1 | 11/2006 | Westersten |
| 2006/0269531 A1 | 11/2006 | Beebe |
| 2006/0271111 A1 | 11/2006 | Demarais |
| 2006/0276710 A1 | 12/2006 | Krishnan |
| 2006/0278241 A1 | 12/2006 | Ruano |
| 2006/0283462 A1 | 12/2006 | Fields |
| 2006/0293713 A1 | 12/2006 | Rubinsky |
| 2006/0293725 A1 | 12/2006 | Rubinsky |
| 2006/0293730 A1 | 12/2006 | Rubinsky |
| 2006/0293731 A1 | 12/2006 | Rubinsky |
| 2006/0293734 A1 | 12/2006 | Scott |
| 2007/0016125 A1 | 1/2007 | Wong |
| 2007/0016183 A1 | 1/2007 | Lee |
| 2007/0016185 A1 | 1/2007 | Tullis |
| 2007/0021803 A1 | 1/2007 | Deem |
| 2007/0025919 A1 | 2/2007 | Deem |
| 2007/0043345 A1* | 2/2007 | Davalos ............ A61B 18/1233 606/41 |
| 2007/0055142 A1 | 3/2007 | Webler |
| 2007/0055225 A1 | 3/2007 | Dodd, III |
| 2007/0060989 A1 | 3/2007 | Deem |
| 2007/0066957 A1 | 3/2007 | Demarais |

(56) References Cited

U.S. PATENT DOCUMENTS

| | | |
|---|---|---|
| 2007/0066971 A1 | 3/2007 | Podhajsky |
| 2007/0078391 A1 | 4/2007 | Wortley |
| 2007/0078453 A1 | 4/2007 | Johnson |
| 2007/0083239 A1 | 4/2007 | Demarais |
| 2007/0088347 A1 | 4/2007 | Young |
| 2007/0093789 A1 | 4/2007 | Smith |
| 2007/0096048 A1 | 5/2007 | Clerc |
| 2007/0129711 A1 | 6/2007 | Altshuler |
| 2007/0129720 A1 | 6/2007 | Demarais |
| 2007/0129760 A1 | 6/2007 | Demarais |
| 2007/0137567 A1 | 6/2007 | Shimizu |
| 2007/0151848 A1 | 7/2007 | Novak |
| 2007/0153135 A1 | 7/2007 | Han |
| 2007/0156129 A1 | 7/2007 | Kovalcheck |
| 2007/0156135 A1 | 7/2007 | Rubinsky |
| 2007/0156136 A1 | 7/2007 | Godara |
| 2007/0173899 A1 | 7/2007 | Levin |
| 2007/0179380 A1 | 8/2007 | Grossman |
| 2007/0191589 A1 | 8/2007 | Hirota |
| 2007/0191889 A1 | 8/2007 | Lang |
| 2007/0197895 A1 | 8/2007 | Nycz |
| 2007/0203486 A1 | 8/2007 | Young |
| 2007/0203549 A1 | 8/2007 | Demarais |
| 2007/0230757 A1 | 10/2007 | Trachtenberg |
| 2007/0239099 A1 | 10/2007 | Goldfarb |
| 2007/0244521 A1 | 10/2007 | Bornzin |
| 2007/0249939 A1 | 10/2007 | Gerbi |
| 2007/0282407 A1 | 12/2007 | Demarais |
| 2007/0287950 A1 | 12/2007 | Kjeken |
| 2007/0295336 A1 | 12/2007 | Nelson |
| 2007/0295337 A1 | 12/2007 | Nelson |
| 2008/0015571 A1 | 1/2008 | Rubinsky |
| 2008/0015628 A1 | 1/2008 | Dubrul |
| 2008/0021371 A1 | 1/2008 | Rubinsky |
| 2008/0027314 A1 | 1/2008 | Miyazaki |
| 2008/0027343 A1 | 1/2008 | Fields |
| 2008/0033340 A1 | 2/2008 | Heller |
| 2008/0033417 A1 | 2/2008 | Nields |
| 2008/0045880 A1 | 2/2008 | Kjeken |
| 2008/0065062 A1 | 3/2008 | Leung |
| 2008/0071262 A1 | 3/2008 | Azure |
| 2008/0071264 A1 | 3/2008 | Azure |
| 2008/0071265 A1 | 3/2008 | Azure |
| 2008/0082145 A1 | 4/2008 | Skwarek |
| 2008/0086115 A1 | 4/2008 | Stoklund |
| 2008/0091135 A1 | 4/2008 | Draghia-Akli |
| 2008/0097139 A1 | 4/2008 | Clerc |
| 2008/0097422 A1 | 4/2008 | Edwards |
| 2008/0103529 A1 | 5/2008 | Schoenbach |
| 2008/0121375 A1 | 5/2008 | Richason |
| 2008/0125772 A1 | 5/2008 | Stone |
| 2008/0125775 A1 | 5/2008 | Morris |
| 2008/0132826 A1 | 6/2008 | Shadduck |
| 2008/0132884 A1 | 6/2008 | Rubinsky |
| 2008/0132885 A1 | 6/2008 | Rubinsky |
| 2008/0140064 A1 | 6/2008 | Vegesna |
| 2008/0146931 A1 | 6/2008 | Zhang |
| 2008/0146934 A1 | 6/2008 | Czygan |
| 2008/0147056 A1 | 6/2008 | Van Der Weide |
| 2008/0154259 A1 | 6/2008 | Gough |
| 2008/0167649 A1 | 7/2008 | Edwards |
| 2008/0171985 A1 | 7/2008 | Karakoca |
| 2008/0183256 A1 | 7/2008 | Keacher |
| 2008/0190434 A1 | 8/2008 | Tjong Joe Wai |
| 2008/0200911 A1 | 8/2008 | Long |
| 2008/0200912 A1 | 8/2008 | Long |
| 2008/0208052 A1 | 8/2008 | Lepivert |
| 2008/0210243 A1 | 9/2008 | Clayton |
| 2008/0213331 A1 | 9/2008 | Gelfand |
| 2008/0214986 A1 | 9/2008 | Ivorra |
| 2008/0224188 A1 | 9/2008 | Han |
| 2008/0234708 A1 | 9/2008 | Houser |
| 2008/0236593 A1 | 10/2008 | Nelson |
| 2008/0249503 A1 | 10/2008 | Fields |
| 2008/0255553 A1 | 10/2008 | Young |
| 2008/0262489 A1 | 10/2008 | Steinke |
| 2008/0269586 A1 | 10/2008 | Rubinsky |
| 2008/0269838 A1 | 10/2008 | Brighton |
| 2008/0275465 A1 | 11/2008 | Paul |
| 2008/0279995 A1 | 11/2008 | Schultheiss |
| 2008/0281319 A1 | 11/2008 | Paul |
| 2008/0283065 A1 | 11/2008 | Chang |
| 2008/0288038 A1 | 11/2008 | Paul |
| 2008/0294155 A1 | 11/2008 | Cronin |
| 2008/0294358 A1 | 11/2008 | Richardson |
| 2008/0306427 A1 | 12/2008 | Bailey |
| 2008/0312599 A1 | 12/2008 | Rosenberg |
| 2008/0319511 A1 | 12/2008 | Pless |
| 2009/0018206 A1 | 1/2009 | Barkan |
| 2009/0018565 A1 | 1/2009 | To |
| 2009/0018566 A1 | 1/2009 | Escudero |
| 2009/0018567 A1 | 1/2009 | Escudero |
| 2009/0024075 A1 | 1/2009 | Schroeppel |
| 2009/0024085 A1 | 1/2009 | To |
| 2009/0029407 A1 | 1/2009 | Gazit |
| 2009/0030336 A1 | 1/2009 | Woo |
| 2009/0036773 A1 | 2/2009 | Lau |
| 2009/0038752 A1 | 2/2009 | Weng |
| 2009/0062788 A1 | 3/2009 | Long |
| 2009/0062792 A1 | 3/2009 | Vakharia |
| 2009/0062795 A1 | 3/2009 | Vakharia |
| 2009/0076496 A1 | 3/2009 | Azure |
| 2009/0076499 A1 | 3/2009 | Azure |
| 2009/0076500 A1 | 3/2009 | Azure |
| 2009/0076502 A1 | 3/2009 | Azure |
| 2009/0081272 A1 | 3/2009 | Clarke |
| 2009/0088636 A1 | 4/2009 | Lau |
| 2009/0099544 A1 | 4/2009 | Munrow |
| 2009/0105703 A1 | 4/2009 | Shadduck |
| 2009/0114226 A1 | 5/2009 | Deem |
| 2009/0118725 A1 | 5/2009 | Auth |
| 2009/0118729 A1 | 5/2009 | Auth |
| 2009/0125009 A1 | 5/2009 | Zikorus |
| 2009/0138014 A1 | 5/2009 | Bonutti |
| 2009/0143705 A1 | 6/2009 | Danek |
| 2009/0157166 A1 | 6/2009 | Singhal |
| 2009/0163904 A1 | 6/2009 | Miller |
| 2009/0171280 A1 | 7/2009 | Samuel |
| 2009/0177111 A1 | 7/2009 | Miller |
| 2009/0186850 A1 | 7/2009 | Kiribayashi |
| 2009/0192508 A1 | 7/2009 | Laufer |
| 2009/0198227 A1 | 8/2009 | Prakash |
| 2009/0204005 A1 | 8/2009 | Keast |
| 2009/0204112 A1 | 8/2009 | Kleyman |
| 2009/0209955 A1 | 8/2009 | Forster |
| 2009/0216543 A1 | 8/2009 | Pang |
| 2009/0221939 A1 | 9/2009 | Demarais |
| 2009/0228001 A1 | 9/2009 | Pacey |
| 2009/0240247 A1 | 9/2009 | Rioux |
| 2009/0247933 A1 | 10/2009 | Maor |
| 2009/0248012 A1 | 10/2009 | Maor |
| 2009/0269317 A1 | 10/2009 | Davalos |
| 2009/0270756 A1 | 10/2009 | Gamache |
| 2009/0275827 A1 | 11/2009 | Aiken |
| 2009/0281477 A1 | 11/2009 | Mikus |
| 2009/0281540 A1 | 11/2009 | Blomgren |
| 2009/0287081 A1 | 11/2009 | Grossman |
| 2009/0292342 A1 | 11/2009 | Rubinsky |
| 2009/0301480 A1 | 12/2009 | Elsakka |
| 2009/0306544 A1 | 12/2009 | Ng |
| 2009/0306545 A1 | 12/2009 | Elsakka |
| 2009/0318849 A1 | 12/2009 | Hobbs |
| 2009/0318905 A1 | 12/2009 | Bhargav |
| 2009/0326366 A1 | 12/2009 | Krieg |
| 2009/0326436 A1 | 12/2009 | Rubinsky |
| 2009/0326561 A1 | 12/2009 | Carroll, II |
| 2009/0326570 A1 | 12/2009 | Brown |
| 2010/0006441 A1 | 1/2010 | Renaud |
| 2010/0016783 A1 | 1/2010 | Bourke, Jr. |
| 2010/0023004 A1 | 1/2010 | Francischelli |
| 2010/0030211 A1 | 2/2010 | Davalos |
| 2010/0036291 A1 | 2/2010 | Darlington |
| 2010/0049190 A1 | 2/2010 | Long |
| 2010/0056926 A1 | 3/2010 | Deckman |

(56) References Cited

U.S. PATENT DOCUMENTS

| | | |
|---|---|---|
| 2010/0057074 A1 | 3/2010 | Roman |
| 2010/0057076 A1 | 3/2010 | Behnke |
| 2010/0069921 A1 | 3/2010 | Miller |
| 2010/0079215 A1 | 4/2010 | Brannan |
| 2010/0082022 A1 | 4/2010 | Haley |
| 2010/0082023 A1 | 4/2010 | Brannan |
| 2010/0082024 A1 | 4/2010 | Brannan |
| 2010/0082025 A1 | 4/2010 | Brannan |
| 2010/0082083 A1 | 4/2010 | Brannan |
| 2010/0082084 A1 | 4/2010 | Brannan |
| 2010/0087813 A1 | 4/2010 | Long |
| 2010/0090696 A1 | 4/2010 | Deimling |
| 2010/0100093 A1 | 4/2010 | Azure |
| 2010/0106025 A1 | 4/2010 | Sarfaty |
| 2010/0106047 A1 | 4/2010 | Sarfaty |
| 2010/0121173 A1 | 5/2010 | Sarfaty |
| 2010/0130975 A1 | 5/2010 | Long |
| 2010/0147701 A1 | 6/2010 | Field |
| 2010/0152725 A1 | 6/2010 | Pearson |
| 2010/0160850 A1 | 6/2010 | Ivorra |
| 2010/0168735 A1 | 7/2010 | Deno |
| 2010/0174282 A1 | 7/2010 | Demarais |
| 2010/0179436 A1 | 7/2010 | Sarfaty |
| 2010/0179530 A1 | 7/2010 | Long |
| 2010/0191112 A1 | 7/2010 | Demarais |
| 2010/0191235 A1 | 7/2010 | Moshe |
| 2010/0196984 A1 | 8/2010 | Rubinsky |
| 2010/0204560 A1 | 8/2010 | Salahieh |
| 2010/0204638 A1 | 8/2010 | Hobbs |
| 2010/0211061 A1 | 8/2010 | Leyh |
| 2010/0222377 A1 | 9/2010 | Crooks |
| 2010/0222677 A1 | 9/2010 | Placek |
| 2010/0228234 A1 | 9/2010 | Hyde |
| 2010/0228247 A1 | 9/2010 | Paul |
| 2010/0241117 A1 | 9/2010 | Paul |
| 2010/0249771 A1 | 9/2010 | Pearson |
| 2010/0255795 A1 | 10/2010 | Rubinsky |
| 2010/0256624 A1 | 10/2010 | Brannan |
| 2010/0256628 A1 | 10/2010 | Pearson |
| 2010/0256630 A1 | 10/2010 | Hamilton, Jr. |
| 2010/0261994 A1 | 10/2010 | Davalos |
| 2010/0262067 A1 | 10/2010 | Chornenky |
| 2010/0268223 A1 | 10/2010 | Coe |
| 2010/0268225 A1 | 10/2010 | Coe |
| 2010/0286690 A1 | 11/2010 | Paul |
| 2010/0292686 A1 | 11/2010 | Rick |
| 2010/0298822 A1 | 11/2010 | Behnke |
| 2010/0298823 A1 | 11/2010 | Cao |
| 2010/0298825 A1 | 11/2010 | Slizynski |
| 2010/0331758 A1 | 12/2010 | Davalos |
| 2010/0331911 A1 | 12/2010 | Kovalcheck |
| 2011/0009860 A1 | 1/2011 | Chornenky |
| 2011/0015630 A1 | 1/2011 | Azure |
| 2011/0017207 A1 | 1/2011 | Hendricksen |
| 2011/0021970 A1 | 1/2011 | Vo-Dinh |
| 2011/0034209 A1 | 2/2011 | Rubinsky |
| 2011/0054458 A1 | 3/2011 | Behnke |
| 2011/0064371 A1 | 3/2011 | Leatherman |
| 2011/0064671 A1 | 3/2011 | Bynoe |
| 2011/0082362 A1 | 4/2011 | Schmidt |
| 2011/0082414 A1 | 4/2011 | Wallace |
| 2011/0092973 A1 | 4/2011 | Nuccitelli |
| 2011/0098695 A1 | 4/2011 | Brannan |
| 2011/0105823 A1 | 5/2011 | Single, Jr. |
| 2011/0106221 A1 | 5/2011 | Neal, II |
| 2011/0112434 A1 | 5/2011 | Ghabrial |
| 2011/0112531 A1 | 5/2011 | Landis |
| 2011/0118721 A1 | 5/2011 | Brannan |
| 2011/0118727 A1 | 5/2011 | Fish |
| 2011/0118729 A1 | 5/2011 | Heeren |
| 2011/0118732 A1 | 5/2011 | Rubinsky |
| 2011/0118734 A1 | 5/2011 | Auld |
| 2011/0130834 A1 | 6/2011 | Wilson |
| 2011/0135626 A1 | 6/2011 | Kovalcheck |
| 2011/0144524 A1 | 6/2011 | Fish |
| 2011/0144562 A1 | 6/2011 | Heeren |
| 2011/0144638 A1 | 6/2011 | Heeren |
| 2011/0144641 A1 | 6/2011 | Dimalanta, Jr. |
| 2011/0144657 A1 | 6/2011 | Fish |
| 2011/0152678 A1 | 6/2011 | Aljuri |
| 2011/0152906 A1 | 6/2011 | Escudero |
| 2011/0152907 A1 | 6/2011 | Escudero |
| 2011/0160514 A1 | 6/2011 | Long |
| 2011/0166499 A1 | 7/2011 | Demarais |
| 2011/0172659 A1 | 7/2011 | Brannan |
| 2011/0176037 A1 | 7/2011 | Benkley, III |
| 2011/0178570 A1 | 7/2011 | Demarais |
| 2011/0202052 A1 | 8/2011 | Gelbart |
| 2011/0202053 A1 | 8/2011 | Moss |
| 2011/0207758 A1 | 8/2011 | Sobotka |
| 2011/0208096 A1 | 8/2011 | Demarais |
| 2011/0208180 A1 | 8/2011 | Brannan |
| 2011/0217730 A1 | 9/2011 | Gazit |
| 2011/0230874 A1 | 9/2011 | Epstein |
| 2011/0245756 A1 | 10/2011 | Arora |
| 2011/0251607 A1 | 10/2011 | Kruecker |
| 2011/0282354 A1 | 11/2011 | Schulte |
| 2011/0288545 A1 | 11/2011 | Beebe |
| 2011/0301587 A1 | 12/2011 | Deem |
| 2011/0306971 A1 | 12/2011 | Long |
| 2012/0034131 A1 | 2/2012 | Rubinsky |
| 2012/0046658 A1 | 2/2012 | Kreindel |
| 2012/0059255 A1 | 3/2012 | Paul |
| 2012/0071870 A1 | 3/2012 | Salahieh |
| 2012/0071872 A1 | 3/2012 | Rubinsky |
| 2012/0071874 A1 | 3/2012 | Davalos |
| 2012/0085649 A1 | 4/2012 | Sano |
| 2012/0089009 A1 | 4/2012 | Omary |
| 2012/0090643 A1 | 4/2012 | Bertsch |
| 2012/0090646 A1 | 4/2012 | Tanaka |
| 2012/0095459 A1 | 4/2012 | Callas |
| 2012/0101538 A1 | 4/2012 | Ballakur |
| 2012/0109122 A1 | 5/2012 | Arena |
| 2012/0130289 A1 | 5/2012 | Demarais |
| 2012/0150172 A1 | 6/2012 | Ortiz |
| 2012/0165813 A1 | 6/2012 | Lee |
| 2012/0179091 A1 | 7/2012 | Ivorra |
| 2012/0220999 A1 | 8/2012 | Long |
| 2012/0226218 A1 | 9/2012 | Phillips |
| 2012/0226271 A1 | 9/2012 | Callas |
| 2012/0265183 A1 | 10/2012 | Tulleken et al. |
| 2012/0265186 A1 | 10/2012 | Burger |
| 2012/0277741 A1 | 11/2012 | Davalos |
| 2012/0303012 A1 | 11/2012 | Leyh |
| 2012/0303020 A1 | 11/2012 | Chornenky |
| 2012/0310236 A1 | 12/2012 | Placek |
| 2012/0310237 A1 | 12/2012 | Swanson |
| 2013/0023871 A1 | 1/2013 | Collins |
| 2013/0030239 A1 | 1/2013 | Weyh |
| 2013/0030430 A1 | 1/2013 | Stewart |
| 2013/0033977 A1 | 2/2013 | Lin |
| 2013/0035921 A1 | 2/2013 | Rodriguez-Ponce |
| 2013/0041436 A1 | 2/2013 | Ruse |
| 2013/0072858 A1 | 3/2013 | Watson |
| 2013/0090346 A1 | 4/2013 | Johns |
| 2013/0090646 A1 | 4/2013 | Moss |
| 2013/0108667 A1 | 5/2013 | Soikum |
| 2013/0110103 A1 | 5/2013 | Assmus |
| 2013/0110106 A1 | 5/2013 | Richardson |
| 2013/0184702 A1 | 7/2013 | Neal, II |
| 2013/0196441 A1 | 8/2013 | Rubinsky |
| 2013/0197425 A1 | 8/2013 | Golberg |
| 2013/0202766 A1 | 8/2013 | Rubinsky |
| 2013/0218157 A1 | 8/2013 | Callas |
| 2013/0230895 A1 | 9/2013 | Koblizek |
| 2013/0238062 A1 | 9/2013 | Ron Edoute |
| 2013/0253415 A1 | 9/2013 | Sano |
| 2013/0261389 A1 | 10/2013 | Long |
| 2013/0281968 A1 | 10/2013 | Davalos |
| 2013/0296679 A1 | 11/2013 | Condie |
| 2013/0338761 A1 | 12/2013 | Plowiecki |
| 2013/0345697 A1 | 12/2013 | Garcia |
| 2013/0345779 A1 | 12/2013 | Maor |
| 2014/0005664 A1 | 1/2014 | Govari |

(56) References Cited

U.S. PATENT DOCUMENTS

| | | |
|---|---|---|
| 2014/0017218 A1 | 1/2014 | Scott |
| 2014/0039489 A1 | 2/2014 | Davalos |
| 2014/0046322 A1 | 2/2014 | Callas |
| 2014/0052118 A1 | 2/2014 | Laske |
| 2014/0066913 A1 | 3/2014 | Sherman |
| 2014/0081255 A1 | 3/2014 | Johnson |
| 2014/0088578 A1 | 3/2014 | Rubinsky |
| 2014/0094792 A1 | 4/2014 | Sharonov |
| 2014/0094793 A1 | 4/2014 | Sharonov |
| 2014/0107643 A1 | 4/2014 | Chornenky |
| 2014/0111224 A1 | 4/2014 | Agate |
| 2014/0121663 A1 | 5/2014 | Pearson |
| 2014/0121728 A1 | 5/2014 | Dhillon |
| 2014/0163551 A1 | 6/2014 | Maor |
| 2014/0207133 A1 | 7/2014 | Model |
| 2014/0276748 A1 | 9/2014 | Ku |
| 2014/0296844 A1 | 10/2014 | Kevin |
| 2014/0309579 A1 | 10/2014 | Rubinsky |
| 2014/0378964 A1 | 12/2014 | Pearson |
| 2015/0025526 A1 | 1/2015 | Hua |
| 2015/0032105 A1 | 1/2015 | Azure |
| 2015/0066013 A1 | 3/2015 | Salahieh |
| 2015/0066020 A1 | 3/2015 | Epstein |
| 2015/0088120 A1 | 3/2015 | Garcia |
| 2015/0088220 A1 | 3/2015 | Callas |
| 2015/0112333 A1 | 4/2015 | Chorenky |
| 2015/0126922 A1 | 5/2015 | Willis |
| 2015/0134584 A1 | 5/2015 | Nakagawa |
| 2015/0141984 A1 | 5/2015 | Loomas |
| 2015/0152504 A1 | 6/2015 | Lin |
| 2015/0164584 A1 | 6/2015 | Davalos |
| 2015/0173824 A1 | 6/2015 | Davalos |
| 2015/0196351 A1 | 7/2015 | Stone |
| 2015/0201996 A1 | 7/2015 | Rubinsky |
| 2015/0265349 A1 | 9/2015 | Moss |
| 2015/0289923 A1 | 10/2015 | Davalos |
| 2015/0320478 A1 | 11/2015 | Cosman, Jr. |
| 2015/0320481 A1 | 11/2015 | Cosman, Jr. |
| 2015/0320488 A1 | 11/2015 | Moshe |
| 2015/0320999 A1 | 11/2015 | Nuccitelli |
| 2015/0327944 A1 | 11/2015 | Neal, II |
| 2016/0022957 A1 | 1/2016 | Hobbs |
| 2016/0066977 A1 | 3/2016 | Neal, II |
| 2016/0074114 A1 | 3/2016 | Pearson |
| 2016/0113708 A1 | 4/2016 | Moss |
| 2016/0143398 A1 | 5/2016 | Kim |
| 2016/0143698 A1 | 5/2016 | Garcia |
| 2016/0235470 A1 | 8/2016 | Callas |
| 2016/0287313 A1 | 10/2016 | Rubinsky |
| 2016/0287314 A1 | 10/2016 | Arena |
| 2016/0337310 A1 | 11/2016 | Faccin |
| 2016/0338758 A9 | 11/2016 | Davalos |
| 2016/0338761 A1 | 11/2016 | Chornenky |
| 2016/0354142 A1 | 12/2016 | Pearson |
| 2016/0367310 A1 | 12/2016 | Onik |
| 2017/0035501 A1 | 2/2017 | Chornenky |
| 2017/0065339 A1 | 3/2017 | Mickelsen |
| 2017/0137512 A1 | 5/2017 | Van Hoorick |
| 2017/0189579 A1 | 7/2017 | Davalos |
| 2017/0209620 A1 | 7/2017 | Davalos |
| 2017/0266438 A1 | 9/2017 | Sano |
| 2017/0319851 A1 | 11/2017 | Athos |
| 2017/0348525 A1 | 12/2017 | Sano |
| 2017/0360323 A1 | 12/2017 | Li |
| 2017/0360326 A1 | 12/2017 | Davalos |
| 2018/0071014 A1 | 3/2018 | Neal |
| 2018/0125565 A1 | 5/2018 | Sano |
| 2018/0161086 A1 | 6/2018 | Davalos |
| 2018/0198218 A1 | 7/2018 | Regan |
| 2019/0023804 A1 | 1/2019 | Onik |
| 2019/0029749 A1 | 1/2019 | Garcia |
| 2019/0046255 A1 | 2/2019 | Davalos |
| 2019/0069945 A1 | 3/2019 | Davalos |
| 2019/0076528 A1 | 3/2019 | Soden |
| 2019/0083169 A1 | 3/2019 | Single |
| 2019/0133671 A1 | 5/2019 | Davalos |
| 2019/0175248 A1 | 6/2019 | Neal, II |
| 2019/0175260 A1 | 6/2019 | Davalos |
| 2019/0223938 A1 | 7/2019 | Arena |
| 2019/0232048 A1 | 8/2019 | Latouche |
| 2019/0233809 A1 | 8/2019 | Neal, II |
| 2019/0256839 A1 | 8/2019 | Neal, II |
| 2019/0282294 A1 | 9/2019 | Davalos |
| 2019/0328445 A1 | 10/2019 | Sano |
| 2019/0351224 A1 | 11/2019 | Sano |
| 2019/0376055 A1 | 12/2019 | Davalos |
| 2020/0046432 A1 | 2/2020 | Garcia |
| 2020/0046967 A1 | 2/2020 | Ivey |
| 2020/0093541 A9 | 3/2020 | Neal et al. |
| 2020/0197073 A1 | 6/2020 | Sano |
| 2020/0260987 A1 | 8/2020 | Davalos |
| 2020/0289188 A1 | 9/2020 | Forsyth |
| 2020/0323576 A1 | 10/2020 | Neal |
| 2020/0405373 A1 | 12/2020 | O'Brien |
| 2021/0022795 A1 | 1/2021 | Davalos |
| 2021/0023362 A1 | 1/2021 | Lorenzo |
| 2021/0052882 A1 | 2/2021 | Wasson |
| 2021/0113265 A1 | 4/2021 | D'Agostino |
| 2021/0137410 A1 | 5/2021 | O'Brien |
| 2021/0186600 A1 | 6/2021 | Davalos |
| 2021/0361341 A1 | 11/2021 | Neal, II |
| 2021/0393312 A1 | 12/2021 | Davalos |
| 2022/0151688 A1 | 5/2022 | Garcia |
| 2022/0161027 A1 | 5/2022 | Aycock |
| 2022/0290183 A1 | 9/2022 | Davalos |
| 2022/0362549 A1 | 11/2022 | Sano |
| 2023/0157759 A1 | 5/2023 | Garcia |
| 2023/0212551 A1 | 7/2023 | Neal, II |
| 2023/0248414 A1 | 8/2023 | Sano |
| 2023/0355293 A1 | 11/2023 | Davalos |
| 2023/0355968 A1 | 11/2023 | Davalos |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| AU | 2012255070 | 1/2014 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 833111 | 3/1952 |
| DE | 60038026 | 2/2009 |
| DE | 60038026 T2 | 2/2009 |
| EP | 0218275 A1 | 4/1987 |
| EP | 0339501 A2 | 11/1989 |
| EP | 0528891 A1 | 3/1993 |
| EP | 0533511 A1 | 3/1993 |
| EP | 0908156 | 4/1999 |
| EP | 0998235 A1 | 5/2000 |
| EP | 1011495 A1 | 6/2000 |
| EP | 0528891 B1 | 7/2000 |
| EP | 1061983 A1 | 12/2000 |
| EP | 1196550 A2 | 4/2002 |
| EP | 1207797 A1 | 5/2002 |
| EP | 1344497 | 9/2003 |

(56) References Cited

FOREIGN PATENT DOCUMENTS

| | | |
|---|---|---|
| EP | 1406685 A1 | 4/2004 |
| EP | 1424970 A2 | 6/2004 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1791485 B1 | 6/2007 |
| EP | 1796568 A1 | 6/2007 |
| EP | 1207797 B1 | 2/2008 |
| EP | 1406685 B1 | 6/2008 |
| EP | 1962708 B1 | 9/2008 |
| EP | 1962710 B1 | 9/2008 |
| EP | 1962945 B1 | 9/2008 |
| EP | 1424970 B1 | 12/2008 |
| EP | 2280741 A1 | 2/2011 |
| EP | 2373241 B1 | 10/2011 |
| EP | 2381829 A1 | 11/2011 |
| EP | 2413833 A1 | 2/2012 |
| EP | 2429435 | 3/2012 |
| EP | 2488251 A2 | 8/2012 |
| EP | 2593179 | 5/2013 |
| EP | 2627274 | 8/2013 |
| EP | 2642937 A2 | 10/2013 |
| EP | 2651505 | 10/2013 |
| EP | 3143124 A1 | 3/2017 |
| EP | 3852868 A1 | 7/2021 |
| ES | 2300272 T3 | 6/2008 |
| ES | 2315493 | 4/2009 |
| JP | H10243947 A | 9/1998 |
| JP | 2001510702 A | 8/2001 |
| JP | 2002360712 A | 12/2002 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2007516792 | 6/2007 |
| JP | 2008508946 A | 3/2008 |
| JP | 4252316 A | 4/2009 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 | 9/2009 |
| JP | 2009532077 A | 9/2009 |
| JP | 2010503496 | 2/2010 |
| JP | 2010503496 A | 2/2010 |
| JP | 2010511467 A | 4/2010 |
| JP | 2011137025 A | 7/2011 |
| JP | 2012510332 A | 5/2012 |
| JP | 2012515018 | 7/2012 |
| JP | 2012515018 A | 7/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 4/2004 |
| WO | 9104014 A1 | 4/1991 |
| WO | 9614238 | 5/1996 |
| WO | 9634571 A1 | 11/1996 |
| WO | 9810745 A1 | 3/1998 |
| WO | 9814238 A1 | 4/1998 |
| WO | 9901076 A1 | 1/1999 |
| WO | 9904710 A1 | 2/1999 |
| WO | 0020554 A | 4/2000 |
| WO | 0110319 A1 | 2/2001 |
| WO | 2001048153 A1 | 7/2001 |
| WO | 0170114 A1 | 9/2001 |
| WO | 0200554 A1 | 1/2002 |
| WO | 02078527 A2 | 10/2002 |
| WO | 02089686 A1 | 11/2002 |
| WO | 02100459 A2 | 12/2002 |
| WO | 2003020144 A1 | 3/2003 |
| WO | 2003047684 A2 | 6/2003 |
| WO | 03099382 A1 | 12/2003 |
| WO | 2004008153 | 1/2004 |
| WO | 2004080347 A2 | 9/2004 |
| WO | 2005065284 A2 | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2007137303 A2 | 11/2007 |
| WO | 2008034103 A3 | 3/2008 |
| WO | 2008063195 A1 | 5/2008 |
| WO | 2008101086 A2 | 8/2008 |
| WO | 2008101091 A2 | 8/2008 |
| WO | 2009036468 A1 | 3/2009 |
| WO | 2009046176 A1 | 4/2009 |
| WO | 2009134876 A1 | 11/2009 |
| WO | 2009135070 A1 | 11/2009 |
| WO | 2009137800 A2 | 11/2009 |
| WO | 2010015592 | 2/2010 |
| WO | 2010064154 A1 | 6/2010 |
| WO | 2010080974 A1 | 7/2010 |
| WO | 2010085765 | 7/2010 |
| WO | 2010117806 A1 | 10/2010 |
| WO | 2010118387 A | 10/2010 |
| WO | 2010128373 | 11/2010 |
| WO | 2010132472 A1 | 11/2010 |
| WO | 2010151277 A1 | 12/2010 |
| WO | 2011028937 | 3/2011 |
| WO | 2011047387 A | 4/2011 |
| WO | 2011047387 A2 | 4/2011 |
| WO | 2011062653 A1 | 5/2011 |
| WO | 2011072221 A1 | 6/2011 |
| WO | 2011135294 A1 | 11/2011 |
| WO | 2012006533 A1 | 1/2012 |
| WO | 2012051433 A2 | 4/2012 |
| WO | 2012054560 A1 | 4/2012 |
| WO | 2012054573 A2 | 4/2012 |
| WO | 2012063266 | 5/2012 |
| WO | 2012071526 A | 5/2012 |
| WO | 2012071526 A2 | 5/2012 |
| WO | 2012088149 A | 6/2012 |
| WO | 2012088149 A2 | 6/2012 |
| WO | 2012140376 | 10/2012 |
| WO | 2013052138 | 4/2013 |
| WO | 2013176881 | 11/2013 |
| WO | 2014039320 | 3/2014 |
| WO | 2015175570 A1 | 11/2015 |
| WO | 2015192027 A1 | 12/2015 |
| WO | 2016100325 A1 | 6/2016 |
| WO | 2016164930 A1 | 10/2016 |
| WO | 2017024123 A1 | 2/2017 |
| WO | 2017117418 A1 | 7/2017 |
| WO | 2020061192 A1 | 3/2020 |
| WO | 2022066768 A1 | 3/2022 |
| WO | 2023172773 A1 | 9/2023 |

OTHER PUBLICATIONS

Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).

(56) References Cited

OTHER PUBLICATIONS

Sersa, et al, Tumor blood flow modifying effect of electrochemotherapy with Bleomycin, Anticancer Research, 1999, 19, pp. 4017-4022.
Shafiee, et al, A preliminary study to delineate irreversible electroporation from thermal damage using the Arrhenius equation, Journal of Biomedical Engineering, Jul. 2009, vol. 131, 074509, pp. 1-5.
Shao, Qi et al. Engineering T cell response to cancer antigens by choice of focal therapeutic conditions, International Journal of Hyperthermia, 2019, DOI: 10.1080/02656736.2018.1539253.
Sharma, A., et al., "Review on Thermal Energy Storage with Phase Change Materials and Applications", Renewable Sustainable Energy Rev. 13(2), 318-345 (2009).
Soden, et al, Successful application of targeted electrochemotherapy using novel flexible electrodes and low dose bleomycin to solid tumors, Cancer Letters, 2006, 232 pp. 300-310.
Son, et al, Basic features of a cell electroporation model: illustrative behavior for tw overy different pulses, J Membrane Biol, Jul. 22, 2014, 247, pp. 1209-1228.
Song, Z.Q., et al., Mechanisms for steep pulse irreversible electroporation technology to kill human large cell lung cancer cells L9981. International Journal of Clinical and Experimental Medicine, 2014. 7(8): p. 2386-2394.
Szot et al., "3D in vitro bioengineered tumors based on collagen I hydrogels." Biomaterials vol. 32, pp. 7905-7912 (2011).
Talele, S. and P. Gaynor, "Non-linear time domain model of electropermeabilization: Effect of extracellular conductivity and applied electric field parameters", Journal of Electrostatics,66(5-6): p. 328-334 (2008).
Talele, S. and P. Gaynor, "Non-linear time domain model of electropermeabilization: Response of a single cell to an arbitrary applied electric field", Journal of Electrostatics, 65(12): p. 775-784 (2007).
Talele, S., et al., "Modelling single cell electroporation with bipolar pulse parameters and dynamic pore radii". Journal of Electrostatics, 68(3): p. 261-274 (2010).
Teissie, J. and T.Y. Tsong, "Electric-Field Induced Transient Pores in Phospholipid-Bilayer Vesicles". Biochemistry, 20(6): p. 1548-1554(1981).
Tekle, et al., "Electroporation by using bipolar oscillating electric field: An improved method for DNA transfection of NIF 3T3 cells," Proc. Natl. Acad. Sci., Biochemistry, vol. 88, pp. 4230-4234, May 1991.
Thomson, Human experience with irreversible electroporation, Irreversible Electroporation, Biomed, 2010, pp. 249-354.
Thomson, K. R., et al., "Investigation of the Safety of Irreversible Electroporation in Humans" J. Vascular Int. Radiol. 22(5), 611-621 (2011).
Tibbitt et al., "Hydrogels as Extracellular Matrix Mimics for 3D Cell Culture", Jul. 2009, Biotechnol Bioeng, 103(4),655-663.
Tijink, et al, How we do it: Chemo-electroporation in the head and neck for otherwise untreatable patients, Correspondence, Clinical Otolaryngology, 2006, 31, pp. 447-451.
Tracy, et al, Irreversible electroporation (IRE): A novel method for renal tissue ablation, BJU International, 107, pp. 1982-1987.
Trimmer, et al, Minimally invasive percutaneous treatment of small renal tumors with irreversible electroporation: a single-center experience, J Vasc Intery Radiol, 2015, 26: pp. 1465-1471.
Troszak, et al., Self-powered electroporation using a singularity-induced nano-electroporation configuration, Biochemical and Biophysical Research Communications, Sep. 28, 2011, 414, pp. 419-424.
Tsivian, Polascik, Recent advances in focal therapy of prostate and kidney cancer, Medicine Reports, Jan. 18, 2010, 2, 1, pp. 1-3.
Valdez, C. M. et al., The interphase interval within a bipolar nanosecond electric pulse modulates bipolar cancellation, Bioelectromagnetics, vol. 39, No. 6,441-450, 2018, 28 pages.
Van Den Bos, W. et al., "MRI and contrast-enhanced ultrasound imaging for evaluation offocal irreversible electroporation treatment: results from a phase i-ii study in patients undergoing ire followed by radical prostatectomy," European radiology, vol. 26, No. 7, pp. 2252-2260, 2016.
Verbridge et al., "Oxygen-Controlled Three-Dimensional Cultures to Analyze Tumor Angiogenesis." Tissue Engineering, Part A vol. 16, pp. 2133-2141 (2010).
Verma, A. et al., "Primer on Pulsed Electrical Field Ablation: Understanding the Benefits and Limitations," Circ. Arrhythmia Electrophysiol., No. September, pp. 1-16,2021,16 pages.
Vernier, P.T., et al., "Nanoelectropulse-driven membrane perturbation and small molecule permeabilization", Bmc Cell Biology, 7 (2006).
Vižintin, A. et al., "Effect of interphase and interpulse delay in high-frequency irreversible electroporation pulses on cell survival, membrane permeabilization and electrode material release," Bioelectrochemistry, vol. 134, Aug. 2020,14 Pages.
Voyer, D., A. Silve, L. M. Mir, R. Scorretti, and C. Poignard, "Dynamical modeling of tissue electroporation," Bioelectrochemistry, vol. 119, pp. 98-110, 2018.
Wandel, A. et al. "Optimizing Irreversible Electroporation Ablation with a Bipolar Electrode," Journal of Vascular and Interventional Radiology, vol. 27, Issue 9, 1441-1450.e2, 2016.
Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional ntracellular effects are expected." Bioelectrochemistry vol. 87, pp. 236-243 (2012).
Weaver, J. C., Electroporation of biological membranes from multicellular to nano scales, IEEE Tms. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011) 2 pages.
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.
Wittkampf, et al, Myocardial lesion depth with circular electroporation ablation, Circ Arrhythm Electrophysiol, 2012, 5, pp. 581-586.
Wood et al., Technologies for Guidance of Radiofrequency Ablation in the Multimodality Interventional Suite of the Future, Jan. 2007, National Institutes of Health, pp. 1-26.
Wright, On a relationship between the arrhenius parameters from thermal damage studies, Technical Brief, Journalof Biomechanical Engineering, Transactions of the ASME, Apr. 2003, vol. 125, pp. 300-304.
Yang et al., "Dielectric properties of human leukocyte subpopulations determined by selectrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Yarmush, M. L. et al., "Electroporation-Based Technologies for Medicine: Principles, Applications, and Challenges," Annu. Rev. Biomed. Eng., vol. 16, No. 1,295-320, 2014, 29 pages.
Ybarra, Gary A, et al. "Breast Imaging using Electrical Impedance Tomography." in Suri, J.S., R.M. Rangayyan, and S. Laxminarayan, Emerging Technologies in Breast Imaging and Mammography2008: American Scientific Publishers.
Zhang, et al, MR imaging to assess immediate response to irreversible electroporation for targeted ablation of liver tissues: Preclinical feasibility studies in a rodent model, Radiology, Aug. 2010, vol. 256, No. 2, pp. 424-432.
Zhao, J. et al. "Irreversible electroporation reverses resistance to immune checkpoint blockade in pancreatic cancer", Nature Communications (2019) 10:899,14 pages.
Zhao, Y., S. Bhonsle, S. Dong, Y. Lv, H. Liu, A. Safaai-Jazi, R. V. Davalos, and C. Yao, "Characterization of conductivity changes

(56) References Cited

OTHER PUBLICATIONS during high-frequency irreversible electroporation for treatment planning," IEEE Transactions on Biomedical Engineering, vol. 65, No. 8, pp. 1810-1819,2017.
Zhou, et al, Electroporation-mediated transfer of plasmids to the lung results in reduced TLR9 signaling and Inflammation, Gene Therapy, Mar. 8, 2007, 14, pp. 775-780.
Kinosita, Jr., et al., Formation and resealing of pores of controlled sizes in human erythrocyte membrane, Aug. 1977, vol. 268, pp. 438-441.
Kirson et al., "Alternating electric fields arrest cell proliferation in animal tumor models and human brain tumors." Proceedings of the National Academy of Sciences vol. 104, pp. 10152-10157 (2007).
Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.
Kolb, J.F., et al., "Nanosecond pulsed electric field generators for the study of subcellular effects", Bioelectromagnetics, 27(3): p. 172-187 (2006).
Kotnik and Miklavcic, "Theoretical evaluation of voltage inducement on internal membranes of biological cells exposed o electric fields." Biophysical Journal, vol. 90(2), pp. 480-491 (2006).
Kotnik et al., "Sensitivity of transmembrane voltage induced by applied electric fields—A theoretical analysis", Bioelectrochemistry and Bioenergetics, vol. 43, Issue 2, 1997, pp. 285-291.
Kotnik, T. and D. Miklavcic, "Theoretical evaluation of the distributed power dissipation in biological cells exposed to electric fields", Bioelectromagnetics, 21(5): p. 385-394 (2000).
Kotnik, T., et al., "Cell membrane electropermeabilization by symmetrical bipolar rectangular pulses". Part I. Increased efficiency of permeabilization. Bioelectrochemistry, 54(1): p. 83-90 (2001).
Kotnik, T., et al., "Role of pulse shape in cell membrane electropermeabilization", Biochimica Et Biophysica Acta-iomembranes, 1614(2): p. 193-200 (2003).
Kotnik, T., et al., "Cell membrane electropermeabilization by symmetrical bipolar rectangular pulses. Part II. Reduced electrolytic contamination", Bioelectrochemistry, 54(1): p. 91-95 (2001).
Kranjc, M., S. Kranjc, F. Bajd, G. Sersa, I. Sersa, and D. Miklavčič, "Predicting irreversible electroporation-induced tissue damage by means of magnetic resonance electrical impedance tomography," Scientific reports, vol. 7, No. 1, pp. 1-10, 2017.
Kroeger, et al, Curvature-driven pore growth in charged membranes during charge-pulse and voltage-clamp experiments, Biophysical Journal, Feb. 2009, 96, 3, pp. 907-916.
Kurup, et al, Image-Guided Percutaneous Ablation of Bone and soft Tissue Tumors, Semin Intervent Radiol 2010, 27:276-284.
Labeed et al., "Differences in the biophysical properties of membrane and cytoplasm of apoptotic cells revealed using dielectrophoresis." Biochimica et Biophysica Acta (BBA)—General Subjects, vol. 1760, pp. 922-929 (2006).
Lackovic, I., et al., "Three-dimensional Finite-element Analysis of Joule Heating in Electrochemotherapy and in vivo Gene Electrotransfer", Ieee Transactions on Dielectrics and Electrical Insulation, 16(5): p. 1338-1347 (2009).
Laufer, et al., Electrical impedance characterization of normal and cancerous human hepatic tissue, Physiological Measurement, vol. 31, pp. 995-1009 (2010).
Lavee, et al., "A Novel Nonthermal Energy Source for Surgical Epicardial Atrial Ablation: Irreversible Electroporation," The Heart Surgery Forum #2006-1201, vol. 10 (2): 96-101 (2007).
Lebar et al., "Inter-pulse interval between rectangular voltage pulses affects electroporation threshold of artificial lipid bilayers." IEEE Transactions on Nano Bioscience, vol. 1 (2002) pp. 116-120.
Lee, Cassinian Oval, Nov. 2004, Mathematics Department of the University of California at Irvine, pp. 1-5.
Lee, E. W. et al. Advanced Hepatic Ablation Technique for Creating Complete Cell Death : Irreversible Electroporation. Radiology 255, 426-433, doi:10.1148/radiol. 10090337 (2010).

Lee, et al, Imaging guided percutaneous irreversible electroporation: Ultrasound and immunohistological correlation, Technology in Cancer Research and Treatment, Aug. 2007, vol. 6, No. 4, pp. 287-293.
Lee, et al, Irreversible electroporation: A novel image-guided cancer therapy, Gut and Liver, Sep. 2010, vol. 4, Supp. 1, pp. S99-S104.
Lee, R. C., D. J. Canaday, and S. M. Hammer. Transient and stable ionic permeabilization of isolated skeletal muscle cells after electrical shock. J. Burn Care Rehabil. 14:528-540,1993.
Li, et al, The effects of irreversible electroporation (IRE) on nerves, PLOS One, Apr. 14, 2011, vol. 6, Iss. 4, e18831, pp. 1-7.
Lin, et al., An optically induced cell lysis device using dielectrophoresis, Applied Physics Letters, Jan. 20, 2009, 94, 033901, pp. 1-3.
Lion, et al, Poly(I:C) enhances the susceptibility of leukemic cells to NK cell cytotoxicity and phagocytosis by DC, PLOS One, vol. 6, Iss. 6, e20952, pp. 1-10, Jun. 17, 2011.
Long, G., et al., "Targeted Tissue Ablation With Nanosecond Pulses", Ieee Transactions on Biomedical Engineering, 58(8) (2011).
Lu, et al, Irreversible electroporation: Ready for prime time?, Techniques in Vascular and Interventional Radiology, 2013, 16, pp. 277-286.
Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).
M. Marty et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, pp. 3-13, 2006.
Macek Lebar and Miklavcic, "Cell electropermeabilization to small molecules in vitro: control by pulse parameters." Radiology and Oncology, vol. 35(3), pp. 193-202 (2001).
Machado-Aranda, et al, Gene transfer of the Na+, K+K-ATPase B1 subunit using electroporation increases lung liquid clearance, American Journal of Respiratory and Critical Care Medicine, 2004, vol. 171, pp. 204-211.
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
Mahmood, F., et al., "Diffusion-Weighted MRI for Verification of Electroporation-Based Treatments", Journal of Membrane Biology 240:131-138 (2011).
Mahmood, Gehl, Optimizing clinical performance and geometrical robustness of a new electrode device for ntracranial tumor electroporation, Bioelectrochemistry, Jan. 6, 2011, 81, pp. 10-16.
Mahnic-Kalamiza, et al., "Educational application for visualization and analysis of electric field strength in multiple electrode electroporation," BMC Med Educ, vol. 12:102,13 pages, 2012.
Mali, et al., "The Effect of Electroporation Pulses on Functioning of the Heart," Med Biol Eng Comput (2008) 46:745-757.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech, in Cancer Res. and Treatment, vol. 6, No. 4, Aug. 2007, pp. 307-312.
Maor, et al, Intravascular irreversible electroporation: Theoretical and experimental feasibility study, 30th Annual International IEEE EMBS Conference, IEEE, Aug. 20, 2008, pp. 2051-2054.
Maor, et al, Irreversible electroporation attenuates neointimal formation after angioplasty, IEEE Transactions on Biomedical Engineering, Sep. 2008, vol. 55, No. 9, pp. 2268-2274.
Maor, et al., Non Thermal Irreversible Electroporation: Novel Technology for Vascular Smooth Muscle Cells Ablation, PLoS One, Mar. 2009, 4(3): p. e4757, 9 pages.
Maor, Rubinsky, Endovascular nonthermal irreversible electroporation: A finite element analysis, Journal of Biomedical Engineering, Feb. 7, 2010, vol. 132, 031008, pp. 1-7.
Marszalek et al., "Schwan equation and transmembrane potential induced by alternating electric field." Biophysical Journal, vol. 58, pp. 1053-1058 (1990).
Martin et al., "Gene Transfer to Intact Mesenteric Arteries by Electroporation" Journal of Vascular Research, 37:372-380 (2000).

(56) References Cited

OTHER PUBLICATIONS

Martin, n.R.C.G., et al., "Irreversible electroporation therapy in the management of locally advanced pancreatic adenocarcinoma." Journal of the American College of Surgeons, 2012.215(3): p. 361-369.

Martinsen, O. G. and Grimnes, S., Bioimpedance and bioelectricity basics. Academic press, 2011.

Maybody, An Overview of Image-Guided Percutaneous Ablation of Renal Tumors, Seminars in Interventional Radiology/vol. 27, No. 3, 2010, pp. 261-267.

Mazurek, et al, Effect of Short HV Pulses in Bacteria and Fungi, 1995, vol. 2, No. 3, pp. 418-425.

McCall, Nanoknife, liposomal doxorubicin show efficacy against liver cancer, European Congress of Radiology, Mar. 1, 2011, pp. 1-2.

Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).

Adeyanju, et al, The improvement of irreversible electroporation therapy using saline-irrigated electrodes: A theoretical study, Technology in Cancer Research and Treatment, Aug. 2011, vol. 10, No. 4, pp. 347-360.

Agerholm-Larsen, B., et al., "Preclinical Validation of Electrochemotherapy as an Effective Treatment for Brain Trumors", Cancer Research 71: 3753-3762 (2011).

Al-Khadra, et al, The role of electroporation in defibrillation, Circulation Research, Oct. 27, 2000, 87, pp. 797-804.

Al-Sakere et al., "Tumor ablation with irreversible electroporation." PLoS One, Issue 11, e1135, 8 pages, 2007.

Al-Sakere, et al, A study of the immunological response to tumor ablation with irreversible electroporation, Technology in Cancer Research and Treatment, Aug. 2007, vol. 6, No. 4, pp. 301-305.

Albright, et al, Performance and complicatioins associated with the Synchromed 10-ml infusion pump for intrathecal baclofen administration in children, J Neurosurg (Pediatrics 2), Aug. 2004, vol. 101, pp. 64-68.

Alinezhadbalalami, N. et al., "Generation of Tumor-activated T cells Using Electroporation", Bioelectrochemistry 142 (2021) 107886, Jul. 13, 2021, 11 pages.

Appelbaum et al., "US Findings after Irreversible Electroporation Ablation: Radiologic-Pathologic Correlation," Radiology, 262, pp. 117-125, Jan. 1, 2012.

Arena et al. "High-Frequency Irreversible Electroporation (H-FIRE) for Non-thermal Ablation without Muscle Contraction." Biomed. Eng. Online, vol. 10, 20 pages (2011).

Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.

Arena, C.B., et al., "A three-dimensional in vitro tumor platform for modeling therapeutic irreversible electroporation." Biophysical Journal, 2012.103(9): p. 2033-2042.

Arena, Christopher B., et al.,"Phase Change Electrodes for Reducing Joule Heating During Irreversible Electroporation". Proceedings of the ASME 2012 Summer Bioengineering Conference, SBC2012, Jun. 20-23, 2012, Fajardo, Puerto Rico.

Arena, et al, Theoretical considerations of tissue electropration with high frequency biopolar pulses, IEEEE, pp. 1-7, (2010).

Arena, et al, Towards the development of latent heat storage electrodes for electroporation-based therapies, Applied Physics Letters, 2012, 101, 083902, pp. 1-4.

Asami et al., "Dielectric properties of Aouse lyAphocytes and erythrocytes." BiochiAica et Biophysica Acta (BBA)—Molecular Cell Research, 1010 (1989) pp. 49-55.

Bolland, F., et al., "Development and characterisation of a full-thickness acellular porcine bladder matrix for tissue engineering", Biomaterials, Elsevier Science Publishers, Barking, GB, vol. 28, No. 6,Nov. 28, 2006, pp. 1061-1070.

Bagla, S. and Papadouris, D., "Percutaneous Irreversible Electroporation of Surgically Unresectable Pancreatic Cancer: A Case Report" J. Vascular Int. Radiol. 23(1), 142-145 (2012).

Ball, et al, Irreversible electroporation: A new challenge in "out of the operating theater" anesthesia, Anesth Analg, May 2010, 110, pp. 1305-1309.

Bancroft, et al., Design of a Flow Perfusion Bioreactor SysteA for Bone Tissue-Engineering Applications, Tissue Engineering, vol. 9, No. 3, 2003, p. 549-554.

Baptista et al., "The Use of Whole Organ Decellularization for the Generation of a Vascularized Liver Organoid," Heptatology, vol. 53, No. 2, pp. 604-617 (2011).

Bayazitoglu, et al, An overview of nanoparticle assisted laser therapy, International Journal of Heat and Mass Transfer, Sep. 11, 2013, 67, pp. 469-486.

Beebe, S.J., et al., "Diverse effects of nanosecond pulsed electric fields on cells and tissues", DNA and Cell Biology, 22(12): 785-796(2003).

Beebe, S.J., et al.,, "Nanosecond, high-intensity pulsed electric fields induce apoptosis in human cells", FASEB J, 17(9): p. 1493-5 (2003).

Beitel-White, N., S. Bhonsle, R. Martin, and R. V. Davalos, "Electrical characterization of human biological tissue or irreversible electroporation treatments," in 2018 40th Annual International Conference of the IEEE Engineering in Medicine and Biology Society (EMBC). IEEE, 2018, pp. 4170-4173.

Belehradek, J., et al., "Electropermeabilization of Cells in Tissues Assessed by the Qualitative and Quantitative Electroloading of Bleomycin", Biochimica Et Biophysica Acta—Biomembranes, 1190(1): p. 155-163 (1994).

Ben-David, E. et al., "Irreversible Electroporation: Treatment Effect is Susceptible to Local Environment and Tissue Properties," Radiology, vol. 269, No. 3, 2013, 738-747.

Ben-David, E.,et al., "Characterization of Irreversible Electroporation Ablation in In Vivo Procine Liver" Am. J. Roentgenol. 198(1), W62-W68 (2012).

Benz, R., et al. "Reversible electrical breakdown of lipid bilayer membranes: a charge-pulse relaxation study". J Membr Biol, 48(2): p. 181-204 (1979).

Bertacchini, et al, Design of an irreversible electroporation system for clinical use, Technology in Cancer Research and Treatment, Aug. 2007, vol. 6, No. 4, pp. 313-320.

Bhonsle, S. et al., "Characterization of Irreversible Electroporation Ablation with a Validated Perfused Organ Model," J. Vase. Interv. Radiol., vol. 27, No. 12, pp. 1913-1922.e2, 2016.

Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.

Bhonsle, S., M. F. Lorenzo, A. Safaai-Jazi, and R. V. Davalos, "Characterization of nonlinearity and dispersion in issue impedance during high-frequency electroporation," IEEE Transactions on Biomedical Engineering, vol. 65, No. 10, pp. 2190-2201,2018.

Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.

Bondarenko, A. and G. Ragoisha, Eis spectrum analyser (the program is available online at http://www.abc.chemistry.bsu.by/vi/analyser/.

Boone, et al, Review imaging with electricity: Report of the European concerted action on impedance tomography, Journal of Medical Engineering & Technology, Nov. 1997, vol. 21, No. 6, pp. 201-232.

Boussetta, N., N. Grimi, N. I. Lebovka, and E. Vorobiev, "Cold" electroporation in potato tissue induced by pulsed electric field, Journal of food engineering, vol. 115, No. 2, pp. 232-236,2013.

Bower et al., "Irreversible electroporation of the pancreas: definitive local therapy without systemic effects." Journal of surgical oncology, 2011.104(1): p. 22-28.

Buist et al., "Efficacy of multi-electrode linear irreversible electroporation," Europace, vol. 23, No. 3, pp. 464-468, 2021, 5 pages.

Bulvik, B. E. et al. "Irreversible Electroporation versus Radiofrequency Ablation: A Comparison of Local and Systemic Effects in a Small Animal Model," Radiology, vol. 280, No. 2, 2016,413-424.

(56) References Cited

OTHER PUBLICATIONS

Butikofer, R. et al., "Electrocutaneous Nerve Stimulation-I: Model and Experiment," IEEE Trans. Biomed. Eng., vol. BME-25, No. 6, 526-531, 1978,6 pages.
Butikofer, R. et al., "Electrocutaneous Nerve Stimulation-II: Stimulus Waveform Selection," IEEE Trans. Biomed. Eng., vol. BME-26, No. 2, 69-75, 1979.
Cannon et al., "Safety and early efficacy of irreversible electroporation for hepatic tumors in proximity to vital structures." Journal of Surgical Oncology, 6 pages (2012).
Carmi, and Georgiades, Combination percutaneous and intraarterial therapy for the treatment of hepatocellular carcinoma: A review, Seminars in Interventional Radiology, 2010, vol. 27, No. 3, pp. 296-301.
Carpenter A.E. et al., "CellProfiler: image analysis software for identifying and quantifying cell phenotypes." Genome Biol. 2006; 7(10): R100. Published online Oct. 31, 2006,11 pages.
Castellvi, Q., B. Mercadal, and A. Ivorra, "Assessment of electroporation by electrical impedance methods," in Handbook of electroporation. Springer-Verlag, 2016, pp. 671-690.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chang, D.C., "Cell Poration and Cell-Fusion Using an Oscillating Electric-Field". Biophysical Journal, 56(4): p. 641-652(1989).
Charpentier, et al, Irreversible electroporation of the liver an dliver hilum in swine, HBP, 2011, 13, pp. 168-173.
Charpentier, K.P., et al., "Irreversible electroporation of the pancreas in swine: a pilot study." HPB: the official journal of the International Hepato Pancreato Biliary Association, 2010.12(5): p. 348-351.
PCT Application No. PCT/US2011/062067, International Search Report and Written Opinion dated Jul. 25, 2012.
PCT Application No. PCT/US2011/066239, International Search Report (dated Aug. 22, 2012), and Written Opinion (dated Aug. 22, 2012).
PCT International Search Report and Written Opinion from PCT/US2010/053077, dated Aug. 2, 2011.
PCT International Search Report for PCT/US10/29243 dated Jul. 30, 2010, 4 pages.
Pech, et al, Irreversible electroporation of renal cell carcinoma: A first-in-man phase I clinical study, Cardiovasc Intervent Radiol, Aug. 15, 2010.
Persichetti F et al, "Normal and Expanded Huntington's Disease Gene Alleles Produce Distinguishable Proteins Due to Translation Across the CAG Repeat", Molecular Medicine, Feinstein Institute for Medical Research, Washington, DC; US, (May 1, 1995), vol. 1, No. 4, ISSN 1076-1551, pp. 374-383, XP000997528.
Philips, IntelliVue Patient Monitor, Jan. 2008, Philips, pp. 1-532 (Year: 2008).
Phillips, et al, Irreversible electroporation on the small intestine, British Journal of Cancer, 2012, pp. 1-6.
Phillips, et al, Nonthermal irreversible electroporation for tissue decellularization, Journal of Biomedical Engineering, Aug. 16, 2010, vol. 132, 091003, pp. 1-8.
Polajzer, T. et al., "Cancellation effect is present in high-frequency reversible and irreversible electroporation," Bioelectrochemistry, vol. 132, 2020, 11 pages.
Polak, et al, On the electroporation thresholds of lipid bilayers: Molecular dynamics simulation investigations, J Membrane Biol, Jun. 13, 2013, 246, pp. 843-850.
Pucihar et al., "Numerical determination of transmembrane voltage induced on irregularly shaped cells." Annals of Biomedical Engineering, vol. 34, pp. 642-652 (2006).
Qiao et al. Electrical properties of breast cancer cells from impedance measurement of cell suspensions, 2010, Journal of Physics, 224, 1-4 (2010).

Radeva, et al, Induction of apoptosis and necrosis in cancer cells by electric fields, electromagnetic fields, and photodynamically active quinoids, Electromagnetic Biology and Medicine, 2003, 23, pp. 185-200.
Rajagopal, V. and S.G. Rockson, Coronary restenosis: a review of mechanisms and management, The American Journal of Medicine, 2003, 115(7): p. 547-553.
Rebersek, et al., Advantages and disadvantages of different concepts of electroporation pulse generation, Automatika, 2011, 52, 1, pp. 12-19.
Reilly, J. P. et al., "Sensory Effects of Transient Electrical Stimulation-Evaluation with a Neuroelectric Model," IEEE Trans. Biomed. Eng., vol. BME-32, No. 12, 1001-1011, 1985, 11 pages.
Ringel-Scaia, V. M. et al., High-frequency irreversible electroporation is an effective tumor ablation strategy that induces immunologic cell death and promotes systemic anti-tumor immunity. EBioMedicine, 2019,44,112-125.
Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
Rowland, et al, Transvenous ablation of atrioventricular conduction with a low energy power source, Br Heart J, 1989, 62, pp. 361-366.
Rubinsky, B., "Irreversible Electroporation in Medicine", Technology in Cancer Research and Treatment, vol. 6, No. 4, Aug. 1, 2007, pp. 255-259.
Rubinsky, et al, Optimal parameters for the destruction of prostate cancer using irreversible electroporation, The Journal of Urology, Dec. 2008, vol. 180, pp. 2668-2674.
Rubinsky, L. et al., "Electrolytic Effects During Tissue Ablation by Electroporation," Technol. Cancer Res. Treat., vol. 15, No. 5, NP95-103, 2016, 9 pages.
Sabuncu, et al, Dielectrophoretic separation of mouse melanoma clones, Biomicrofluidics, Jun. 16, 2010, 4, 021101, pp. 1-7.
SAI Infusion Technologies, "Rabbit Ear Vein Catheters", https://www.sai-infusion.com/products/rabbit-ear-catheters, Aug. 10, 2017 webpage printout, 5 pages.
Saldanha, et al, Current tumor ablation technologies: Basic science and device review, Seminars in Interventional Radiology, 2010, vol. 27, No. 3, pp. 247-254.
Salford, L.G., et al., "A new brain tumour therapy combining bleomycin with in vivo electropermeabilization", Biochem. Biophys. Res. Commun., 194(2): 938-943 (1993).
Salmanzadeh et al., "Investigating dielectric properties of different stages of syngeneic murine ovarian cancer cells" Biomicrofiuidics 7, 011809 (2013), 12 pages.
Salmanzadeh et al., "Sphingolipid Metabolites Modulate Dielectric Characteristics of Cells in a Mouse Ovarian Cancer Progression Model." Integr. Biol., 5(6). pp. 843-852 (2013).
Salmanzadeh et al.,"Dielectrophoretic differentiation of mouse ovarian surface epithelial cells, macrophages, and fibroblasts using contactless dielectrophoresis." Biomicrofluidics, vol. 6,13 Pages (2012).
Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.
Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601,2011.

(56) References Cited

OTHER PUBLICATIONS

Sanders, et al., Nanosecond pulse generator with scalable pulse amplitude, IEEE, 2008, pp. 65-68.
Sankaranarayanan, et al, Effect of irreversible electroporation on cell proliferation in fibroblasts, Proc. ESA Annual Meeting on Electrostatics, 2011, pp. 1-8.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort cancer Cells from Dilute Whole Blood Samples." Biosensors & Bioelectronics, 8 pages (2011).
Sano et al., "Contactless Dielectrophoretic Spectroscopy: Examination of the Dielectric Properties of Cells Found in Blood." Electrophoresis, 32, pp. 3164-3171, 2011.
Sano, et al, Towards the creation of decellularized organ constructs using irreversible electroporation and active mechanical perfusion, Biomedical Engineering Online, 2010, 9, 83, pp. 1-16.
Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. interv. Radiol., vol. 29, No. 6, 893-898.e4, Jun. 2018, 18 pages.
Sano, M. B. et al., "Burst and continuous high frequency irreversible electroporation protocols evaluated in a 3D tumor Model," Phys. Med. Biol., vol. 63, No. 13, 2018,17 pages.
Saur et al., "CXCR4 expression increases liver and lung metastasis in a mouse model of pancreatic cancer." Gastroenterology, vol. 129, pp. 1237-1250 (2005).
Savader, et al."Treatment of Hemodialysis Catheter-associated Fibrin Sheaths by rt-PA Infusion: Critical Analysis of 124 Procedures," J Vasc Intery Radiol 2001; 12:711-715.
Schoenbach et al., "Intracellular effect of ultrashort electrical pulses." Bioelectromagnetics, 22 (2001) pp. 440-448.
Schoenbach, et al, Bioelectric effects of intense nanosecond pulses, IEEE Transactions on Dielectric and Electrical Insulation, 2007, vol. 14, Iss. 5, pp. 1088-1109.
Seibert et al., "Clonal variation of MCF-7 breast cancer cells in vitro and in athymic nude mice." Cancer Research, vol. 13, pp. 2223-2239 (1983).
Seidler et al., "A Cre-IoxP-based mouse model for conditional somatic gene expression and knockdown in vivo by using avian retroviral vectors." Proceedings of the National Academy of Sciences, vol. 105, pp. 10137-10142 (2008).
Chen et al., "Classification of cell types using a microfluidic device for mechanical and electrical measurement on single cells." Lab on a Chip, vol. 11, pp. 3174-3181 (2011).
Chen, et al, Preclinical study of locoregional therapy of hepatocellular carcinoma by bioelectric ablation with microsecond pulsed electric fields (usPEFs), Scientific Reports, Apr. 2015, 5, 9851, pp. 1-10.
Chen, M.T., et al., "Two-dimensional nanosecond electric field mapping based on cell electropermeabilization", PMC Biophys, 2(1):9 (2009).
Choi, et al, Preclinical analysis of irreversible electroporation on rat liver tissues using a microfabricated electroporator, Tissue Engineering Part C, 2010, vol. 16, No. 6, pp. 1245-1253.
Clark et al., "The electrical properties of resting and secreting pancreas." The Journal of Physiology, vol. 189, pp. 247-260 (1967).
Corovic, et al, Analytical and numerical quantification and comparison of the local electric field in the tissue for different electrode configurations, BioMedical Engineering Online, Oct. 15, 2007, 6, 37, pp. 1-14.
Cosman, E. R. et al., "Electric and Thermal Field Effects in Tissue Around Radiofrequency Electrodes," Pain Med., vol. 6, No. 6, 405-4124, 2005, 20 pages.

Craiu, Scadden, Chapter 22 flow electroporation with pulsed electric fields for purging tumor cells, Electroporation Protocols: Preclinical and Clinical Gene Medicine, Methods in Molecular Biology, vol. 423, 2008, pp. 301-310.
Creason, S. O, J. W. Hayes, and D. E. Smith, "Fourier transform faradaic admittance measurements iii. comparison pf measurement efficiency for various test signal waveforms," Journal of Electroanalytical chemistry and interfacial electrochemistry, vol. 47, No. 1, pp. 9-46,1973.
Cukjati, et al, Real time electroporation control for accurate and safe in vivo non-viral gene therapy, Bioelectrochemistry, Nov. 10, 2006, 70, pp. 501-507.
Dahl et al., "Nuclear shape, mechanics, and mechanotransduction." Circulation Research vol. 102, pp. 1307-1318 (2008).
Daniels, Rubinsky, Electrical field and temperature model of nonthermal irreversible electroporation in heterogeneous tissues, Journal of Biomedical Engineering, Jul. 2009, vol. 131, 071006, pp. 1-12.
Daniels, Rubinsky, Temperature modulation of electric fields in biological matter, PLOS One, vol. 6, Iss. 6, e20877, pp. 1-9, Jun. 2011.
Daskalov, I., et al, "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase 1 Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
De Senneville, B. D. et al., "MR thermometry for monitoring tumor ablation," European radiology, vol. 17, No. 9, pp. 2401-2410, 2007.
De Vuyst, E., et al., "In situ bipolar Electroporation for localized cell loading with reporter dyes and investigating gap functional coupling", Biophysical Journal, 94(2): p. 469-479 (2008).
Demirbas, M. F., "Thermal Energy Storage and Phase Change Materials: An Overview" Energy Sources Part B 1(1), 35-95 (2006).
Deodhar, et al, Irreversible electroporation near the heart: Ventricular arrhythmias can be prevented with ECG synchronization, AJR, Mar. 2011, 196, pp. W330-W335.
Deodhar, et al, Renal tissue ablation with irreversible electroporation: Preliminary results in a porcine model, Technology and Engineering, Urology, 2010, 1-7.
Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.
Diederich, et al, Catheter-based ultrasound applicators for selective thermal ablation: progress towards MRI-guided applications in prostate, Int. J. Hyperthermia, Nov. 2004, vol. 20, No. 7, pp. 739-756.
Du Pre, et al, Minimal coronary artery damage by myocardial electroporation ablation, European Society of Cardiology, Europace, May 31, 2012, pp. 1-6.
Duck, F. A., Physical Properties of Tissue: A Comprehensive Reference Book. London: Harcourt Brace Jovanovich, 1990.
Dunki-Jacobs, et al, Evaluation of resistance as a measure of successful tumor ablation during irreversible electroporation of the pancreas, American College of Surgeons, Feb. 2014, vol. 218, No. 2, pp. 179-187.
Dupuy, and Shulman, Current status of thermal ablation treatments for lung malignancies, Seminars in Interventional Radiology, 2010, vol. 27, No. 3, pp. 268-275.
Dupuy, et al, Irreversible electroporation in a swine lung model, Cardiovasc Intervent Radiol, Dec. 30, 2010, 34, pp. 391-395.
Edd, J.F, et al., 2007, "Mathematical modeling of irreversible electroporation fortreatment planning.", Technology in Cancer Research and Treatment, 6:275-286.

(56) References Cited

OTHER PUBLICATIONS

Ellis TL, Garcia PA, Rossmeisl JH, Jr., Henao-Guerrero N, Robertson J, et al., "Nonthermal irreversible electroporatior for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Faroja, et al, Irreversible electroporation ablation: Is all the damage nonthermal?, Radiology, Feb. 2013, vol. 266, No. 2, pp. 462-470.
Fischbach, et al, Engineering tumors with 3D scaffolds, Nature Methods, Sep. 2, 2007, vol. 4, No. 10, pp. 855-860.
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).
Foster, R.S., et al., Production of Prostatic Lesions in Canines Using Transrectally Administered High-Intensity Focused Ultrasound. Eur. Urol., 1993; 23: 330-336.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41,2012.
Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).
Gabriel, C, Dielectric properties of biological tissue: variation with age. Bioelectromagnetics, 2005. Suppl 7: p. S12-8.
Garca-Sánchez, T., A. Azan, I. Leray, J. Rosell-Ferrer, R. Bragos, and L. M. Mir, "Interpulse multifrequency electrical Impedance measurements during electroporation of adherent differentiated myotubes," Bioelectrochemistry, vol. 105, pp. 123-135, 2015.
Garcia et al., "Irreversible electroporation (IRE) to treat brain cancer." ASME Summer Bioengineering Conference, Marco Island, FL, Jun. 25-29, 2008, 2 pages.
Garcia et al., "Towards a Predictive Model of Electroporation-Based Therapies using Pre-Pulse Electrical Measurements" Abstract presented in the IEEE Engineering in Medicine and Biology Conference in Aug. 28, 2012 in San Diego, California, 4 pages.
Garcia P.A., et al., "Pilot study of irreversible electroporation for intracranial surgery", Conf Proc IEEE Eng Med Biol Soc, 2009:6513-6516, 2009.
Garcia P.A., et al., "7.0-T Magnetic Resonance Imaging Characterization of Acute Blood-Brain-Barrier Disruption Achieved with Intracranial Irreversible Electroporation", PLOS One, Nov. 2012, 7:11, e50482.
Garcia, et al, A parametric study delineating irreversible electroporation from thermal damage based on a minimally invasive intracranial procedure, Biomedical Engineering Online, 2011, 10: 34, pp. 1-21.
Garcia, et al, Irreversible electroporation (IRE) to treat brain tumors, Proceedings of the ASME 2008 Summer Bioengineering Conference (SBC2008), Jun. 25, 2008, pp. 6-7.
McCarley, and Soulen, Percutaneous ablation of hepatic tumors, Seminars in Interventional Radiology, 2010, vol. 27, No. 3, pp. 255-260.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.

McNeal, D. R., "Analysis of a Model for Excitation of Myelinated Nerve," IEEE Trans. Biomed. Eng., vol. BME-23, No. 4 329-337, 1976, 9 pages.
McWilliams, et al, Image-guided tumor ablation: Emerging technologies and future directions, Seminars in Interventional Radiology, 2010, vol. 27, No. 3, pp. 302-313.
Mercadal, B. et al., "Avoiding nerve stimulation in irreversible electroporation: A numerical modeling study," Phys. Med. Biol., vol. 62, No. 20, 8060-8079, 2017, 28 pages.
Miklavčič, D. et al., "The effect of high frequency electric pulses on muscle contractions and antitumor efficiency in vivo or a potential use in clinical electrochemotherapy," Bioelectrochemistry, vol. 65,121-128, 2004, 8 pages.
Min, M., A. Giannitsis, R. Land, B. Cahill, U. Pliquett, T. Nacke, D. Frense, G. Gastrock, and D. Beckmann, Comparison of rectangular wave excitations in broad band impedance spectroscopy for microfluidic applications, in World Congress on Medical Physics and Biomedical Engineering, Sep. 7-12, 2009, Munich, Germany. Springer, 2009, pp. 85-88.
Min, M., U. Pliquett, T. Nacke, A. Barthel, P. Annus, and R. Land, "Broadband excitation for short-time impedance spectroscopy," Physiological measurement, vol. 29, No. 6, p. S185,2008.
Mir et al., "Mechanisms of Electrochemotherapy" Advanced Drug Delivery Reviews 35:107-118 (1999).
Mir et al., British Journal of Cancer, 77(12):2336-2342 (1998).
Mir, Chapter 1 application of electroporation gene therapy: Past, current and future, Electroporation Protocols: Preclinical and Clinical Gene Medicine, Methods in Molecular Biology, vol. 423, 2008, pp. 3-17.
Mir, Orlowski, Introduction: Electropermeabilization as a new drug delivery approach, Methods in Molecular Medicine, 2000, vol. 37, pp. 99-117.
Mulhall et al., "Cancer, pre-cancer and normal oral cells distinguished by dielectrophoresis." Analytical and Bioanalytical Chemistry, vol. 401, pp. 2455-2463 (2011).
Nath, S., Dimarco, J. P. and Haines, D. E. (1994), Basic Aspects of Radiofrequency Catheter Ablation. Journal of Cardiovascular Electrophysiology, 5: 863-876.
Neal II, et al, Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.
Neal II, et al, Successful treatment of a large soft tissue sarcoma with irreversible electroporaiton, Journal of Clinical Oncology, May 1, 2011, vol. 29, No. 13, pp. e372-e377.
Neal II, R. E. et al. In Vitro and Numerical Support for Combinatorial Irreversible Electroporation and Electrochemotherapy Glioma Treatment. Annals of Biomedical Engineering, Oct. 29, 2013,13 pages.
Neal II, R.E., et al., "Treatment of breast cancer through the application of irreversible electroporation using a novel minimally invasive single needle electrode." Breast Cancer Research and Treatment, 2010. 123(1): p. 295-301.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.
Neal Re II, et al. (2013) Improved Local and Systemic Anti-Tumor Efficacy for Irreversible Electroporation in Immunocompetent versus Immunodeficient Mice. PLoS One 8(5): e64559. https://doi.org/10.1371/journal.pone.0064559.
Neal, Davalos, The feasibility of irreversible electroporation for the treatment of breast cancer and other heterogeneous systems, Annals of Biomedical Engineering, Dec. 2009, vol. 37, No. 12, pp. 2615-2625.
Neal, et al, A study using irreversible electroporation to treat large, irregular tumors in a canine patient, 32nd Annual International Conference of the IEEE EMBS, IEEE, Aug. 2010, pp. 2747-2750.
Neal, et al, An "Off-the-Shelf" system for intraprocedural electrical current evaluation and monitoring of irreversible electroporation therapy, Cardiovasc Intervent Radiol, Feb. 27, 2014.

(56) References Cited

OTHER PUBLICATIONS

Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neu, and Neu, Mechanism of irreversible electroporation in cells: Insight from the models, Irreversible Electroporation: Biomed, pp. 85-122.
Neven et al., Epicardial Linear Electroporation Ablation and Lesion Size, Department of Cardiology, University of Medical Utrecht, Aug. 2014, vol. 11, No. 8.
Nikolova, B., et al., "Treatment of Melanoma by Electroporation of Bacillus Calmette-Guerin". Biotechnology & Biotechnological Equipment, 25(3): p. 2522-2524 (2011).
Nikolski, et al., Electroporation of the heart, Europace, 2005, 7, pp. S146-S154.
Nuccitelli, R., et al., "A new pulsed electric field therapy for melanoma disrupts the tumor's blood supply and causes complete remission without recurrence", Int J Cancer, 125(2): p. 438-445 (2009).
O'Brien, T. J. et al., "Effects of internal electrode cooling on irreversible electroporation using a perfused organ Model," Int. J. Hyperth., vol. 35, No. 1, pp. 44-55, 2018.
O'Brien et al., "Investigation of the Alamar Blue (resazurin) fluorescent dye for the assessment of mammalian cell cytotoxicity." European Journal of Biochemistry, vol. 267, pp. 5421-5426 (2000).
Ohio Environmental Protection Agency, Ground Water Flow and Fate and Transport Modeling, State of Ohio Environmental Protection Agency, 2007, pp. 14-1-14-32.
Onik, and Rubinsky, Irreversible electroporation: First patient experience focal therapy of prostate cancer, Irreversible Electroporation, Biomed, pp. 235-247.
Onik, et al, Irreversible electroporation: Implications for prostate ablation, Technology in Cancer Research and Treatment, Aug. 2007, vol. 6, No. 4, pp. 295-300.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G.,P. Mikus, and B. Rubinsky, "Irreversible electroporation: implications for prostate ablation." Technol Cancer Res Treat, 2007. 6(4): p. 295-300.
Ott, H. C., et al., "Perfusion-decellularized matrix: using nature's platform to engineer a bioartificial heart", Nature Medicine, Nature Publishing Group, New York, NY, US, vol. 14, No. 2,Feb. 1, 2008, pp. 213-221.
Pakhomova, O. N., Gregory, B., Semenov 1., and Pakhomov, A. G., BBA—Biomembr., 2014, 1838, 2547-2554.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol, vol. 31, No. 3, 482-491.e4, Mar. 2020, 19 pages.
Paszek et al., "Tensional homeostasis and the malignant phenotype." Cancer Cell, vol. 8, pp. 241-254 (2005).
Pavseij, N. et al. The course of tissue permeabilization studied on a mathematical model of a subcutaneous tumor in small animals. IEEE Trans Biomed Eng 52,1373-1381 (2005).
Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).
PCT Application No. PCT/US 19/51731 (VTIP-A1001-PCT), International Search Report and Written Opinion dated Feb. 20, 2020,19 pgs.
PCT Application No. PCT/US09/62806, International Search Report (dated Jan. 19, 2010), Written Opinion (dated Jan. 19, 2010), and International Preliminary Report on Patentability (dated Jan. 4, 2010), 15 pgs.
PCT Application No. PCT/US10/53077, International Search Report (dated Aug. 2, 2011), Written Opinion (dated Aug. 2, 2011), and International Preliminary Report on Patentability (dated Apr. 17, 2012).
PCT Application No. PCT/US15/30429 (VTIP-97), International Search Report and Written Opinion dated Oct. 16, 2015,19 pages.
PCT Application No. PCT/US15/65792, International Search Report (dated Feb. 9, 2016), Written Opinion (dated Feb. 9, 2016), and International Preliminary Report on Patentability (dated Jun. 20, 2017), 15 pages.
PCT Application No. PCT/US2004/043477, International Search Report (dated Aug. 26, 2005), Written Opinion (dated Aug. 26, 2005), and International Preliminary Report on Patentability (dated Jun. 26, 2006).
PCT Application No. PCT/US2009/042100, International Search Report (dated Jul. 9, 2009), Written Opinion (dated Jul. 9, 2009), and International Preliminary Report on Patentability (dated Nov. 2, 2010).
PCT Application No. PCT/US2010/030629, International Search Report (dated Jul. 15, 2010), Written Opinion (dated Jul. 15, 2010), and International Preliminary Report on Patentability (dated Oct. 11, 2011).
Garcia, et al, Non-thermal irreversible electroporation (N-TIRE) and adjuvant fractionated radiotherapeutic multimodal therapy for intracranial malignant glioma in a canine patient, Feb. 2011, vol. 10, No. 1, pp. 73-83.
Garcia, et al, Non-thermal irreversible electroporation for deep intracranial disorders, 32nd Annual International Conference of the IEEE EMBS, IEEE, Aug. 2010, pp. 2747463.
Garcia, et al, Position paper concerning the use of Angiodynamics' nanoknife system for treatment of brain gliomas, Virgina Tech—Wake Forest University, May 22, 2013, pp. 1-46.
Garcia, P.A., et al., Intracranial Nonthermal Irreversible Electroporation: In Vivo Analysis. Journal of Membrane Biology, 2010. 236(1): p. 127-136.
Garcia, P.A., R.V. Davalos, and D. Miklavcic, A Numerical Investigation of the Electric and Thermal Cell Kill Distributions in Electroporation-Based Therapies in Tissue. Plos One, 2014. 9(8).
Garcia, Paulo A., Robert E. Neal IL and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010,22 pages.
Gascoyne et al., "Membrane changes accompanying the induced differentiation of Friend murine erythroleukemia cells studied by dielectrophoresis." Biochimica et Biophysica Acta (BBA)—Biomembranes, vol. 1149, pp. 119-126 (1993).
Gawad, S., T. Sun, N. G. Green, and H. Morgan, "Impedance spectroscopy using maximum length sequences: Application to single cell analysis," Review of Scientific Instruments, vol. 78, No. 5, p. 054301,2007.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa, et al, Dielectric spectroscopy of single human erythrocytes at physiological ionic strength: Dispersion of the cytoplasm, Biophysical Journal, Jul. 1996, vol. 71, pp. 495-506.
Golberg, A. and Rubinsky, B., "A statistical model for multidimensional irreversible electroporation cell death in tissue." Biomed Eng Online, 9,13 pages, 2010.
Gowrishankar et al., An Approach to electrical modeling of single and multiple cells, Mar. 18, 2003, PNAS, vol. 100 No. 6, pp. 3203-3208.
Gowrishankar T.R., et al., "Microdosimetry for conventional and supra-electroporation in cells with organelles". Biochem Biophys Res Commun, 341(4): p. 1266-76 (2006).
Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927,2009.
Groen, M. H. A. et al., "In Vivo Analysis of the Origin and Characteristics of Gaseous Microemboli during Catheter-Mediated Irreversible Electroporation," Europace, 2021, 23(1), 139-146.

(56) References Cited

OTHER PUBLICATIONS

Guenther, E. et al., "Electrical breakdown in tissue electroporation," Biochem. Biophys. Res. Commun., vol. 467, No. 4, 736-741, Nov. 2015, 15 pages.
Guo, et al, Irreversible electroporation in the liver: Contrast-enhanced inversion-recovery MR imaging approaches to differentiate reversibly electroporated penumbra from irreversibly electroporated ablation zones, Radiology, Feb. 2011, vol. 258, No. 2, pp. 461-468.
Hall, et al, Nanosecond pulsed electric fields have differential effects on cells in the S-phase, DNA and Cell Biology, 2007, vol. 26, No. 3, pp. 160-171.
Hall, et al, Nanosecond pulsed electric fields induce apoptosis in p53-wildtype and p53-null HCT116 colon carcinoma cells, Apoptosis, May 23, 2007, 12, pp. 1721-1731.
Hasgall, P. et al., "IT'IS Database for thermal and electromagnetic parameters of biological tissues," 2018, it.is.swiss/database%0A%0A.
He, et al, Nonlinear current response of micro electroporation and resealing dynamics for human cancer cells, Bioelectrochemistry, Jan. 29, 2008, 72, pp. 161-168.
Helczynska et al., "Hypoxia promotes a dedifferentiated phenotype in ductal breast carcinoma in situ." Cancer Research, vol. 63, pp. 1441-1444 (2003).
Hjouj, et al, MRI study on reversible and irreversible electroporation induced blood brain barrier disruption, Aug. 10, 2012, PLOS One, vol. 7, 8, e42817, pp. 1-9.
Hjouj, M., et al., "MRI Study on Reversible and Irreversible Electroporation Induced Blood Brain Barrier Disruption", PLOS One, Aug. 2012, 7:8, e42817.
Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. iii114.
Hoejholt, K. L. et al. Calcium electroporation and electrochemotherapy for cancer treatment: Importance of cell Tiembrane composition investigated by lipidomics, calorimetry and in vitro efficacy. Scientific Reports (Mar. 18, 2019) 3:4758, p. 1-12.
Hong, et al, Cardiac ablation via electroporation, 31st Annual International Conference of the IEEE EMBS, IEEE, Sep. 2, 2009, pp. 3381-3384.
Hu, Q., et al., "Simulations of transient membrane behavior in cells subjected to a high-intensity ultrashort electric pulse", Physical Review E, 71(3) (2005).
Ibey et al., "Selective cytotoxicity of intense nanosecond-duration electric pulses in mammalian cells." Biochimica Et Biophysica Acta—General Subjects, vol. 1800, pp. 1210-1219 (2010).
International Application No. PCT/US2009/042100, International Search Report dated Jul. 9, 2009, 5 pages.
International Search Report 06751655_SESR dated Oct. 16, 2009.
International Search Report 07716249_SESR dated Jan. 19, 2009.
International Search Report 09739678_SESR dated May 3, 2012.
International Search Report 12002108_EPS dated May 30, 2012.
International Search Report 12002108.4 ESO dated Jun. 12, 2013.
International Search Report for 06751655 SESR dated Oct. 9, 2016.
International Search Report for 06751655.9 ESO dated Oct. 29, 2009.
International Search Report for 10824248.8 ESO dated Jan. 20, 2014.
International Search Report for 11833421 SESR dated Mar. 18, 2014.
International Search Report for IPRP, PCT/US2006/01645, dated Oct. 30, 2007, 5 pages.
International Search Report for PCT-US-10-053077 ISR dated Aug. 2, 2011.
International Search Report for PCT-US-10-053077 WOSA dated Aug. 2, 2011.
International Search Report for PCT/US06/16045 ISR dated Sep. 25, 2007, 1 page.
International Search Report for PCT/US2006/016045 IPRP dated Oct. 30, 2007.
International Search Report for PCT/US2007/000084 IPRP dated Jul. 8, 2008, 8 pages.
International Search Report for PCT/US2009/038661 IPRP dated Sep. 28, 2010.
International Search Report for PCT/US2009/042100 IPRP dated Nov. 2, 2010.
International Search Report for PCT/US2009/042100 WOSA dated Jul. 9, 2009.
International Search Report for PCT/US2009/047969 IPRP dated Dec. 21, 2010.
International Search Report for PCT/US2009/047969 ISR dated Jan. 21, 2010.
International Search Report for PCT/US2009/047969 WOSA dated Jan. 21, 2010.
International Search Report for PCT/US2009/048270 IPRP dated Jan. 5, 2011.
International Search Report for PCT/US2009/048270 ISR dated Feb. 11, 2010.
International Search Report for PCT/US2009/048270 WOSA dated Feb. 11, 2010.
International Search Report for PCT/US2009/062806 WOSA dated Jan. 19, 2010.
International Search Report for PCT/US2010/022011 IPRP dated Jul. 26, 2011.
International Search Report for PCT/US2010/022011 ISR dated Aug. 30, 2010.
International Search Report for PCT/US2010/022011 WOSA dated Aug. 30, 2010.
International Search Report for PCT/US2010/029243 IPRP dated Oct. 4, 2011.
International Search Report for PCT/US2010/029243 WOSA dated Jul. 30, 2010.
International Search Report for PCT/US2010/036734 IPRP dated Nov. 29, 2011.
International Search Report for PCT/US2010/036734 ISR dated Dec. 23, 2010.
International Search Report for PCT/US2010/036734 WOSA dated Dec. 23, 2010.
International Search Report for PCT/US2010/053077 IPRP dated Apr. 17, 2012.
International Search Report for PCT/US2011/024909 IPRP dated Aug. 21, 2012.
International Search Report for PCT/US2011/024909 ISR dated Oct. 18, 2011.
International Search Report for PCT/US2011/024909 WOSA dated Oct. 18, 2011.
International Search Report for PCT/US2011/025003 IPRP dated Aug. 21, 2012.
International Search Report for PCT/US2011/025003 ISR dated Oct. 24, 2011. 10 pages.
International Search Report for PCT/US2011/025003 WOSA dated Oct. 24, 2011.
International Search Report for PCT/US2011/056177 ESO dated Mar. 28, 2014.
International Search Report for PCT/US2011/056177 IPRP dated Apr. 16, 2013.
International Search Report for PCT/US2011/056177 ISR dated May 30, 2012.
International Search Report for PCT/US2011/056177 WOSA dated May 30, 2012.
International Search Report for PCT/US2011/062067 IPRP dated May 28, 2013.
International Search Report for PCT/US2011/062067 ISR dated Jul. 25, 2012.
International Search Report for PCT/US2011/062067 WOSA dated Jul. 25, 2012.
International Search Report for PCT/US2015/065792 dated Feb. 9, 2016.
International Search Report PCT-US-07-000084 ISR dated Dec. 14, 2007, 2 pages.

(56) References Cited

OTHER PUBLICATIONS

International Search Report PCT/US07/00084 WOSA dated Dec. 14, 2007, 7 pages.
International Search Report PCT/US2009/038661 ISR dated Jun. 12, 2009.
International Search Report PCT/US2009042100 ESO dated May 11, 2012.
Issa, et al, Recent Reports: The TUNA procedure for BPH: Review of the technology, Infections in Urology, Jul. 1998, 8 pages.
Issa, et al, Specialty Surgery: The TUNA procedure for BPH: Basic procedure and clinical results, Infections in Urology, Sep. 1998, 6 pages.
Ivey, J_ W., E. L. Latouche, M. B. Sano, J_ H. Rossmeisl, R. V. Davalos, and S. S. Verbridge, "Targeted cellular ablation based on the morphology of malignant cells," Sci. Rep., vol. 5, pp. 1-17, 2015.
Ivorra et al., "In vivo electric impedance measurements during and after electroporation of rat live." Bioelectrochemistry, vol. 70, pp. 287-295 (2007).
Ivorra, et al, In vivo electrical conductivity measurements during and after tumor electroporation: conductivity changes reflect the treatment outcome,Phys. Med. Biol., Sep. 17, 2009, 54, pp. 5949-5963.
Ivorra, et al., Impedance analyzer for in vivo electroporation studies, Proceedings of the 28th IEEE EMBS Annual International Conference, IEEE, Aug. 30, 2006, pp. 5056-5059.
Ivorra,"Bioimpedance monitoring for physicians: an overview." Biomedical Applications Group, 35 pages (2002).
Jan Ko et al, "New anti-huntingtin monoclonal antibodies: implications for huntingtin conformation and its binding proteins", Brain Research Bulletin, Elsevier Science Ltd, Oxford, GB, (Oct. 1, 2001), vol. 56, No. 3-4, doi:10.1016/S0361-9230(01)00599-8, ISSN 0361-9230, pp. 319-329, XP002509144.
Jarm et al., "Antivascular effects of electrochemotherapy: implications in treatment of bleeding metastases." Expert Rev Anticancer Ther. vol. 10, pp. 729-746 (2010).
Jensen et al., "Tumor volume in subcutaneous mouse xenografts measured by microCT is more accurate and reproducible than determined by 18FFDG-microPET or external caliper." BMC medical Imaging vol. 8:16, 9 Pages 2008).
Jiang, et al, Membrane-targeting approaches for enhanced cancer cell destruction with irreversible electroporation, Annuals of Biomedical Engineering, Aug. 15, 2013.
Jordan, D.W., et al., "Effect of pulsed, high-power radiofrequency radiation on electroporation of mammalian cells", Ieee Transactions on Plasma Science, 32(4): p. 1573-1578 (2004).
Jossinet et al., Electrical Impedance Endo-Tomography: Imaging Tissue From Inside, IEEE Transactions on Medical Imaging, vol. 21, No. 6, Jun. 2002, pp. 560-565.
Kanduser, et al, Cell membrane fluidity related to electroporation and resealing, Eur Biophys J, Oct. 8, 2006, 35, pp. 196-204.
Katsuki, S., et al., "Biological effects of narrow band pulsed electric fields", Ieee Transactions on Dielectrics and Electrical Insulation,. 14(3): p. 663-668 (2007).
Kingham et al., "Ablation of perivascular hepatic malignant tumors with irreversible electroporation." Journal of the American College of Surgeons, 2012. 215(3), p. 379-387.
Kinosita et al., "Electroporation of cell membrane visualized under a pulsed-laser fluorescence microscope." Biophysical Journal, vol. 53, pp. 1015-1019 (1988).
Kinosita et al., "Voltage-induced pore formation and hemolysis of human erythrocytes." Biochimica et Biophysica Acta (BBA)—Biomembranes, 471 (1977) pp. 227-242.
Alberts et al., "Molecular Biology of the Cell," 3rd edition, Garland Science, New York, 1994, 1 page.
Bagla, Papadouris, Percutaneous irreversible electroporation of surgically unresectable pancreatic cancer: A case report, J Vasc Interv Radiol, 2012, 23, pp. 142-145.

Blad, et al., Impedance Spectra of Tumour Tissue in Comparison with Normal Tissue; a Possible Clinical Application for Electrical Impedance Tomography, Physiol. Meas. 17 (1996) A105-A115.
Boone, K., Barber, D. & Brown, B. Review—Imaging with electricity: report of the European Concerted Action on Impedance Tomography. J. Med. Eng. Technol. 21, 201-232 (1997).
BPH Management Strategies: Improving Patient Satisfaction, Urology Times, May 2001, vol. 29, Supplement 1. 22 pages.
Duraiswami, et al., Solution of Electrical Impedance Tomography Equations Using Boundary Element Methods, Boundary Element Technology XU, 1997, pp. 226-237.
Edd et al., "Mathematical modeling of irreversible electroporation for treatment planning." Technology in Cancer 20 Research and Treatment, vol. 6, No. 4, pp. 275-286 (2007).
Edd, J., et al., In-Vivo Results of a New Focal Tissue Ablation Technique: Irreversible Electroporaton, IEEE Trans. 21 Biomed. Eng. 53 (2006) p. 1409-1415.
Faroja, M., et al., "Irreversible Electroporation Ablation: Is the entire Damage Nonthermal?", Radiology, 266(2), 28 462-470 (2013).
Garcia, et al., "A Parametric Study Delineating Irreversible Electroporation from Thermal Damage Based on a 40 Minimally Invasive Intracranial Procedure," Biomed Eng Online, vol. 10:34, 22 pages, 2011.
Garcia, P. A., et al., "Towards a predictive model of electroporation-based therapies using pre-pulse electrical 41 measurements," Conf Proc IEEE Eng Med Biol Soc, vol. 2012, pp. 2575-2578, 2012.
Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-83 (2011).
Glidewell, et al., The Use of Magnetic Resonance Imaging Data and the Inclusion of Anisotropic Regions in Electrical Impedance Tomography, Biomed, Sci. Instrum. 1993; 29: 251-7.
Griffiths, Tissue Spectroscopy with Electrical Impedance Tomography: Computer Simulations, IEEE Transactions on Biomedical Engineering, vol. 42, No. 9, Sep. 1995. 8 pages.
Gumerov, et al, The dipole approximation method and its coupling with the regular boundar yelement method for efficient electrical impedance tomography, BETECH Jun. 1999.
Huang, Rubinsky, Micro-electroporation: improving the efficiency and understanding of electrical permeabilization of cells, Biomedical Microdevices, 1999, 2:2, pp. 145-150.
Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.
Lee, E.W., et al., "Imaging guided percutaneous irreversible electroporation: ultrasound and immunohistological correlation", Technol Cancer Res Treat 6: 287-294 (2007).
Li, W., et al., "The Effects of Irreversible Electroporation (IRE) on Nerves" PloS One, Apr. 2011, 6(4), e18831. 7 pages.
Mercadal, Borja et al. "Dynamics of Cell Death After Conventional IRE and H-FIRE Treatments", Annals of Biomedical Engineering, vol. 48, No. 5, 2020, p. 1451-1462.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001. 1 page.
Neal II et al., "A Case Report on the Successful Treatment of a Large Soft-Tissue Sarcoma with Irreversible Electroporation," Journal of Clinical Oncology, 29, pp. 1-6, 2011.
Neal II, R. E., et al., "Successful Treatment of a Large Soft Tissue Sarcoma with Irreversible Electroporation", Journal of Clinical Oncology, 29:13, e372-e377 (2011).
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
PCT Application No. PCT/2011/062067, International Preliminary Report on Patentability dated May 28, 2013. 7 pages.
PCT Application No. PCT/2011/066239, International Preliminary Report on Patentability dated Jun. 25, 2013. 7 pages.

(56) References Cited

OTHER PUBLICATIONS

PCT Application No. PCT/US15/30429, International Report on Patentability dated Nov. 15, 2016. 7 pages.
PCT Application No. PCT/US19/51731 (VTIP-A1001-PCT), International Preliminary Report on Patentability dated Mar. 23, 2021, 13 pages.
Pending Application No. PCT/US21/51551 (VTIP-A1018-PCT), International Search Report and Written Opinion dated Dec. 29, 2021, 14 pages.
Pending Application No. PCT/US23/15118 (VTIP-A1023-PCT), International Search Report and Written Opinion dated Jul. 31, 2023, 18 pages.
Phillips, M., Maor, E. & Rubinsky, B. Nonthermal Irreversible Electroporation for Tissue Decellularization. J. Biomech. Eng, doi: :10.1115/1.4001882 (2010). 8 pages.
Polak et al., "On the Electroporation Thresholds of Lipid Bilayers: Molecular Dynamics Simulation Investigations." The Journal of Membrane Biology, vol. 246, pp. 843-850 (2013).
Rebersek, M. and D. Miklav, "Advantages and Disadvantages of Different Concepts of Electroporation Pulse Generation," Automatika 52(2011) 1, 12-19.
Thomson et al., "Investigation of the safety of irreversible electroporation in humans," J Vasc Interv Radiol, 22, pp. 611-621, 2011.
TUNA—Suggested Local Anesthesia Guidelines, no date available. 1 page.
Precision Office TUNA System, "When Patient Satisfaction is Your Goal." Product Literature Published by VidaMed, Inc., 11 pages (2001).

\* cited by examiner

SYSTEM AND METHOD FOR ELECTRICALLY ABLATING TISSUE OF A PATIENT

CROSS-REFERENCE TO RELATED APPLICATION

This application is a Continuation of U.S. Non-Provisional application Ser. No. 15/612,006, filed Jun. 2, 2017, which is a Continuation of U.S. Non-Provisional application Ser. No. 13/273,001, now U.S. Pat. No. 9,700,368, filed Oct. 13, 2011, which claims the benefit of U.S. Provisional Application No. 61/392,905, filed Oct. 13, 2010, all of which is incorporated by reference herein.

This application is also related to PCT International Application Number PCT/US10/29243, filed Mar. 30, 2010 and entitled "System and Method for Estimating a Treatment Region for a Medical Treatment Device and for Interactively Planning a Treatment of a Patient" (hereinafter the "IRE Treatment Application"), which is incorporated herein by reference.

This application is also related to PCT International Application Number PCT/US10/36734, filed May 28, 2010 and entitled "System and Method for Synchronizing Energy Delivery to the Cardiac Rhythm", which is also incorporated herein by reference.

FIELD OF THE INVENTION

The present invention relates to a control system for controlling a medical treatment device. More particularly, the present application relates to a system and method for electrically ablating tissue of a patient.

BACKGROUND OF THE INVENTION

Devices for delivering therapeutic energy such as an ablation device using irreversible electroporation (IRE) include a pulse generator and one or more electrodes coupled to the generator. The pulse generator delivers the therapeutic energy to a targeted tissue through the electrodes, thereby causing ablation of the tissue.

Once a target treatment area/region is located within a patient, the electrodes of the device are placed in such a way as to create a treatment zone that surrounds the target treatment region.

Prior to treatment, a treatment planning system is used to generate an estimated treatment region that completely covers the target treatment region. The estimated region is used by a physician to plan where to place the electrodes in the patient.

This can be effective when the target area is relatively small, e.g., less than 2 cm in length. However, when the target area is much larger, e.g., larger than 3 cm in length, the physician is forced to use a large number of electrodes, e.g., 4 or more electrodes. This makes accurately placing the electrodes much more difficult as moving one electrode affects the spacing from all other electrodes.

Alternatively, the large target area can be divided into two or more smaller areas and the treatment procedure for one area can be repeated to cover the other divided areas. However, this makes the entire treatment procedure much longer. The longer procedure makes it riskier for the patient since the patient would have to stay on an operating table much longer with an exposed body portion to be treated. The longer procedure also makes the procedure more expensive.

Therefore, it would be desirable to provide a system and method for electrically ablating tissue of a patient more safely and efficiently.

SUMMARY OF THE DISCLOSURE

According to one aspect of the invention, a system for electrically ablating tissue of a patient through a plurality of electrodes is provided. The system includes a memory, a processor and a treatment control module stored in the memory and executable by the processor. The treatment control module generates an estimated treatment region by taking into account the relationship between the ablation size and the number of pulses to be applied. This allows treatment of relatively large target ablation regions more efficiently and accurately.

According to another aspect of the invention, a method of electrically ablating tissue of a patient through a plurality of electrodes is provided. The method includes receiving positions of a plurality of electrodes and generating an estimated treatment region based on the received electrode positions and the number of pulses to be applied.

BRIEF DESCRIPTION OF THE DRAWINGS

FIG. 3 is a screen shot of an "Information" screen of a treatment control module showing various input boxes.

FIG. 4 is a screen shot of a "Probe Selection" screen of the treatment control module showing a side view and top view of the four probe array and an example of the general shape of the treatment zone that can be generated by a four probe array.

DETAILED DESCRIPTION OF INVENTION

Throughout the present teachings, any and all of the one, two, or more features and/or components disclosed or suggested herein, explicitly or implicitly, may be practiced and/or implemented in any combinations of two, three, or more thereof, whenever and wherever appropriate as understood by one of ordinary skill in the art. The various features and/or components disclosed herein are all illustrative for the underlying concepts, and thus are non-limiting to their actual descriptions. Any means for achieving substantially the same functions are considered as foreseeable alternatives and equivalents, and are thus fully described in writing and fully enabled. The various examples, illustrations, and embodiments described herein are by no means, in any degree or extent, limiting the broadest scopes of the claimed inventions presented herein or in any future applications claiming priority to the instant application.

Figure 1:
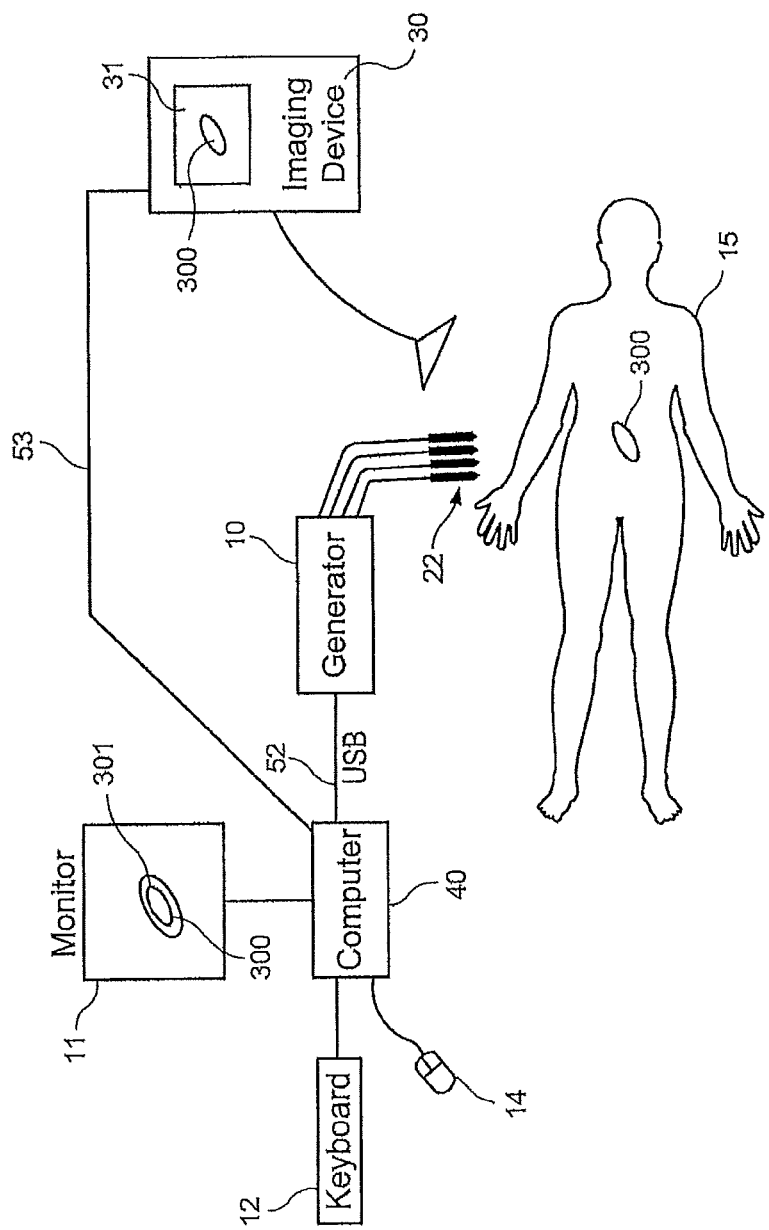
FIG. 1 illustrates several components of a medical treatment system to treat a patient according to the present invention.

One embodiment of the present invention is illustrated in FIG. 1. One or more probes/electrodes 22 deliver therapeutic energy and are powered by a voltage pulse generator 10 that generates high voltage pulses as therapeutic energy such as pulses capable of irreversibly electroporating the tissue cells. In the embodiment shown, the voltage pulse generator 10 includes six separate receptacles for receiving up to six individual probes 22 which are adapted to be plugged into the respective receptacle. The receptacles are each labeled with a number in consecutive order. In other embodiments, the voltage pulse generator can have any number of receptacles for receiving more or less than six probes.

In the embodiment shown, each probe 22 includes either a monopolar electrode or bipolar electrodes having two electrodes separated by an insulating sleeve. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein. The generator 10 is connected to a treatment control computer 40 having input devices such as keyboard 12 and a pointing device 14, and an output device such as a display device 11 for viewing an image of a target treatment region such as a lesion 300 surrounded by a safety margin 301. The pulse generator 10 is used to treat a lesion 300 inside a patient 15. An imaging device 30 includes a monitor 31 for viewing the lesion 300 inside the patient 15 in real time. Examples of imaging devices 30 include ultrasonic, CT, MRI and fluoroscopic devices as are known in the art.

The present invention includes computer software (treatment control module 54) which assists a user to plan for, execute, and review the results of a medical treatment procedure, as will be discussed in more detail below. For example, the treatment control module 54 assists a user to plan for a medical treatment procedure by enabling a user to more accurately position each of the probes 22 of the pulse generator 10 in relation to the lesion 300 in a way that will generate the most effective treatment zone. The treatment control module 54 can display the anticipated treatment zone based on the position of the probes and the treatment parameters. The treatment control module 54 can display the progress of the treatment in real time and can display the results of the treatment procedure after it is completed. This information can be used to determine whether the treatment was successful and whether it is necessary to re-treat the patient.

For purposes of this application, the terms "code", "software", "program", "application", "software code", "software module", "module" and "software program" are used interchangeably to mean software instructions that are executable by a processor.

The "user" can be a physician or other medical professional. The treatment control module 54 executed by a processor outputs various data including text and graphical data to the monitor 11 associated with the generator 10.

Figure 2:
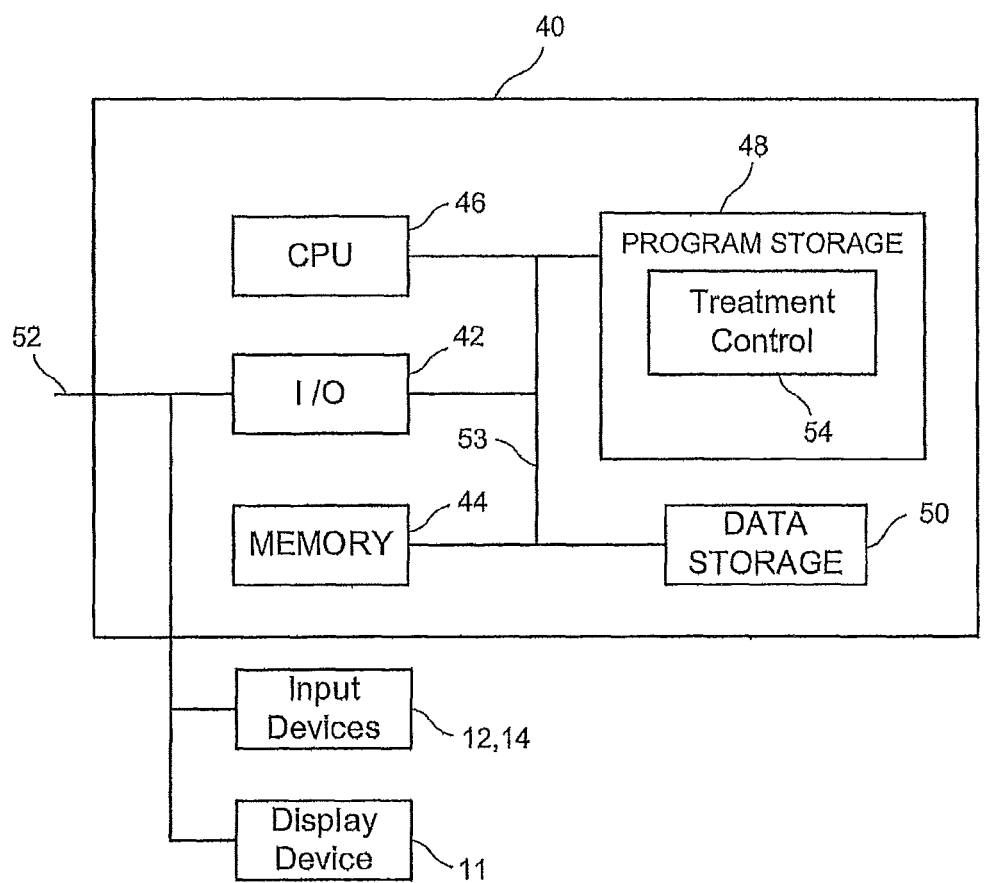
FIG. 2 is a schematic diagram of a treatment control computer of the present invention.

Referring now to FIG. 2, the treatment control computer 40 of the present invention manages planning of treatment for a patient. The computer 40 is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50 such as a hard disk, all commonly connected to each other through a bus 53. The program storage 48 stores, among others, a treatment control module 54 which includes a user interface module that interacts with the user in planning for, executing and reviewing the result of a treatment. Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communication link 52. In a preferred embodiment, the communication link 52 is a USB link.

In one embodiment, the imaging device 30 is a stand alone device which is not connected to the computer 40. In the embodiment as shown in FIG. 1, the computer 40 is connected to the imaging device 30 through a communication link 53. As shown, the communication link 53 is a USB link. In this embodiment, the computer can determine the size and orientation of the lesion 300 by analyzing the data such as the image data received from the imaging device 30, and the computer 40 can display this information on the monitor 11. In this embodiment, the lesion image generated by the imaging device 30 can be directly displayed on the grid 200 of the monitor 11 of the computer running the treatment control module 54. This embodiment would provide an accurate representation of the lesion image on the grid 200, and may eliminate the step of manually inputting the dimensions of the lesion in order to create the lesion image on the grid 200. This embodiment would also be useful to provide an accurate representation of the lesion image if the lesion has an irregular shape.

The basic functionality of the computer software (treatment control module 54) will now be discussed in relation to the following example.

It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

Figure 3:
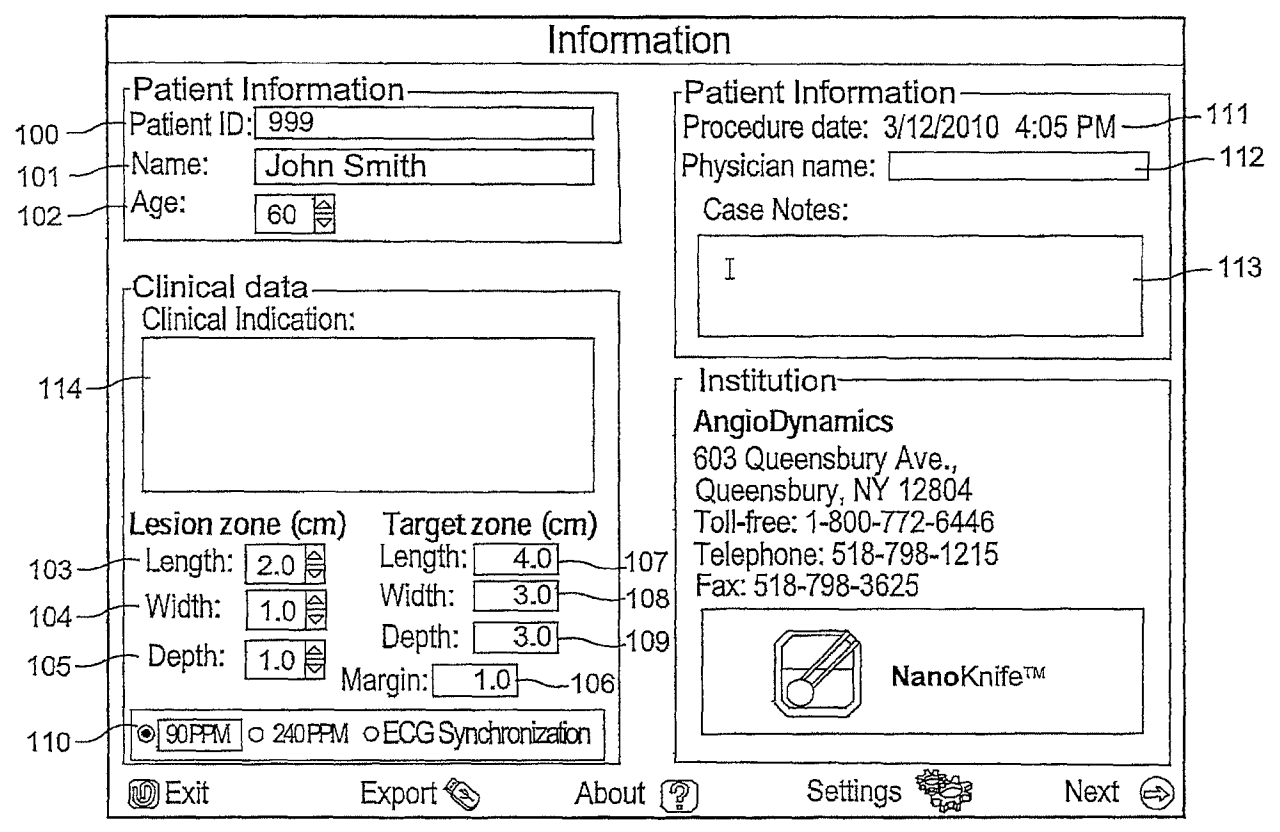

After the treatment control module 54 is initialized, it displays an "Information" screen with various input boxes as shown in FIG. 3. A keyboard or other input device 12, together with a mouse or other pointing device 14 (see FIG. 1) are used to input the data. Any data that is inputted into the input boxes can be saved into internal or external memory along with a record of the treatment as described below for future reference. The basic patient information can be inputted, such as a patient ID number in input box 100, the name of the patient in input box 101, and the age of the patient in input box 102. The user can enter clinical data, such as the clinical indication of the treatment in input box 114. The date of the procedure is automatically displayed at 111 or can be inputted by the user in another embodiment. The user can enter other case information such as the name of the physician in input box 112 and any specific case notes in input box 113.

The dimensions of the lesion 300 are determined from viewing it on the monitor 31 of the imaging device 30 (see FIG. 1) such as an ultrasonic imaging device and using known methods to calculate the dimensions from the image generated from the imaging device 31. The dimensions of the lesion 300 (length at input box 103, width at input box 104, and depth at input box 105) are inputted into the program. A safety margin is selected at input box 106 which will surround the entire lesion 300 in three dimensions. According to the size of the safety margin that is selected, a target treatment region is automatically calculated and is displayed in boxes 107, 108, and 109 as shown. In one embodiment, the safety margin value may be set to zero. For example, when treating a benign tumor, a safety margin may not be necessary.

In the embodiment shown in FIG. 3, the user has indicated that the lesion that will be treated has a length of 2 cm, width of 1 cm and a depth of 1 cm. With a user specified margin of 1 cm (which is a default margin setting), the target treatment region has a length of 4 cm, width of 3 cm and a depth of 3 cm.

The user can select the "ECG synchronization" option by clicking the circle in the box 110 in order to synchronize the pulses with an electrocardiogram (ECG) device, if such a device is being used during the procedure. The other options available for treatment that are included in box 110 can include an option for "90 PPM" (pulses per minute) or "240 PPM". The user should select at least one of the three options provided in box 110. After all of the necessary data has been inputted, the user clicks on the "Next" button with a pointing device 14 to proceed to the next screen described below.

Further regarding the ECG synchronization option, if this circle is selected in window 110, the treatment control module 54 will test this functionality to verify that the system is working properly. The treatment control module 54 can automatically detect whether an error has occurred during the testing phase of the ECG feature. The detectable errors include, but are not limited to, "no signal" (such as no pulses for 3.5 seconds) and "noisy" (such as pulses occurring at a rate greater than 120 beats per minute for at least 3.5 seconds).

The treatment control module 54 can synchronize energy release with cardiac rhythm by analyzing cardiac output such as electrocardiogram results (or other cardiac function output) and sending synchronization signals to a controller of the pulse generator 10. The control module 54 is also capable of generating internal flags such as a synchronization problem flag and a synchronization condition flag to indicate to users on a graphic user interface a synchronization status, so that energy pulse delivery can be synchronized with the cardiac rhythm for each beat (in real-time) or aborted as necessary for patient safety and treatment efficiency.

Specifically, the control module 54 synchronizes energy pulses such as IRE (irreversible electroporation) pulses with a specific portion of the cardiac rhythm. The module uses the R-wave of the heartbeat and generates a control signal to the pulse generator 10 indicating that this portion of the heartbeat is optimal for release of IRE pulses. For clarity, the S wave would be an optimal time for delivery of an energy pulse, but due to the fact that the S wave ends nebulously in some cases, the R wave is used as an indicator to start timing of energy release.

More specifically, the synchronization feature of the control module 54 allows for monitoring of heart signals so as to ensure that changes, maladies, and other alterations associated with the heartbeat are coordinated such that pulses from the pulse generator 10 are released at the proper time, and that if the heartbeat is out of its normal rhythm, that the release of energy is either altered or aborted.

Next, the user can select the number of probes that the user believes will be necessary to produce a treatment zone which will adequately cover the lesion 300 and any safety margin 301. The selection is made by clicking the circle next to each type of device, as shown in the "Probe Selection" screen, illustrated in FIG. 4.

In one embodiment, a "Probes Selection Status" box 199 identifies which of the receptacles, if any, on the generator 10 have been connected to a probe by displaying the phrase "Connected" or the like next to the corresponding probe number. In one embodiment, each receptacle includes an RFID device and a connector for each probe which connects to the receptacle and includes a compatible RFID device, so that the treatment control module 54 can detect whether or not an authorized probe has been connected to the receptacle on the generator 10 by detecting a connection of the compatible RFID devices. If an authorized probe is not connected to a receptacle on the generator, the phrase "Not Connected" or the like will appear next to the probe number. In addition, the color of each probe shown in the "Probes Selection Status" box 199 can be used to indicate whether or not each receptacle on the generator is connected to a compatible probe. This feature allows the user to verify that the requisite number of probes are properly connected to the generator 10 before selecting a probe type for the treatment procedure. For example, if the treatment control module 54 detects a problem with the probe connection status (e.g. selecting a three probe array when only two probes are connected to the generator), it can notify the user by displaying an error message.

The user can select which of the connected probes will be used to perform the treatment procedure, by clicking on the box next to the selected probes in the "Probes Selection Status" box 199. By default the treatment control module 54 will automatically select probes in ascending numerical order, as they are labeled.

Figure 4:
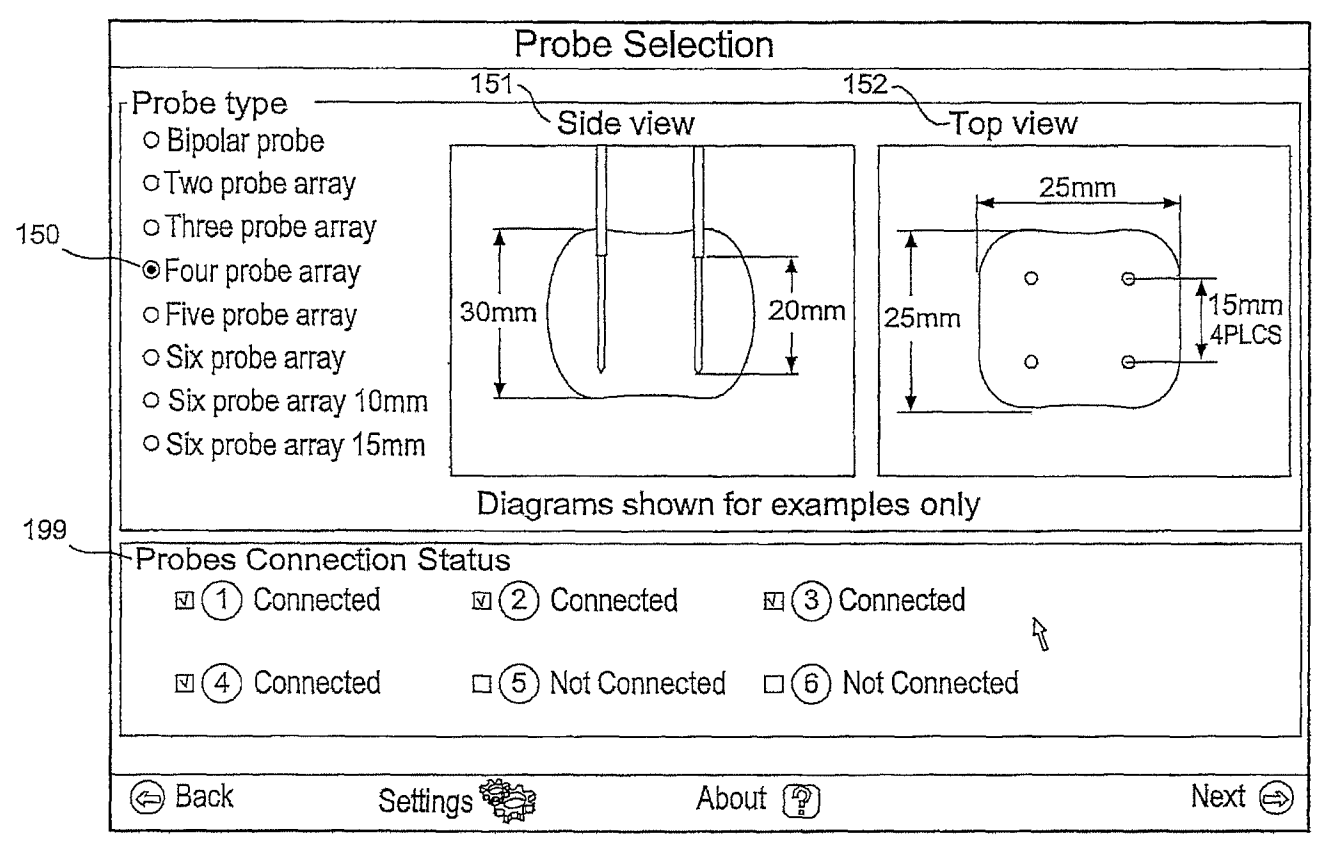

Referring to FIG. 4, circle 150 is used to select a four probe array. FIG. 4 illustrates a side view 151 and top view 152 of the four probe array and an example of the general shape of the treatment zone that can be generated by a four probe array. In the illustrated example, the exposed portion of each of the electrodes as shown is 20 mm in length and each pair of the four probes are equally spaced from each other by 15 mm, as measured at four places (PLCS) along the perimeter.

Figure 5:
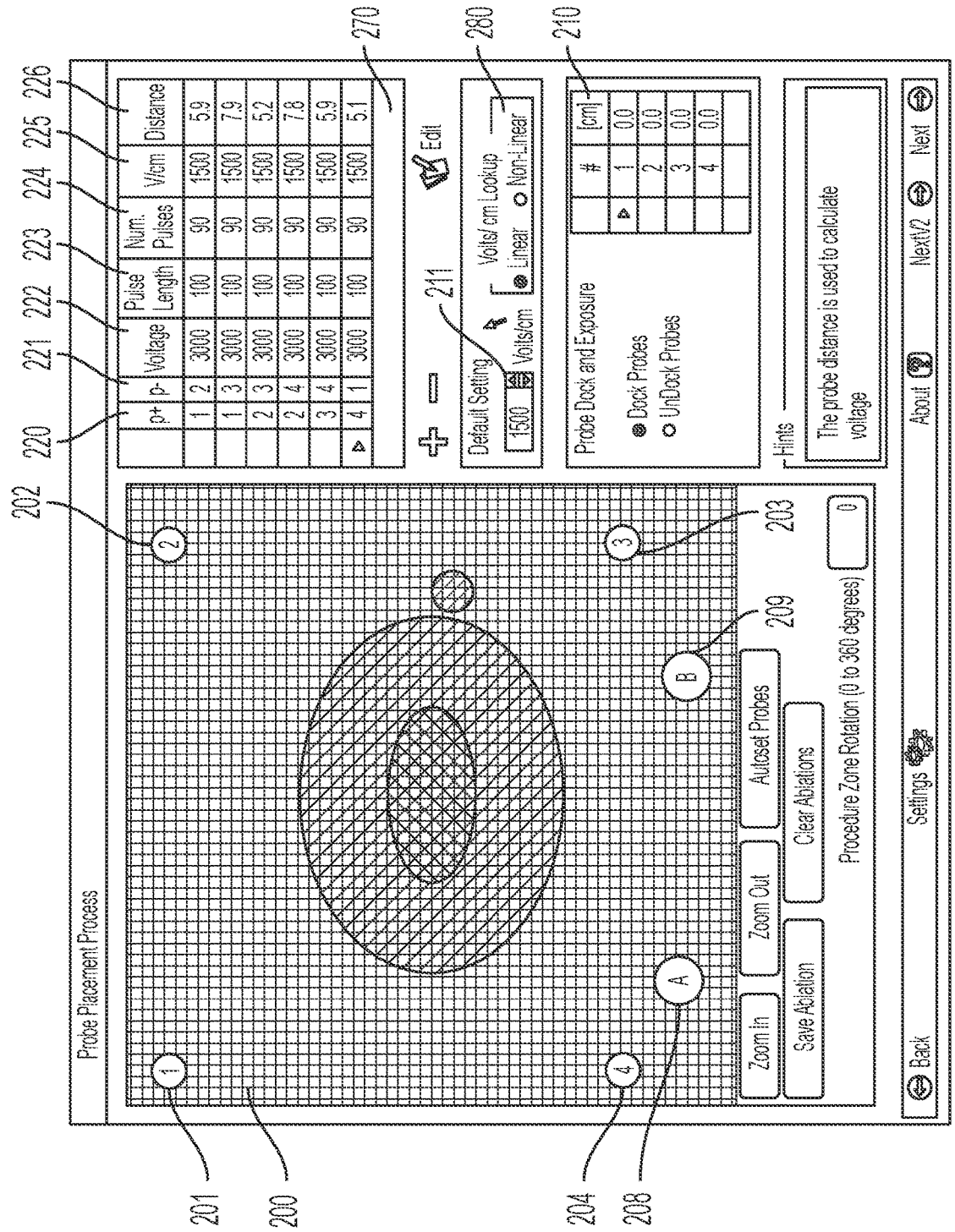
FIG. 5 is a screen shot of a "Probe Placement Process" screen of the treatment control module.

FIG. 5 illustrates a "Probe Placement Process" screen of one aspect of the invention. The screen illustrated by FIG. 5 shows a lesion 300 according to the dimensions which were inputted on the "Information" screen (see FIG. 3) along with a safety margin 301, if any, that was previously inputted. In the example depicted in FIG. 5, the lesion 300 has a length of 2.0 cm and a width of 1.0 cm, and the device selected on the "Probe Selection" screen (see FIG. 4) is a four probe array. The lesion 300 is displayed near the center of an x-y grid 200 with the distance between two adjacent grid lines representing 1 mm. Each of the four probes 201, 202, 203, 204 is displayed in the grid 200 and each probe can be manually positioned within the grid by clicking and dragging the probe with the pointing device 14. Two fiducials 208, 209 labeled "A" and "B", respectively, are also displayed on the grid 200 and are used as a point of reference or a measure as will be described below.

The amount of longitudinal exposure of the active electrode portion for each probe that has already been manually adjusted by the user as explained above can be manually inputted in input box 210, which can be selected by the user according to the depth (z) of the lesion. In this way, the treatment control module 54 can generate an estimated treatment zone according to the treatment parameters, and locations and depths of the probes. In one embodiment, a second x-z grid is displayed on the monitor 11 of the computer running the treatment control module 54. In one embodiment, the treatment control module 54 can automatically calculate preferred values for the amount of longitudinal exposure of the active electrode portions based on the size and shape of the lesion. The depth (z) of the electric field image can be calculated analytically or with interpolation and displayed on the x-z grid. Because the distribution of the electric field (i.e., expected treatment region) between two monopolar electrodes may "dip in" along the boundary line (e.g., a peanut shaped treatment region due to large spacing between the two electrodes where the width of the region is smaller in the middle; see for example region 305 in FIG. 9) depending on the electrode location and the applied voltage, it is beneficial to have an x-z grid included on the monitor. For example, if this "dip" of the boundary line travels into, rather than surround/cover, the lesion region, then the targeted region may not be fully treated. As a default to ensure treatment of the entire lesion region, the probe depth placement and the exposure length may be set unnecessarily higher to ensure erring on the safe side. However, this will potentially treat a much larger volume than needed, killing healthy surrounding tissue, which can be an issue when treating sensitive tissues such as the pancreas, brain, etc. By optimizing the treatment depth (z) together with the width (x) and height (y), this effect may be reduced, further enhancing procedural protocol and clinical outcome.

The probe dock status is indicated in box 210, by indicating if the probes are "docked" or "undocked". The "UnDock Probes" button allows the user to "unplug" the probes from the generator while the "Probe Placement Process" screen is displayed without causing error messages. In normal operation, the user plugs the probes into the generator on the "Probe Selection" screen, and then the probes are "authorized" as being compatible probes according to the RFID devices, as discussed above. When the user proceeds to the "Probe Placement Process" screen, the software requires that all the selected probes remain plugged into the generator, or else the software will display an error message (e.g. "Probe #2 unplugged", etc.), and will also force the user back to the "Probe Selection" screen. However, sometimes doctors may want to perform another scan of the lesion or perform some other procedure while leaving the probes inserted in the patient. But, if the procedure cannot be performed near the generator, the probes are unplugged from the generator. If the user selects the "UnDock Probes" button, this will allow the probes to be unplugged from the generator without causing an error message. Then, after the user has performed the other procedure that was required, he can re-attach the probes to the generator, and then select "Dock Probes" in input box 210. In this way, the user will not receive any error messages while the "Probe Placement Process" screen is displayed.

There is a default electric field density setting (Volts/cm) which is shown in input box 211. In the example, the default setting is 1500 Volts/cm. This number represents the electric field density that the user believes is needed to effectively treat the cells, e.g., ablate the tissue cells. For example, 1500 Volts/cm is an electric field density that is needed to irreversibly electroporate the tissue cells. Based on the number selected in input box 211, the treatment control module 54 automatically adjusts the voltage (treatment energy level) applied between the electrodes, as shown in column 222.

Box 280 allows a user to select between two different Volts/cm types, namely "Linear" or "Non-Linear Lookup".

The default Volts/cm setting is "Linear", in which case the Voltage that is applied between a given pair of electrodes, as shown in column 222, is determined by the following formula:

$$\text{Voltage} = xd, \quad (1)$$

where x=the electric field density setting (Volts/cm) shown in column 225, which is based on the value from box 211, and where d=the distance (cm) between the given pair of electrodes shown in column 226.

Therefore, when "Linear" is selected, the Voltage that is applied between a given pair of electrodes is directly proportional to the Distance between the given electrode pair in a linear relationship.

If the user selects "Non-Linear Lookup" in box 280, then the Voltage that is applied between the given pair of electrodes will be similar to the Voltage values for a "Linear" selection when a pair of electrodes are closely spaced together (e.g. within about 1 cm). However, as a pair of given electrodes are spaced farther from one another, a "Non-Linear Lookup" will produce lower Voltages between the given pair of electrodes as compared to the Voltage values for a "Linear" selection at any given distance. The "Non-Linear Lookup" feature is particularly useful for reducing "popping" during treatment. "Popping" refers to an audible popping noise that sometimes occurs, which is believed to be caused by a plasma discharge from high voltage gradients at the tip of the electrodes. The "Non-Linear Lookup" feature can also minimize any swelling of the tissue that might occur as a result of a treatment. The Voltage values used for the "Non-Linear Lookup" selection can be pre-determined based on animal experiments and other research. In one embodiment, different tissue types can each have their own "Non-Linear Lookup" table. In the example shown, the tissue being treated is prostate tissue.

The details of the treatment parameters are displayed in window 270. The firing (switching) sequence between probes is listed automatically in window 270. In the example, the firing sequence involves six steps beginning with between probes 1 and 2, then probes 1 and 3, then probes 2 and 3, then probes 2 and 4, then probes 3 and 4, and then probes 4 and 1. As shown, the polarity of each of the probes may switch from negative to positive according to step of the firing sequence. Column 220 displays which probe is the positive probe (according to a number assigned to each probe) for each step. Column 221 displays which probe is the negative probe (according to a number assigned to each probe) for each step. Column 222 displays the actual voltage generated between each probe during each step of the firing sequence. In the example, the maximum voltage that can be generated between probes is limited by the capabilities of the generator 10, which in the example is limited to a maximum of 3000 Volts. Column 223 displays the length of each pulse that is generated between probes during each respective step of the firing sequence. In the example, the pulse length is predetermined and is the same for each respective step, and is set at 100 microseconds. Column 224 displays the number of pulses that is generated during each respective step of the firing sequence. In the example, the number of pulses is predetermined and is the same for each respective step, and is set at 90 pulses which are applied in a set of 10 pulses at a time. Column 225 displays the setting for Volts/cm according to the value selected at input box 211. Column 226 displays the actual distance between the electrodes (measured in cm), which is automatically calculated according to the placement of each probe in the grid 200.

The treatment control module 54 can be programmed to calculate and display the area of the combined treatment regions on the grid 200 by several different methods.

Figure 6:
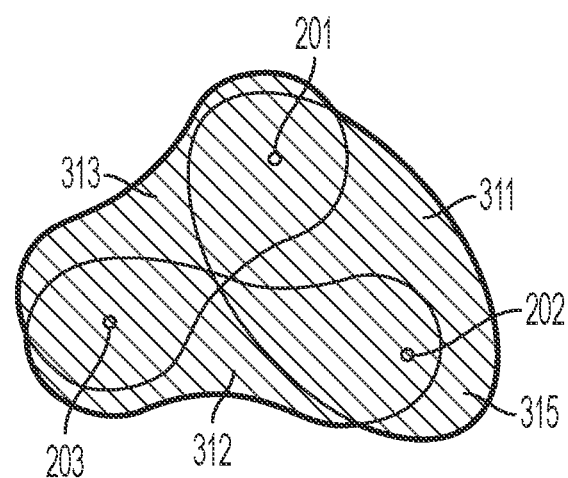
FIG. 6 illustrates an example of a three probe array defining three individual treatment zones, which combine to form a combined treatment region.

Each method determines a boundary line surrounding a treatment zone that is created between a pair of electrodes. By combining a plurality of treatment zones with each treatment zone being defined by a pair of electrodes, a combined treatment region can be displayed on the x-y grid. FIG. 6 illustrates three electrodes 201 (E1), 202 (E2), 203 (E3) defining three individual treatment zones 311, 312, 313, which combine to form a combined treatment region 315 which is shown with hatched lines.

As discussed above, the monitor can further include an x-z grid to illustrate the depth of the lesion and the shape of the treatment region. The shape of the treatment zone in the x-z grid will vary according to the selected amounts of electrode exposure for each probe and can be determined by one or more methods.

In one embodiment, the treatment boundary line that is created between two points on the x-y grid can be rotated about an axis joining the two points in order to generate the treatment region boundary line on the x-z grid. In this embodiment, several points may be selected along the exposed length of the active electrode portion for each probe at various depths (z). A three-dimensional combined treatment region can then be generated by determining the boundary line on the x-y grid between each individual pair of points and then rotating the boundary line along the axis joining each pair of points. The resulting boundary lines can be combined to create a three dimensional image that is displayed on the monitor.

The following is an alternate method for determining a boundary line on the x-z grid, thereby determining a three dimensional treatment region. This example describes a two probe array with the probes being inserted in a parallel relationship and with the probes having the same amount of exposed portions of the electrode. In this example, the exposed portions of each probe start at the same "uppermost" depth (z) and end at the same "lowermost" depth (z). First, a treatment zone boundary line is created in the x-y plane at the uppermost depth (z). Next, the treatment zone boundary line is repeatedly created stepwise for all subsequently lower depths (z), preferably evenly spaced, until the lowermost depth (z) is reached. The result is a 3-D volume (stacked set of treatment zone boundary lines) having a flat top surface and a flat bottom surface. Next, two new focus points are selected, with the first focus point positioned midway between the probe positions in the x-y grid and near the uppermost depth (z) of the exposed electrode. The second focus point is also positioned midway between the probe positions in the x-y grid, but near the lowermost depth (z) of the exposed electrode. Next, a treatment zone boundary line is created in the x-z grid using one of the methods described earlier. The actual placement of each focus point may be closer together, namely, not positioned in the uppermost and lowermost x-y planes defined by the exposed portions. The placement of each focus point should be selected so that the treatment zone boundary line that is created in the x-z grid closely matches the treatment zone boundary lines that were created in the uppermost and lowermost x-y grids. Next, the treatment zone boundary line that was created in the x-z grid according to the two focus points is rotated about the axis joining the two focus points. This creates the shapes for the upper and lower 3-D volumes which are added to the flat top surface and the flat bottom surface described above.

The above methods can be applied by persons of ordinary skill in the art to create 3-D treatment zones between exposed portions of electrodes even when the probes are not parallel to each other and even when the amount of the exposed portion varies with each probe.

Furthermore, there are situations where it is advantageous to show multiple boundary zones as a result of a therapy. For example, indicating which regimes undergo no change, reversible electroporation, irreversible electroporation, and conventional thermal damage is possible in accordance with the present invention. In addition, it is possible to output the entire distribution rather than just delineating boundaries.

It has been shown repeatedly in the literature that tissue properties are highly variable between tissue types, between individuals, and even within an individual. These changes may result from differences in body fat composition, hydration levels, and hormone cycles. Due to the large dependence of IRE (irreversible electroporation) treatments on tissue conductivity, it is imperative to have accurate values. Therefore, to obtain viable conductivity values prior to treatment, a low amplitude voltage pulse is used between the electrode conductors and the resultant impedance/conductance is measured as a way to determine pertinent tissue property data such as the predicted current. The value determined may then be implemented when assessing field strength and treatment protocol in real time. For example, the resulting impedance or predicted current can be used to set the default electric field density.

One method of generating an estimated treatment region between a pair of treatment electrodes is a numerical model based method involving finite element analysis (FEA). For example, U.S. Patent Application Publication No. 2007/0043345, which is hereby incorporated by reference, discloses using FEA models to generate treatment zones between a pair of electrodes (the calculations were performed using MATLAB's finite element solver, Femlab v2.2 (The MathWorks, Inc. Natick, Mass.)).

Most engineering problems can be solved by breaking the system into cells where each corner of the cell or mesh is a node. FEA is used to relate each node to each of the other nodes by applying sets of partial differential equations. This type of a system can be coded by scratch, but most people use one of many commercial FEA programs that automatically define the mesh and create the equations given the model geometry and boundary conditions. Some FEA programs only work in one area of engineering, for example, heat transfer and others are known as multiphysics. These systems can convert electricity to heat and can be used for studying the relationships between different types of energy.

Typically the FEA mesh is not homogeneous and areas of transition have increased mesh density. The time and resources (memory) required to solve the FEA problem are proportional to the number of nodes, so it is generally unwise to have a uniformly small mesh over the entire model. If possible, FEA users also try to limit the analysis to 2D problems and/or use planes of symmetry to limit the size of the model being considered because even a modest 2D model often requires 30 minutes to several hours to run. By comparison, a 3D Model usually takes several hours to several days to run. A complicated model like a weather system or a crash simulation may take a super computer several days to complete.

Depending on the complexity of the FEA models that are required, the purchase price of the FEA modeling software can cost several thousand dollars for a low end system to $30 k for a non linear multiphysics system. The systems that model the weather are custom made and cost tens of millions of dollars.

In one example, the steps which are required for generating a treatment zone between a pair of treatment probes using finite element analysis include: (1) creating the geometry of interest (e.g., a plane of tissue with two circular electrodes); (2) defining the materials involved (e.g., tissue, metal); (3) defining the boundary conditions (e.g., Initial voltage, Initial temperature); (4) defining the system load (e.g., change the voltage of the electrodes to 3,000V); (5) determining the type of solver that will be used; (6) determining whether to use a time response or steady state solution; (7) running the model and wait for the analysis to finish; and (8) displaying the results.

Using FEA, however, may not be practical for use in calculating and displaying in real time a treatment zone that is created between a pair of treatment probes in accordance with the present invention because of the time required to run these types of analyses. For the present invention, the system should allow a user to experiment with probe placement and should calculate a new treatment zone in less than a few seconds. Accordingly, the FEA model is not appropriate for such use and it would be desirable to find an analytic solution (closed form solution), which can calculate the treatment zones with only simple equations, but which closely approximate the solutions from a numerical model analysis such as the finite element analysis. The closed loop solutions should preferably generate the treatment zone calculation in a fraction of a second so as to allow a physician/user to experiment with probe placement in real time.

There are different closed loop (analytical model analysis) methods for estimating and displaying a treatment zone between a pair of treatment probes, which produce similar results to what would have been derived by a numerical model analysis such as FEA, but without the expense and time of performing FEA. Analytical models are mathematical models that have a closed form solution, i.e., the solution to the equations used to describe changes in a system can be expressed as a mathematical analytic function. The following method represents just one of the non-limiting examples of such alternative closed loop solutions.

In mathematics, a Cassini oval is a set (or locus) of points in the plane such that each point p on the oval bears a special relation to two other fixed points $q_1$ and $q_2$: the product of the distance from p to $q_1$ and the distance from p to $q_2$ is constant. That is, if the function dist(x,y) is defined to be the distance from a point x to a point y, then all points p on a Cassini oval satisfy the equation:

$$\text{dist}(q_1,p) \times \text{dist}(q_2,p) = b^2 \quad (2)$$

where b is a constant.

The points $q_1$ and $q_2$ are called the foci of the oval.

Suppose $q_1$ is the point (a,0), and $q_2$ is the point (-a,0). Then the points on the curve satisfy the equation:

$$((x-a)^2+y^2)((x+a)^2+y^2)=b^4 \quad (3)$$

The Equivalent Polar Equation is:

$$r^4-2a^2r^2 \cos 2\theta = b^4-a^4 \quad (4)$$

The shape of the oval depends on the ratio b/a. When b/a is greater than 1, the locus is a single, connected loop. When b/a is less than 1, the locus comprises two disconnected loops. When b/a is equal to 1, the locus is a lemniscate of Bernoulli.

The Cassini equation provides a very efficient algorithm for plotting the boundary line of the treatment zone that was created between two probes on the grid 200. By taking pairs of probes for each firing sequence, the first probe is set as $q_1$ being the point (a,0) and the second probe is set as $q_2$ being the point (-a, 0).

The polar equation for the Cassini curve is preferably used because it provides a more efficient equation for computation. The current algorithm can work equally as well by using the Cartesian equation of the Cassini curve. By solving for $r^2$ from eq. (4) above, the following polar equation was developed:

$$r^2 = a^2 \cos(2*\text{theta}) +/- \text{sqrt}(b^4-a^4 \sin^2(2*\text{theta})) \quad (5)$$

where a=the distance from the origin (0,0) to each probe in cm; and
where b is calculated from the following equation:

$$b^2 = \left[\frac{V}{[\ln(a)(595.28) + 2339]\left(\frac{A}{650}\right)}\right]^2 \quad (6)$$

where V=the Voltage (V) applied between the probes;
where a=the same a from eq. (5); and
where A=the electric field density (V/cm) that is required to ablate the desired type of tissue according to known scientific values.

As can be seen from the mathematics involved in the equation, r can be up to four separate values for each given value for theta.

Example 1

If V=2495 Volts; a=0.7 cm; and A=650 V/cm;
Then $b^2$=1.376377
and then a cassini curve can be plotted by using eq. (5) above by solving for r, for each degree of theta from 0 degrees to 360 degrees.

A portion of the solutions for eq. (5) are shown in Table 1 below:
where M=$a^2$ cos(2*theta); and L=sqrt($b^4-a^4$ $\sin^2$(2*theta))

TABLE 1

| Theta (degrees) | r = sqrt (M + L) | r = -sqrt (M + L) | r = sqrt (M - L) | r = -sqrt (M - L) |
|---|---|---|---|---|
| 0 | 1.366154 | -1.36615 | 0 | 0 |
| 1 | 1.366006 | -1.36601 | 0 | 0 |
| 2 | 1.365562 | -1.36556 | 0 | 0 |
| 3 | 1.364822 | -1.36482 | 0 | 0 |
| 4 | 1.363788 | -1.36379 | 0 | 0 |
| 5 | 1.362461 | -1.36246 | 0 | 0 |
| 6 | 1.360843 | -1.36084 | 0 | 0 |
| 7 | 1.358936 | -1.35894 | 0 | 0 |
| 8 | 1.356743 | -1.35674 | 0 | 0 |
| 9 | 1.354267 | -1.35427 | 0 | 0 |
| 10 | 1.351512 | -1.35151 | 0 | 0 |
| 11 | 1.348481 | -1.34848 | 0 | 0 |
| 12 | 1.34518 | -1.34518 | 0 | 0 |
| 13 | 1.341611 | -1.34161 | 0 | 0 |
| 14 | 1.337782 | -1.33778 | 0 | 0 |
| 15 | 1.333697 | -1.3337 | 0 | 0 |

The above eq. (6) was developed according to the following analysis.

The curve from the cassini oval equation was calibrated as best as possible to the 650 V/cm contour line using two 1-mm diameter electrodes with an electrode spacing between 0.5-5 cm and an arbitrary applied voltage.

For this worksheet, $q_1$ and $q_2$ reference points (taken to be +/−electrodes) could be moved to locations along the x-axis to points of (±a,0). A voltage could then be selected, and an arbitrary scaling factor ("gain denominator") would convert this voltage to the corresponding "b" used in eq. (4). The worksheet would then plot the resulting Cassini oval, which has a shape progression with applied voltage beginning as two circles around the electrodes that grow into irregular ellipses before converging into a single "peanut" shape that ultimately becomes an ellipse expanding from the original electrode locations.

The Cassini oval creates a reasonable visualization that mimics the shape of numerical results for the field distribution. In order to understand which values or levels correspond to a desired electric field of interest, a calibration involving the $b^4$ term was necessary to develop the relationship between the analytical Cassini oval and the numerical results. This was done through a backwards calibration process defined as follows:

1. A reference contour was selected to correlate the analytical and numerical solutions. This was chosen to be when b/a=1, forming a lemniscate of Bernoulli (the point where the two ellipses first connect, forming "∞").
2. A reference electric field density value was selected to be 650 V/cm.
3. Numerical models were developed to mimic the x-y output from the Cassini oval for scenarios where a=±0.25, 0.5, 0.75, 1.0, 1.25, 1.5, 1.75, 2.0, 2.25, and 2.5 cm.
4. Models were solved using trial and error to determine which voltage yielded the electric field contour of 650 V/cm in the shape of a lemniscate of Bernoulli.
5. The determined voltage was placed into the Cassini oval electronic worksheet for the same electrode geometry and the "gain denominator" was adjusted until the shape from the cassini oval matched that from the numerical solution.
6. The determined gain denominators for all values of "a" were collected and a calibration plot was made and fitted with a logarithmic trendline of:

$$\text{Gain Denominator} = 595.28 \cdot \ln(a) + 2339; R^2 = 0.993 \quad (7)$$

7. The calibration trendline function shown above was incorporated back into the Cassini Oval spreadsheet. At this point, the worksheet was capable of outputting a field contour of 650 V/cm for any electrode separation distance (±a) and applied voltage (V).
8. The calibration function was then scaled to a desired electric field contour input. This allowed the analytical solution to solve for any electric field for any given a separation distance and voltage. Since the Laplace equation is linear, scaling should provide a good estimate for how other fields would look.

Table 1 incorporates all the steps above to yield a single, calibrated Cassini Oval output that analytically predicts the electric field distribution; providing a quick and simple solution for the prediction of IRE (irreversible electroporation) treatment regions that may be adjusted in real-time. The inputs are the electrode location (as a given "±a" distance from the origin along the x-axis), the applied voltage to the energized electrode, and the desired electric field to visualize. The resulting output is a contour representing a threshold where the entire area within it has been subjected to an electric field the one selected; and thus treated by IRE. It is important to remember that the analytical solution was calibrated for an electric field contour of 650 V/cm, and thus yields an accurate approximation for this value. Other field strength contours of interest still yield reasonable results that mimic the overall shape of the electric field. Overall, the analytical solution provided yields consistently good predictions for electric field strengths, and thus, treatment regions of IRE that may be used during treatment planning or analysis.

A similar algorithm for calibration can be used for a bipolar electrode.

In one example, the diameter of the probe is 0.065 cm, and the lengths of the two electrodes are respectively 0.295 cm and 0.276 cm, separated by an insulation sleeve of 0.315 cm in length. Adapting this scenario to the cassini oval presents some challenges because the distribution is now resulting from the two exposed cylinder lengths, rather than two distinct loci of points. This was solved by calibrating individual electric field contours for the same applied voltage and developing two equations that adjust the separation distance (±a) and gain denominator (GD) according to the equations:

$$a = 710^{-9} \ast E^3 - 2 \ast 10^{-5} \ast E^2 + 0.015 \ast E + 6.1619; R^2 = 0.9806 \quad (8)$$

$$GD = 1.0121 \ast E + 1920; R^2 = 0.9928 \quad (9)$$

where E is the electric field magnitude contour desired. These two equations may then be used to calibrate the cassini ovals into a satisfactory shape to mimic the electric field distribution, and thus treatment region accordingly.

FIG. 6 illustrates an example of how to generate a combined treatment zone according to the invention. Three electrodes 201, 202, 203 defining three individual treatment zones 311, 312, 313, combine to form a combined treatment region 315 which is shown with hatched lines. By combining a plurality of treatment zones with each treatment zone being defined by a pair of electrodes, a combined treatment region 315 can be displayed on the x-y grid.

Figure 7:
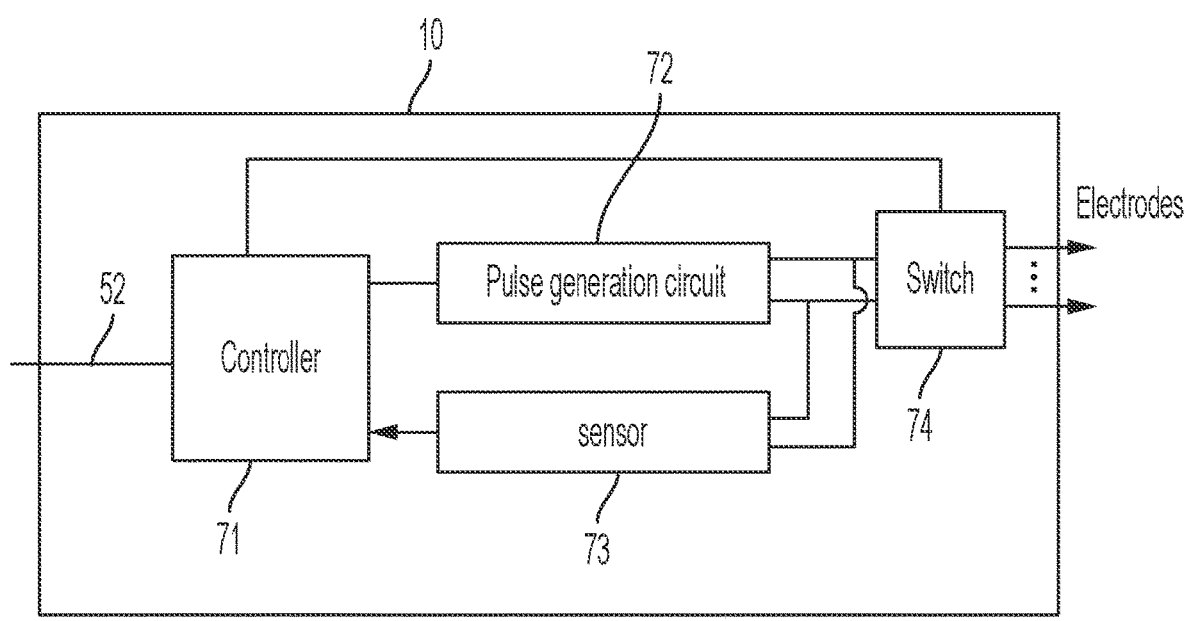
FIG. 7 illustrates details of the generator shown in FIG. 1.

FIG. 7 illustrates one embodiment of a pulse generator according to the present invention. A USB connection 52 carries instructions from the user computer 40 to a controller 71. The controller can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. In the embodiment shown, the pulses are applied one pair of electrodes at a time, and then switched to another pair using a switch 74, which is under the control of the controller 71. The switch 74 is preferably an electronic switch that switches the probe pairs based on the instructions received from the computer 40. A sensor 73 such as a sensor can sense the current or voltage between each pair of the probes in real time and communicate such information to the controller 71, which in turn, communicates the information to the computer 40. If the sensor 73 detects an abnormal condition during treatment such as a high current or low current condition, then it will communicate with the controller 71 and the computer 40 which may cause the controller to send a signal to the pulse generation circuit 72 to discontinue the pulses for that particular pair of probes.

The treatment control module 54 can further include a feature that tracks the treatment progress and provides the user with an option to automatically retreat for low or missing pulses, or over-current pulses (see discussion below). Also, if the generator stops prematurely for any reason, the treatment control module 54 can restart at the same point where it terminated, and administer the missing treatment pulses as part of the same treatment.

In other embodiments, the treatment control module 54 is able to detect certain errors during treatment, which include, but are not limited to, "charge failure", "hardware failure", "high current failure", and "low current failure".

According to the present invention, irreversible electroporation (IRE) ablation (n=81, where n is the number of IRE ablation procedures) was performed in-vivo in 22 pig livers using 2-4 IRE electrodes (18 gauge, 2 cm long tip) and a NanoKnife™ generator (AngioDynamics, Fremont, CA) as described in the IRE Treatment Application referenced above and as shown in FIGS. 1, 2 and 7. Cardiac-gated (i.e., synchronized to cardiac cycle) 100 μsec IRE pulses were applied sequentially between electrode pairs at 3,000-3,400V (one pair at a time).

Multiple variables for energy deposition and electrode configuration were studied including: inter-electrode spacing (1.5 cm-3 cm); the number of IRE pulses applied between electrode pairs (c=10, 50, & 100); and the order and number of times/cycles each electrode pair was activated.

For c=10, a sequence of delivered pulses are as follows: 10 sequential IRE pulses were delivered per electrode pair for all pairs (e.g., 10 pulses for pair 1-2, then 10 pulses for pair 2-3 and then 10 pulses for pair 3-1 for a 3-electrode array). Then the same sequence is repeated 2 to 44 times for a total number of IRE pulses delivered of 20 to 440 per electrode pair. Electrode phase (polarity) was changed after each sequence (1-2, 2-3, 3-1; 2-1, 3-2, 1-3), which reduces gas buildup near the electrodes to thereby reduce the chance of sparks. In one experiment, a total of 90 IRE pulses were delivered for each electrode pair.

For c=50, a sequence of 50 IRE pulses were delivered per electrode pair for all pairs. Then the same sequence is repeated one more time for a total number of IRE pulses delivered of 100 per electrode pair.

For c=100, a sequence of 100 sequential IRE pulses were delivered per each electrode pair. Then the same sequence is repeated one more time for a total number of IRE pulses delivered of 200 per electrode pair.

Between two pulses, two electrode pairs and two sequences, there is a waiting (delay) period. The reasons for the waiting period are to dissipate any thermal buildup in the tissue cells, especially around the electrodes where the current density is highest, and to increase the ablation zone.

Preferably, the generator 10 inserts a time delay between two pulses (inter-pulse delay) of at least 250 ms (milliseconds) and at most 15 seconds, and more preferably at least 1 second and at most 8 seconds. At greater than 8 seconds, the ablation zone does not increase and actually may help to decrease it.

Preferably, the generator 10 inserts a time delay of 5 seconds to 10 minutes between electrode pairs (inter-pair delay) within a sequence. Preferably, the generator inserts a time delay of 5 seconds to 20 minutes between two sequences (inter-sequence delay).

With a single IRE pulse, the cells try to close the holes/pores created in the membrane within a fraction of a second. By applying multiple pulses with inter-pulse, inter-pair and inter-sequence delays, it is believed that the cells' attempt to repeatedly close the holes exhaust their ability to close them, which thereby increases the ablation zone.

Ablations were performed under ultrasound guidance. Dimensions of resultant zones of treatment were measured by ultrasound 1-3 hr post-procedure and confirmed at gross and histopathology. These data and ablation times were compared and subject to statistical analysis to determine optimal pulse parameters.

Although the experiments involved 10, 50 and 100 pulses in a sequence, the general inventive concept can be expanded to include as little as 1 pulse per electrode pair in a sequence. In other words, for a 3 electrode array, a sequence of 1 IRE pulse per electrode pair is applied for all three pairs. Then, the sequence is repeated for 70 to 100 times. Preferably, the number of pulses for each electrode pair in a single sequence can vary between 1 and 280.

Currently, the NanoKnife generator is programmed to deliver a single IRE pulse per cardiac cycle if a cardiac-sync is selected. In a 3 or more multi-electrode array, more than one IRE pulse per cycle can be delivered by switching electrodes using the switch 74. For example, in a 3 electrode-array arrangement, in a single cardiac cycle, a sequence of single IRE pulse between pair 1-2, between pair 2-3 and between pair 2-3 can be applied for a total of 3 IRE pulses delivered, for example, within an R-wave of the cycle.

Alternatively, for applying 100 pulses, a sequence of 10 IRE pulses between pair 1-2, then between pair 2-3 and then between pair 2-3 can be applied for a total of 10 sets to deliver a total of 100 pulses for each electrode pair. For applying 500 pulses, a sequence of 10 IRE pulses can be sequentially applied to the 3 electrode pairs for a total of 50 sets. For applying 1000 pulses, a sequence of 10 IRE pulses can be sequentially applied to the 3 electrode pairs for a total of 100 sets.

The IRE pulses can be unipolar pulses or alternating polarity pulses such as biphasic pulses or consecutive positive and negative pulses separated by a slight time delay.

According to the experiments, the largest contiguous zones of treatment effect (6.4±0.6 cm width and length, 3.7±1.4 cm height) were achieved applying 2 cycles (sequences) of 50 IRE pulses sequentially to all electrode pairs within a 4 electrode array of 2.5 cm spacing (total time=17.5±6.7 min). For 4 electrode arrays, treatment diameter best correlated with overall time of the energy application [r2=0.71]). Greatest ablation for 3 electrode arrays (5.9±0.4 cm×5.3±0.5 cm cross-sectional area) was achieved by continuously delivering 10 pulses sequentially to each of the 3 electrode pairs for 10-12 min. For 2 electrode arrays using similar energy application strategies, ablation of only 3.9±0.5 cm length with variable width (incomplete to 2.4 cm) was achieved.

Figure 8:
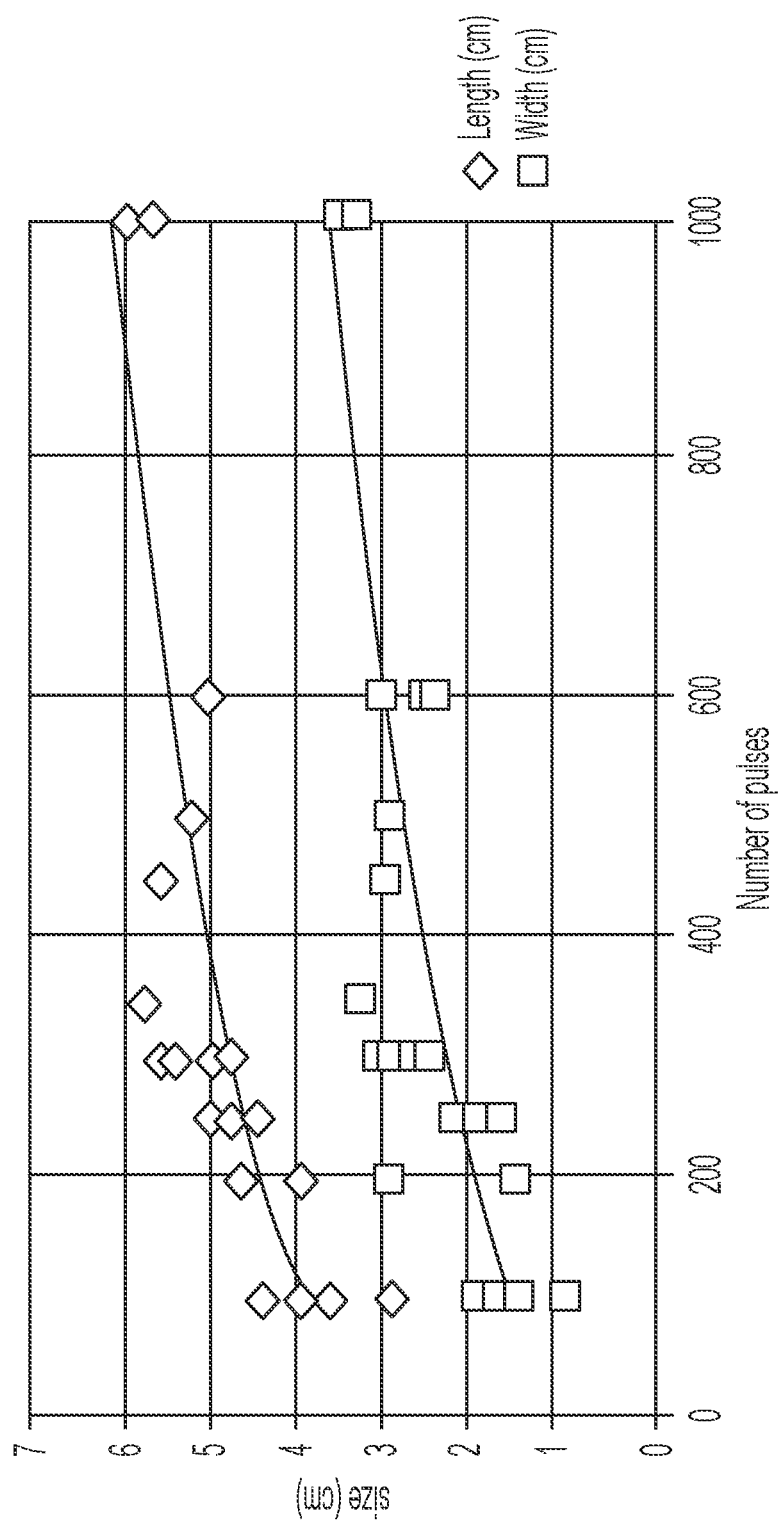
FIG. 8 is a graph illustrating the relationship of the number of pulses delivered and the size of the actual ablation region according to the present invention.

In another experiment, IRE ablation procedures were performed on porcine liver using the following parameters: 2.5 cm spacing between the electrodes, 100 μs pulses, 3 kVolts, 2 cm exposed electrodes, and 100-1000 pulses delivered. FIG. 8 is a graph illustrating the relationship of the number of pulses delivered to a pair of electrodes and the size of the actual ablation region in this experiment.

As can be seen, there is generally a positive correlation between the number of pulses (and therefore the total pulse application time) and the size of the ablation region although the rate of increase slows as more pulses are applied. For length, it varied between 4 cm and 5.7. For width, it varied between 1.5 cm and 3.3 cm. Using a curve fitting algorithm, the graph for length and width produced the following formulas:

$$y=1.6832*x-0.1849, \text{ where } x=\text{length in centimeter,}$$

and $$y=0.3407*x-0.3381, \text{ where } x=\text{width in centimeter.}$$

Table 2 below summarizes the experimental data in terms of the increase in size in two dimensions (area) and three dimensions (volume).

TABLE 2

| # of 100 μs pulses | Width of ablated region (cm) | Length of ablated region (cm) | 2-D ablated region (cm^2) | % increase in area | 3-D ablated volume (cm^3) | % increase in volume |
|---|---|---|---|---|---|---|
| 100 | 1.5 | 4 | 6 | NA | 24 | NA |
| 600 | 2.9 | 5.5 | 15.95 | 166% | 87.725 | 266% |
| 1000 | 3.3 | 6 | 19.8 | 230% | 118.8 | 395% |

As seen above, for two dimensional regions, increasing the number of pulses from 100 to 600 and 1000 respectively produced a surprisingly large increase of 166% and 230% in ablation area. If an assumption is made that the increase in depth is similar to the increase in length, then increasing the number of pulses from 100 to 600 and 1000 respectively produces an increase of 266% and 395% in ablation volume.

Based on the above relationship between the ablation size and the number of delivered pulses, calculation of the estimated treatment region can be adjusted accordingly. For example, if the experimental data show that the shape of the treatment region increases proportionally (width, length and depth of the region), then the term b^2 in the Cassini oval equation may be adjusted accordingly. If, however, the shape of the treatment region increases in a non-proportional manner (e.g., length increases at twice the rate as the width), then the Cassini oval equation can be modified by adding or subtracting a constant to the b^2 term (e.g., b^2+/−C) as well as adjusting the b^2 term itself. Alternatively, the number of electrodes can be reduced.

Aside from varying the number of applied pulses, varying the width of each pulse from 20 microseconds to 100 microseconds produced a slight increase in the ablation size. Increasing the pulse width, however, also reduced the variance in ablation size (i.e., reduction in standard deviation). As the pulse width increased past 50-70 microseconds, the variance among the ablation sizes decreased substantially. This effect became more pronounced for longer spacing between the electrodes (e.g., greater than 3 cm). Thus, this information could also be used to increase the ablation size and also to more accurately predict the ablation size.

In procedures involving 3 or more electrodes, rather than applying the total number of electrodes sequentially for each pair, then moving on to the next pair, dividing up the total number of pulses to be delivered into smaller subsets and then applying each subset of pulses to each pair, and then repeating the sequence for the subsequent subsets while reversing the polarity for each sequence (i.e., E1(+)–E2(−), then E2(+)–E1(−) in the next sequence) produced an increase in the ablation size, especially when the total number of pulses for each pair was substantially higher than 100.

For a 3-electrode procedure and the total number of pulses=500, for example, the sequence of delivered pulses are as follows: 10 sequential IRE pulses per electrode pair for all pairs (e.g., 10 pulses for pair 1-2, then 10 pulses for pair 2-3 and then 10 pulses for pair 3-1). Then the same sequence is repeated 50 times for a total number of IRE pulses delivered of 500 per electrode pair with the electrode phase (polarity) being reversed after each sequence.

Figure 9:
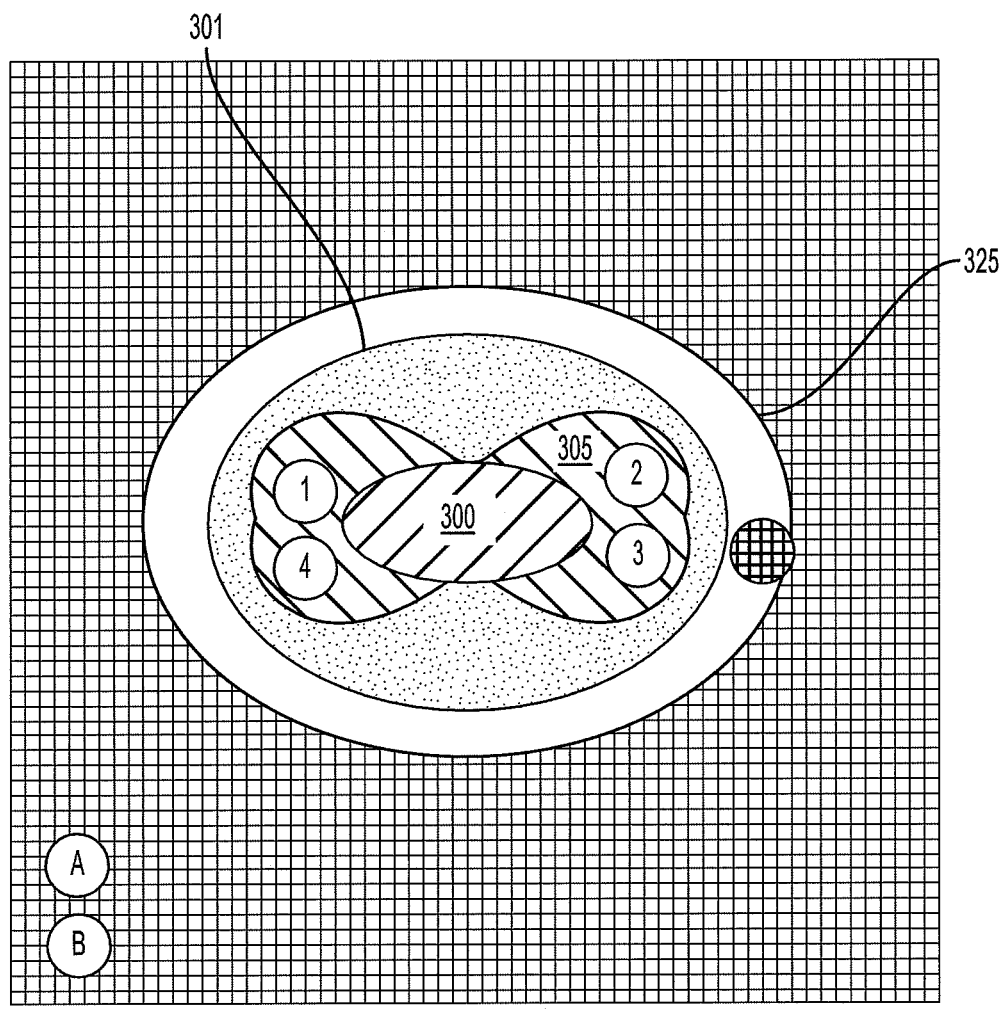
FIG. 9 illustrates ablation regions of varying sizes according to the number of pulses delivered according to the present invention.

FIG. 9 illustrates ablation regions of different sizes that are displayed on the monitor 11 according to the number of pulses delivered. The original lesion or target area 300 has been increased to an enlarged target region 301 which adds a margin of error. The estimated ablation area 305 has been generated assuming that 100 pulses will be delivered with four electrodes positioned as shown (superimposed over the target region 301). As can be seen, the estimated ablation/treatment area 305 barely covers the original target area 300 and is clearly inadequate to cover the enlarged target region 301.

However, according to the present invention, the enlarged target region 301 can be adequately covered by an increased ablation area 325 which has been calculated based on 1000 pulses (and which has been superimposed over the target region 301). Since such a large treatment area 325 can damage too much of good tissue, after receiving identification of a target region, the treatment control module 54 can select/adjust the number of pulses or number of electrodes, or both so that the resulting estimated treatment area sufficiently covers the target region 301 while minimizing ablation of good tissue. One way to do so is to generate a plurality of estimated ablation regions based on a plurality of pulse count, and then selecting the minimum pulse count that completely covers the target region 301 while minimizing damage to good tissue.

Advantageously, the present invention allows treatment of larger ablation regions with fewer electrodes to thereby provide a safer and less expensive electrical ablation procedure for patients. The present invention also allows treatment of a larger ablation area without dividing up the area into multiple regions and repeating the procedure.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed is:

1. A method of treating a target region of a tissue, the method comprising:
   disposing a plurality of electrodes near the target region; and
   activating a generator to deliver electrical pulses to the target region via the plurality of electrodes, wherein:
      a total number of electrical pulses to be applied between the plurality of electrodes is divided into subsets of at least 10 electrical pulses,
      each subset is sequentially applied between the plurality of electrodes until all of the electrodes have been activated to define a pulse cycle, and
      the pulse cycles are repeated until the total number of electrical pulses are applied,
   wherein a delay of between 250 milliseconds and 15 seconds is applied between each electrical pulse; and
   wherein a delay of between 5 seconds and 10 minutes is applied between each pulse subset.

2. The method of claim 1, wherein the plurality of electrodes comprises two or more electrodes.

3. The method of claim 1, wherein consecutive cycles of electrical pulses have opposite polarities.

4. The method of claim 1, wherein the tissue comprises prostate tissue.

5. The method of claim 1, wherein a delay of between 5 seconds to 20 minutes is applied between each pulse cycle.

6. The method of claim 1, wherein each pulse cycle comprises 1 to 280 pulses to be delivered between the plurality of electrodes.

7. The method of claim 1, wherein the pulse cycles are configured to allow for potential thermal buildup to dissipate or a reduction of potential gas buildup in the target region of the tissue surrounding the plurality of electrodes.

8. The method of claim 1, wherein consecutive pulses within a subset alternate polarity.

9. A method of electroporating a tissue, the method comprising:
   delivering a first subset of electrical pulses via a first pair of electrodes disposed within the tissue, wherein the first subset of electrical pulses is less than a total number of desired pulses to be applied by the first pair of electrodes;
   delivering a second subset of electrical pulses via a second pair of electrodes disposed within the tissue, wherein the second subset of electrical pulses is less than a total number of desired pulses to be applied by the second pair of electrodes, wherein the second pair of electrodes includes at least one different electrode from the first pair of electrodes; and
   delivering additional subsets of electrical pulses via the first and second pairs of electrodes sequentially until the total number of desired pulses for each pair is delivered,
   wherein the tissue comprises prostate tissue.

10. The method of claim 9, wherein the plurality of electrodes comprises three or more electrodes.

11. The method of claim 9, wherein each subset of electrical pulses comprises at least 10 electrical pulses.

12. The method of claim 11, wherein a delay of 250 milliseconds to 15 seconds is applied between each electrical pulse.

13. The method of claim 12, wherein a delay of 5 seconds to 10 minutes is applied between each pulse subset of electrical pulses.

14. The method of claim 9, wherein the electrical pulses are delivered in such a manner that the tissue is ablated by irreversible electroporation.

15. The method of claim 9, wherein the electrical pulses are delivered in such a manner that thermal buildup in the tissue surrounding each electrode is substantially dissipated or gas buildup in the tissue surrounding each electrode is substantially dissipated.

16. A method of irreversible electroporating a target tissue, the method comprising:
   electrically coupling a plurality of electrodes to a generator;
   disposing the plurality of electrodes near the target tissue; and
   activating the generator to deliver electrical pulses to the target tissue via the plurality of electrodes, wherein:
   the electrical pulses are delivered in a cycled pulse sequence such that a total number of electrical pulses delivered between the plurality of electrodes is divided into subsets of electrical pulses, and the plurality of electrodes are activated in a sequential order to deliver the subsets of electrical pulses to define a pulse cycle, and
   the pulse cycle is repeated until the total number of desired pulses are delivered,
   wherein the plurality of electrodes comprises two or more electrodes, each subset of electrical pulses comprises at least 10 electrical pulses, and a delay of between 5 seconds to 20 minutes is applied between each pulse cycle.

17. The method of claim 16, wherein the tissue comprises prostate tissue.

* * * * *